(12) United States Patent
Van Quaquebeke et al.

(10) Patent No.: US 7,741,337 B2
(45) Date of Patent: Jun. 22, 2010

(54) AZONAFIDE DERIVATIVES, METHODS FOR THEIR PRODUCTION AND PHARMACEUTICAL COMPOSITIONS THEREFROM

(75) Inventors: Eric Van Quaquebeke, Woluwé St. Lambert (BE); Jérôme Tuti, Jemeppe sur Sambre (BE); Laurent Van den Hove, Forest (BE); Robert Kiss, St.-Pieters Leeuw (BE); Francis Darro, Waterloo (BE)

(73) Assignee: Unibioscreen S.A., Brussels (BE)

( * ) Notice: Subject to any disclaimer, the term of this patent is extended or adjusted under 35 U.S.C. 154(b) by 31 days.

(21) Appl. No.: 12/093,086

(22) PCT Filed: Nov. 9, 2006

(86) PCT No.: PCT/EP2006/010727

§ 371 (c)(1),
(2), (4) Date: May 8, 2008

(87) PCT Pub. No.: WO2007/054292

PCT Pub. Date: May 18, 2007

(65) Prior Publication Data

US 2008/0292585 A1 Nov. 27, 2008

Related U.S. Application Data

(60) Provisional application No. 60/734,912, filed on Nov. 9, 2005.

(30) Foreign Application Priority Data

Nov. 9, 2005 (EP) .................................. 05447251

(51) Int. Cl.
*A61K 31/473* (2006.01)
*C07D 221/18* (2006.01)
(52) U.S. Cl. ............................ 514/284; 546/76; 546/75
(58) Field of Classification Search ................. 514/284; 546/76, 75
See application file for complete search history.

(56) References Cited

U.S. PATENT DOCUMENTS
5,635,506 A 6/1997 Alberts et al.

OTHER PUBLICATIONS

International Search Report (PCT/EP2006/010727), mailed Jun. 1, 2007.
Written Opinion of the International Searching Authority (PCT/EP2006/010727), mailed Jun. 1, 2007.
Response to the Written Opinion dated Jun. 1, 2007 (PCT/EP2006/010727), mailed Sep. 5, 2007.
International Preliminary Report on Patentability (PCT/EP2006/010727), mailed Feb. 15, 2008.

*Primary Examiner*—Charanjit S Aulakh
(74) *Attorney, Agent, or Firm*—Davidson, Davidson & Kappel, LLC

(57) ABSTRACT

The present invention is directed to azonafide derivatives obtained by reacting azonafide with aldehydes, acyl halides, thioacyl halides, monoisocyanates, isothiocyanates, sulfonyl halides, monohalogenoalkanes, monohalogenoalkenes or monohalogenoalkynes, and are useful as active ingredients of pharmaceutical compositions for the prevention and treatment of cell proliferative disorders, in particular several forms of cancer.

4 Claims, No Drawings

US 7,741,337 B2

AZONAFIDE DERIVATIVES, METHODS FOR THEIR PRODUCTION AND PHARMACEUTICAL COMPOSITIONS THEREFROM

CROSS-REFERENCE TO RELATED APPLICATIONS

This application is the U.S. National Stage of International Application No. PCT/EP2006/010727, filed Nov. 9, 2006, which claims the benefit of U.S. Provisional Application Ser. No. 60/734,912, filed Nov. 9, 2005, and European Patent Application Serial No. 05447251.9, filed Nov. 9, 2005.

TECHNICAL FIELD

The present invention relates to several classes of novel substituted 1,2-dihydro-3H-dibenzisoquinoline-1,3-dione derivatives (azonafides), synthetic methods for their production, and their medicinal use as anti-tumor agents, in particular in the form of pharmaceutical compositions including them as active principles in the prevention and/or treatment of various forms of cancer. The present invention also relates to methods of prevention and/or treatment of various forms of cancer in a mammal, preferably a human being, by the administration of a therapeutically effective amount of one or more of said novel substituted 1,2-dihydro-3H-dibenzisoquinoline-1,3-dione derivatives (azonafides) optionally in combination with one or more pharmaceutically acceptable excipients.

BACKGROUND OF THE INVENTION

Various kinds of substituted naphthalimides are known in the art as having anti-tumour effect or other useful biological activity.

Amonafide is an isoquinolinedione derivative which has undergone extensive tests for its anti-tumour activity. Although the level of activity found for amonafide was and continues to be of high interest, this material does have significant deficiencies which indicate the continuing need for agents with improved properties. In the first place, amonafide was found to be too toxic for some patients: in particular it has produced substantial myelotoxicity leading to some deaths in patients receiving five daily doses of the drug. In addition, it was shown that amonafide had only moderate activity in leukemia models in mice. Also, it was shown that amonafide has no activity in human tumour xenografts in mice with colon, lung and mammary cancers. Thus, while amonafide shows significant biological activity, it does not have a substantially broad spectrum of activity in murine tumour models. Ajani et al. in *Invest New Drugs* (1988) 6:79-83 has shown that amonafide has poor activity when tested in primary human solid tumours in vitro.

U.S. Pat. No. 5,635,506 discloses compounds based on anthracene instead of naphtalene and having the following formula:

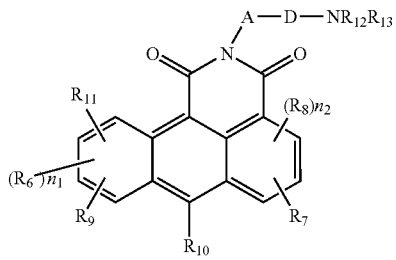

wherein:
A is $(CR_4R_5)n_3$, lower cycloalkylene or arylene or a chemical bond;
each $R_4$ and $R_5$ are independently hydrogen or lower alkyl;
D may be a chemical bond;
$R_{12}$ and $R_{13}$ may be independently hydrogen or an optionally substituted lower alkyl; and
$n_1$, $n_2$, $R_6$, $R_7$, $R_8$, $R_9$, $R_{10}$ and $R_{11}$ together form the substituting pattern of the anthracenyl moiety.

These compounds are described as being useful in treating cancer in animals and humans, e.g. against malignant tumors (especially solid tumors and leukemia).

In particular, 2-[2'-(dimethylamino)ethyl]-1,2-dihydro-3H-dibenz(deh)isoquinoline-1,3-dione (also called "azonafide") disclosed in this document showed anti-tumor activity on multidrug resistant tumors in vitro but did not completely maintain its activity with the human Myeloma 8226/DOX 40 cell line where a possible three-fold cross resistance was evident. Azonafide was also said to delay the appearance of tumors and to reduce tumor growth in mice with more efficiency than amonafide. On another hand, most of the compounds disclosed in this prior art document, including azonafide, showed a higher cardiotoxicity than amonafide.

Although the activity of antiproliferative agents such as amonafide or azonafide derivatives against certain forms of cancers can be shown, improvement in tumor response rates, duration of response, metastatic inhibition and ultimately patient survival are still sought. There is also a need in the art for improving the efficacy of antiproliferative treatments in humans by providing suitable combinations of new drugs with conventional antineoplastic agents. In view of the above-mentioned shortcomings of amonafide, azonafide and similar drugs available heretofore, the present inventors searched for azonafide derivatives which could demonstrate to be more effective anti-cancer agents. Specifically, they searched for compounds having one or more of the following characteristics:
1) increased tumor cell cytotoxic potency;
2) minimal, if any, cross resistance with multidrug resistant tumor cells;
3) relativity low cytotoxic potency in normal heart cells;
4) activity in a wide range of malignant tumors, especially solid tumors, hematological tumors, and leukemia; and
5) reduced myelotoxicity in humans at the tumor cell cytotoxic dosage.
6) Anti-migratory (anti-metastatic) effect As a result of their research, the present inventors have developed the following compounds, methods and compositions meeting these objectives.

SUMMARY OF THE INVENTION

In a first embodiment, the invention provides a family of substituted azonafide (1,2-dihydro-3H-dibenzisoquinoline-1,3-dione) derivatives represented by the formula (I) or the formula (II):

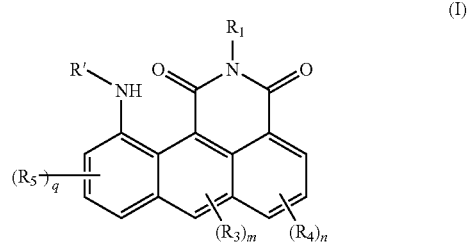

-continued

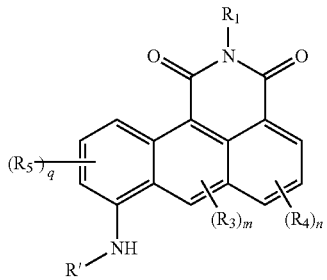

(II)

wherein:

R₁ is monoalkylaminoalkyl or dialkylaminoalkyl;

each of the substituents R₃ and R₄ is independently selected from the group consisting of hydrogen, halogen, $C_{1-7}$ alkyl, $C_{1-7}$ alkoxy, $C_{1-7}$ alkylthio, nitro, cyano, protected amino and halo $C_{1-7}$ alkyl;

m is the number of substituents R₃ and ranges from 0 to 1 n is the number of substituents R₄ and ranges from 0 to 3;

q is the number of substituents R₅ and ranges from 0 to 3; and

R' is a radical selected from the group consisting of $C_{1-12}$ alkyl, $C_{2-12}$ alkenyl, $C_{2-12}$ alkynyl, arylalkyl, Het¹alkyl, Het²alkyl, $C_{2-7}$ alkylsulfonyl, alkenylsulfonyl, alkynylsulfonyl, arylsulfonyl, aryloxyalkylsulfonyl, cycloalkylsulfonyl, arylalkylsulfonyl, Het¹sulfonyl, Het¹alkylsulfonyl, $C_{2-11}$ alkylcarbonyl, alkenylcarbonyl, alkynyl-carbonyl, arylcarbonyl, aminocarbonyl, alkyloxycarbonyl, alkenyloxycarbonyl, aryloxycarbonyl, aryloxyalkylcarbonyl, cycloalkylcarbonyl, arylalkylcarbonyl, Het¹-carbonyl, Het¹alkylcarbonyl, Het¹oxycarbonyl, Het¹alkyloxycarbonyl, alkylthiocarbonyl, alkenylthiocarbonyl, alkynylthiocarbonyl, arylthiocarbonyl, arylalkylthio-carbonyl, alkyloxythiocarbonyl, aryloxythiocarbonyl, alkyloxyalkylthiocarbonyl, aryloxyalkylthiocarbonyl, Het¹alkylthiocarbonyl, Het¹oxythiocarbonyl, Het¹alkyloxythiocarbonyl, alkylaminocarbonyl, alkenylaminocarbonyl, alkynylaminocarbonyl, arylaminocarbonyl, alkyloxyalkylaminocarbonyl, aryloxyalkylaminocarbonyl, cycloalkylaminocarbonyl, arylalkylaminocarbonyl, Het¹aminocarbonyl, Het¹alkylaminocarbonyl, Het¹oxyalkylaminocarbonyl, Het¹alkyloxyaminocarbonyl, alkylaminothiocarbonyl, alkenylthioaminocarbonyl, alkynylaminothiocarbonyl, arylaminothiocarbonyl, arylalkylthioaminocarbonyl, alkyloxyalkylaminothiocarbonyl, aryloxyalkylaminothiocarbonyl, Het¹alkylaminothiocarbonyl, Het¹aminothiocarbonyl and Het¹alkyloxyalkylthioaminocarbonyl, wherein one or more carbon atoms of said radical is (are) optionally substituted by one or more substituents independently selected from the group consisting of oxo, alkyl, cycloalkyl, alkyloxycarbonyl, carboxyl, aminocarbonyl, mono- or di-alkylaminocarbonyl, aminosulfonyl, alkylS(=O)$_r$, hydroxy, cyano, halogen, haloalkyl, alkoxy, haloalkoxy, nitro, amino, monoalkyl- and dialkylamino; and Het¹ and Het² are as defined in the section "Definitions" below, or by the formulae (III) or (IV)

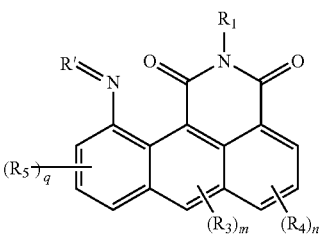

(III)

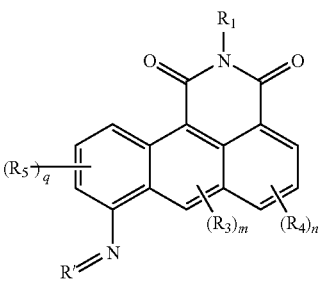

(IV)

wherein m, n, q, R₁, R₃, R₄ and R₅ are as defined with respect to formula (I) or formula (II), and R' is a radical selected from the group consisting of alkylidene, alkenylidene, alkynylidene, cycloalkenylidene, arylalkenylidene, arylalkynylidene, cycloalkylidene, arylalkylidene, Het¹alkylidene and Het²alkylidene, wherein one or more carbon atoms of said radical are optionally substituted by one or more substituents independently selected from the group consisting of alkyl, hydroxy, cyano, halogen, amino and dialkylamino;

and/or a pharmaceutically acceptable salt thereof and/or a solvate thereof.

The above defined novel compounds have in common the structural feature that the amino group of an amino-substituted azonafide derivative is substituted by a functional group, the term functional including the presence of a carbonyl or thiocarbonyl or sulfonyl group (formulae I and II) or the presence of an imino unsaturation (formulae III and IV).

In a second embodiment, the invention provides a method for the production of substituted azonafide derivatives represented by the formulae (I) or (II) by reacting an amino-substituted azonafide derivative with a reagent capable of reacting with the amino-substituent thereof, e.g. a reactant selected from the group consisting of acyl halides, thioacyl halides, isocyanates, isothiocyanates, monohalogenoalkanes, monohalogenoalkenes, monohalogenoalkynes, and sulfonyl halides. In a third embodiment, the invention provides a method for the production of substituted azonafide derivatives represented by the general formula (III) or (IV) by reacting an amino-substituted azonafide derivative with a suitable aliphatic, cycloaliphatic, aromatic or heterocyclic aldehyde. In yet another embodiment, the invention provides a method for the production of addition salts and/or solvates of said substituted azonafide derivatives.

In another embodiment, the invention provides a pharmaceutical composition comprising:

a therapeutically effective amount of a substituted azonafide derivative represented by the formula (I), (II), (III) or (IV), and/or a pharmaceutically acceptable salt thereof and/or a solvate thereof, and one or more pharmaceutically acceptable carriers.

In another embodiment, the invention provides combined preparations containing at least one substituted azonafide derivative represented by the formula (I), (II), (III) or (IV) and/or a pharmaceutically acceptable salt thereof and/or a solvate thereof, and one or more antineoplastic drugs, preferably in the form of synergistic combinations as detailed below.

In another embodiment, the invention relates to the unexpected finding that substituted azonafide derivatives represented by the formula (I), (II), (III) or (IV), and/or a pharmaceutically acceptable salt thereof and/or a solvate thereof, have significantly higher biological activity, especially with respect to tumour cells, than azonafide while avoiding many of the above-mentioned drawbacks of azonafide. In particular, the azona-fide derivatives according to this invention have a significant anti-migratory effect. Migration refers to the process whereby cells migrate from a neoplastic tumor tissue and colonize new tissues, using blood or lymphatic vessels as major routes of migration, this process being also known as the metastatic process. Based on this finding, the present invention provides a method for treating and/or preventing tumours in humans. More specifically, the invention relates to a method of treatment of a host with a cellular proliferative disease, comprising contracting said host with an effective amount of a substituted azonafide derivative represented by the formula (I), (II), (III) or (IV), and/or a pharmaceutically acceptable salt thereof and/or a solvate thereof.

In another embodiment, the invention provides the use of substituted azonafide derivatives represented by the formula (I), (II), (III) or (IV), and/or a pharmaceutically acceptable salt thereof and/or a solvate thereof, as anti-tumour agents.

DEFINITIONS

As used herein with respect to a substituting radical, and unless otherwise stated, the term "alkyl" means straight and branched chain saturated acyclic hydrocarbon monovalent radicals having from 1 to 12 carbon atoms such as, for example, methyl, ethyl, propyl, n-butyl, 1-methylethyl (isopropyl), 2-methylpropyl (isobutyl), 1,1-dimethylethyl (terbutyl), 2-methylbutyl, n-pentyl, dimethylpropyl, n-hexyl, 2-methylpentyl, 3-methylpentyl, n-heptyl, 2-methylhexyl, n-octyl, isooctyl, n-nonyl, n-decyl, n-undecyl, n-dodecyl and the like. When a narrower definition is intended, e.g. when a notation such as $C_{2-7}$ alkyl is used, this notation means that the substituting radical has from 2 to 7 carbon atoms.

As used herein with respect to a substituting radical, and unless otherwise stated, the term "alkylene" means a divalent saturated hydrocarbon radical corresponding to the above defined alkyl, such as but not limited to methylene, bis(methylene), tris(methylene), tetramethylene, hexamethylene and the like.

As used herein with respect to a substituting radical, and unless otherwise stated, the term "alkylidene" means a divalent saturated hydrocarbon radical formally derived by removal of two hydrogen atoms from the same carbon atom of the corresponding alkyl (such as defined above), such as but not limited to methylidene, ethylidene and the like.

As used herein with respect to a substituting radical, and unless otherwise stated, the term "alkenyl" designates a straight and branched acyclic hydrocarbon monovalent radical having one or more ethylenic unsaturations and having from 2 to 7 carbon atoms such as, for example, vinyl, 1-propenyl, 2-propenyl (allyl), 1-butenyl, 2-butenyl, 2-pentenyl, 3-pentenyl, 3-methyl-2-butenyl, 3-hexenyl, 2-hexenyl, 2-heptenyl, 1,3-butadienyl, pentadienyl, hexadienyl, heptadienyl, heptatrienyl and the like, including all possible isomers thereof.

As used herein with respect to a substituting radical, and unless otherwise stated, the term "alkenylidene" means a divalent unsaturated hydrocarbon radical formally derived by removal of two hydrogen atoms from the same carbon atom of the corresponding alkenyl (such as defined above), such as but not limited to ethenylidene, propylidene and the like.

As used herein with respect to a substituting radical, and unless otherwise stated, the term "alkynyl" defines straight and branched chain hydrocarbon radicals containing one or more triple bonds and optionally at least one double bond and having from 2 to 7 carbon atoms such as, for example, acetylenyl, 1-propynyl, 2-propynyl, 1-butynyl, 2-butynyl, 2-pentynyl, 1-pentynyl, 3-methyl-2-butynyl, 3-hexynyl, 2-hexynyl, 1-penten-4-ynyl, 3-penten-1-ynyl, 1,3-hexadien-1-ynyl and the like.

As used herein with respect to a substituting radical, and unless otherwise stated, the term "cycloalkyl" means a mono- or polycyclic saturated hydrocarbon monovalent radical having from 3 to 10 carbon atoms, such as for instance cyclopropyl, cyclobutyl, cyclopentyl, cyclohexyl, cycloheptyl, cyclooctyl and the like, or a $C_{7-10}$ polycyclic saturated hydrocarbon monovalent radical having from 7 to 10 carbon atoms such as, for instance, norbornyl, fenchyl, trimethyltricycloheptyl or adamantyl.

As used herein with respect to a substituting radical, and unless otherwise stated, the term "cycloalkylene" means the divalent hydrocarbon radical corresponding to the above defined cycloalkyl.

As used herein with respect to a substituting radical, and unless otherwise stated, the term "acyl" broadly refers to a substituent derived from an acid such as an organic monocarboxylic acid, a carbonic acid, a carbamic acid (resulting into a carbamoyl substituent) or the thioacid or imidic acid (resulting into a carbamidoyl substituent) corresponding to said acids; a more specific kind of "acyl" group within the scope of the above definition refers to a carbonyl (oxo) group adjacent to an alkyl radical, a cycloalkyl radical, an aryl radical, an arylalkyl radical or a heterocyclic (including $Het^1$ and $Het^2$) radical, all of them being such as herein defined (similarly, the term "thioacyl" refers to a C=S (thioxo) group adjacent to one of the said radicals;

As used herein with respect to a substituting radical, and unless otherwise stated, the term "sulfonyl" refers to a substituent derived from an organic sulfonic acid, wherein said acids comprise an aliphatic, aromatic or heterocyclic group in the molecule.

Acyl and sulfonyl groups originating from aliphatic or cycloaliphatic monocarboxylic acids are designated herein as aliphatic or cycloaliphatic acyl and sulfonyl groups; they may be part of acyl halides and sulfonyl halides suitable as reagents for producing the novel compounds of the present invention and include, but are not limited to, the following:

alkanoyl (for example formyl, acetyl, propionyl, butyryl, isobutyryl, valeryl, isovaleryl, pivaloyl and the like);

cycloalkanoyl (for example cyclobutanecarbonyl, cyclopentanecarbonyl, cyclohexanecarbonyl, 1-adamantanecarbonyl and the like);

cycloalkyl-alkanoyl (for example cyclohexylacetyl, cyclopentylacetyl and the like);

alkenoyl (for example acryloyl, methacryloyl, crotonoyl and the like);

alkylthioalkanoyl (for example methylthioacetyl, ethylthioacetyl and the like);

alkanesulfonyl (for example mesyl, ethanesulfonyl, propanesulfonyl and the like);

alkoxycarbonyl (for example methoxycarbonyl, ethoxycarbonyl, propoxycarbonyl, isopropoxycarbonyl, butoxycarbonyl, isobutoxycarbonyl and the like);

alkylcarbamoyl (for example methylcarbamoyl and the like);

(N-alkyl)-thiocarbamoyl (for example (N-methyl)-thiocarbamoyl and the like);

alkylcarbamidoyl (for example methylcarbamidoyl and the like); and alkoxalyl (for example methoxalyl, ethoxalyl, propoxalyl and the like);

Acyl and sulfonyl groups may also originate from aromatic monocarboxylic acids; they may be part of acyl halides and sulfonyl halides suitable as reagents for producing the novel compounds of the present invention and include, but are not limited to, the following:

aroyl (for example benzoyl, toluoyl, xyloyl, 1-naphthoyl, 2-naphthoyl and the like);

aralkanoyl (for example phenylacetyl and the like);

aralkenoyl (for example cinnamoyl and the like);

aryloxyalkanoyl (for example phenoxyacetyl and the like);

arylthioalkanoyl (for example phenylthioacetyl and the like);

arylaminoalkanoyl (for example N-phenylglycyl, and the like);

arylsulfonyl (for example benzenesulfonyl, toluenesulfonyl, naphthalene sulfonyl and the like);

aryloxycarbonyl (for example phenoxycarbonyl, naphthyloxycarbonyl and the like);

aralkoxycarbonyl (for example benzyloxycarbonyl and the like);

arylcarbamoyl (for example phenylcarbamoyl, naphthylcarbamoyl and the like);

arylglyoxyloyl (for example phenylglyoxyloyl and the like).

arylthiocarbamoyl (for example phenylthiocarbamoyl and the like); and arylcarbamidoyl (for example phenylcarbamidoyl and the like).

Acyl groups may also originate from an heterocyclic monocarboxylic acids; they may be part of acyl halides suitable as reagents for producing the novel compounds of the present invention and include, but are not limited to, the following:

heterocyclic-carbonyl, in which said heterocyclic group is as defined herein, preferably an aromatic or non-aromatic 5- to 7-membered heterocyclic ring with one or more heteroatoms selected from the group consisting of nitrogen, oxygen and sulfur in said ring (for example thiophenoyl, furoyl, pyrrolecarbonyl, nicotinoyl and the like); and heterocyclic-alkanoyl in which said heterocyclic group is as defined herein, preferably an aromatic or non-aromatic 5- to 7-membered heterocyclic ring with one or more heteroatoms selected from the group consisting of nitrogen, oxygen and sulfur in said ring (for example thiopheneneacetyl, furylacetyl, imidazolylpropionyl, tetrazolylacetyl, 2-(2-amino-4-thiazolyl)-2-methoxyiminoacetyl and the like).

As used herein with respect to a substituting radical, and unless otherwise stated, the term "cycloalkylalkyl" refers to an aliphatic saturated hydrocarbon monovalent radical (preferably an alkyl such as defined above) to which a cycloalkyl (such as defined above) is already linked such as, but not limited to, cyclohexylmethyl, cyclopentylmethyl and the like.

As used herein with respect to a substituting radical, and unless otherwise stated, the term "aryl" designate any mono- or polycyclic aromatic monovalent hydrocarbon radical having from 6 to 30 carbon atoms such as but not limited to phenyl, naphthyl, anthracenyl, phenantracyl, fluoranthenyl, chrysenyl, pyrenyl, biphenylyl, terphenyl, picenyl, indenyl, biphenyl, indacenyl, benzocyclobutenyl, benzocyclooctenyl and the like, including fused benzo$C_{4-8}$ cycloalkyl radicals (the latter being as defined above) such as, for instance, indanyl, tetrahydronaphtyl, fluorenyl and the like, each of said radicals being optionally substituted with one or more substituents independently selected from the group consisting of halogen, amino, cyano, trifluoromethyl, hydroxyl, sulfhydryl and nitro, such as for instance 4-fluorophenyl, 4-chlorophenyl, 3,4-dichlorophenyl, 4-cyanophenyl, 2,6-dichlorophenyl, 2-fluorophenyl, 3-chlorophenyl, 3,5-dichlorophenyl and the like.

As used herein with respect to a substituting radical, and unless otherwise stated, the term "arylene" means a divalent hydrocarbon radical corresponding to the above defined aryl such as but not limited to phenylene, naphthylene, indenylidene and the like.

As used herein with respect to a substituting radical, and unless otherwise stated, the term "Het$^1$" alone or in combination with another radical is defined as a saturated or partially unsaturated monocyclic, bicyclic or polycyclic heterocycle having preferably 3 to 12 ring members, more preferably 5 to 10 ring members and more preferably 5 to 6 ring members, which contains one or more heteroatom ring members selected from the group consisting of nitrogen, oxygen or sulfur and wherein one or more carbon atoms of said heterocycle is optionally substituted by one or more substituents selected from the group consisting of alkyl, alkoxy, halogen, hydroxy, oxo, sulhydryl, thioxo, thioalkyl, amino, nitro, cyano, haloalkyl, carboxyl, alkyloxycarbonyl, cycloalkyl, aminocarbonyl, methylthio, methylsulfonyl, aryl, saturated or partially unsaturated monocyclic, bicyclic and tricyclic heterocycles having 3 to 12 ring members and having one or more hetero-atom ring members selected from the group consisting of nitrogen, oxygen and sulfur, mono- and disubstituted-amino, and mono- and disubstituted-aminocarbonyl, whereby the optional substituent(s) of the amino group are independently selected from the group consisting of alkyl, alkoxy, Het$^2$, Het$^2$alkyl, Het$^2$oxy, Het$^2$oxyalkyl, aryl, aryloxy, aryloxyalkyl, arylalkyl, alkyloxycarbonylamino, amino and aminoalkyl, wherein each of the latter amino groups may optionally be mono- or where possible di-substituted with alkyl;

As used herein with respect to a substituting radical, and unless otherwise stated, the term "Het$^2$" alone or in combination with another radical is defined as an aromatic monocyclic, bicyclic or tricyclic heterocycle having preferably 3 to 12, more preferably 5 to 10 and most preferably 5 to 6, ring members, which contains one or more heteroatom ring members selected from the group consisting of nitrogen, oxygen and sulfur, and wherein one or more carbon atoms of said heterocycle is optionally substituted by one or more substituents selected from the group consisting of alkyl, alkoxy, halogen, hydroxy, oxo, sulfhydryl, thioxo, thioalkyl, amino, nitro, cyano, haloalkyl, carboxyl, alkyloxy-carbonyl, cycloalkyl, aminocarbonyl, methylthio, methylsulfonyl, aryl, Het$^1$ and mono-cyclic, bicyclic or tricyclic heterocycles having 3 to 12 ring members and having one or more heteroatom ring members selected from the group consisting of nitrogen, oxygen and sulfur, mono- and disubstituted-amino, and mono- and disubstituted-aminocarbonyl, whereby the optional substituent(s) of the amino group are independently selected from the group consisting of alkyl, alkoxy, Het¹, Het¹alkyl, Het¹oxy, Het¹oxyalkyl, aryl, aryloxy, aryloxyalkyl, arylalkyl, alkyloxycarbonylamino, amino and aminoalkyl, each of the latter amino groups being optionally mono- or where possible di-substituted with alkyl;

As used herein with respect to a substituting radical, and unless otherwise stated, the term "heterocyclic" includes both Het¹ and Het²; specific examples thereof include, but are not limited to, naphthalimidyl, diazepinyl, oxadiazinyl, thiadiazinyl, dithiazinyl, triazolonyl, diazepinonyl, triazepinyl, triazepinonyl, tetrazepinonyl, benzoquinolinyl, benzothiazinyl, benzothiazinonyl, benzoxathiinyl, benzodioxinyl, benzodithiinyl, benzoxazepinyl, benzothiazepinyl, benzodiazepinyl, benzodioxepinyl, benzodithiepinyl, benzoxazocinyl, benzothiazocinyl, benzodiazocinyl, benzoxathiocinyl, benzodioxocinyl, benzotrioxepinyl, benzoxathiazepinyl, benzoxadiazepinyl, benzothiadiazepinyl, benzo-triazepinyl, benzoxathiepinyl, benzotriazinonyl, benzoxazolinonyl, azetidinonyl, aza-spiroundecyl, dithiaspirodecyl, hypoxanthinyl, azahypoxanthinyl, bipyrazinyl, bipyridinyl, oxazolidinyl, benzodioxocinyl, benzopyrenyl, benzopyranonyl, benzophenazinyl, benzo-quinolizinyl, dibenzocarbazolyl, dibenzoacridinyl, dibenzophenazinyl, dibenzothiepinyl, dibenzooxepinyl, dibenzopyranonyl, dibenzoquinoxalinyl, dibenzothiazepinyl, dibenzo-isoquinolinyl, tetraazaadamantyl, thiatetraazaadamantyl, oxauracil, oxazinyl, dibenzothiophenyl, dibenzofuranyl, oxazolinyl, oxazolonyl, azaindolyl, azolonyl, thiazolinyl, thiazolonyl, thiazolidinyl, thiazanyl, pyrimidonyl, thiopyrimidonyl, thiamorpholinyl, azlactonyl, naphtindazolyl, naphtindolyl, naphtothiazolyl, naphtothioxolyl, naphtoxindolyl, naphtotriazolyl, naphtopyranyl, oxabicycloheptyl, azabenzimidazolyl, azacycloheptyl, azacyclooctyl, azacyclononyl, azabicyclononyl, tetrahydrofuryl, tetrahydropyranyl, tetrahydropyronyl, tetrahydroquinoleinyl, tetrahydrothienyl and dioxide thereof, dihydrothienyl dioxide, dioxindolyl, dioxinyl, dioxenyl, dioxazinyl, thioxanyl, thioxolyl, thiourazolyl, thiotriazolyl, thiopyranyl, thiopyronyl, coumarinyl, quinoleinyl, oxyquinoleinyl, quinucli-dinyl, xanthinyl, dihydropyranyl, benzodihydrofuryl, benzothiopyronyl, benzothiopyranyl, benzoxazinyl, benzoxazolyl, benzodioxolyl, benzodioxanyl, benzothiadiazolyl, benzotriazinyl, benzothiazolyl, benzoxazolyl, phenothioxinyl, phenothiazolyl, phenothienyl (benzothiofuranyl), phenopyronyl, phenoxazolyl, pyridinyl, dihydropyridinyl, tetrahydro-pyridinyl, piperidinyl, morpholinyl, thiomorpholinyl, pyrazinyl, pyrimidinyl, pyridazinyl, triazinyl, tetrazinyl, triazolyl, benzotriazolyl, tetrazolyl, imidazolyl, pyrazolyl, thiazolyl, thiadiazolyl, isothiazolyl, oxazolyl, oxadiazolyl, pyrrolyl, furyl, dihydrofuryl, furoyl, hydantoinyl, dioxolanyl, dioxolyl, dithianyl, dithienyl, dithiinyl, thienyl, indolyl, indazolyl, benzofuryl, quinolyl, quinazolinyl, quinoxalinyl, carbazolyl, phenoxazinyl, phenothiazinyl, xanthenyl, purinyl, benzothienyl, naphtothienyl, thianthrenyl, pyranyl, pyronyl, benzopyronyl, isobenzofuranyl, chromenyl, phenoxathiinyl, indolizinyl, quinolizinyl, isoquinolyl, phthalazinyl, naphthiridinyl, cinnolinyl, pteridinyl, carbolinyl, acridinyl, perimidinyl, phenanthrolinyl, phenazinyl, phenothiazinyl, imidazolinyl, imidazolidinyl, benzimidazolyl, pyrazolinyl, pyrazolidinyl, pyrrolinyl, pyrrolidinyl, piperazinyl, uridinyl, thymidinyl, cytidinyl, azirinyl, aziridinyl, diazirinyl, diaziridinyl, oxiranyl, oxaziridinyl, dioxiranyl, thiiranyl, azetyl, dihydroazetyl, azetidinyl, oxetyl, oxetanyl, oxetanonyl, thietyl, thietanyl, diazabicyclooctyl, diazetyl, diaziridinonyl, diaziridinethionyl, chromanyl, chromanonyl, thiochro-manyl, thiochromanonyl, thiochromenyl, benzofuranyl, benziso-thiazolyl, benzocarbazolyl, benzochromonyl, benzisoalloxazinyl, benzocoumarinyl, thio-coumarinyl, phenometoxazinyl, phenoparoxazinyl, phentriazinyl, thiodiazinyl, thiodiazolyl, indoxyl, thioindoxyl, benzodiazinyl (e.g. phtalazinyl), phtalidyl, phtalimidinyl, phtalazonyl, alloxazinyl, dibenzopyronyl (i.e. xanthonyl), xanthionyl, isatyl, isopyrazolyl, isopyra-zolonyl, urazolyl, urazinyl, uretinyl, uretidinyl, succinyl, succinimido, benzylsultimyl, benzylsultamyl and the like, including all possible isomeric forms thereof.

As used herein with respect to a substituting radical, and unless otherwise stated, the term "Het¹-ylidene" means a divalent radical formally derived by removal of two hydrogen atoms from the same carbon atom of the corresponding Het¹ radical, such as but not limited to pyrrolinylidene, piperidinylidene and the like.

As used herein with respect to a substituting radical, and unless otherwise stated, the terms "alkoxy", "aryloxy", "arylalkyloxy", "thioalkyl", "arylthio" and "arylalkyl-thio" refer to substituents wherein an alkyl radical, respectively an aryl or arylalkyl radical (each of them such as defined herein), are attached to an oxygen atom or a divalent sulfur atom through a single bond, such as but not limited to methoxy, ethoxy, propoxy, butoxy, pentoxy, isopropoxy, sec-butoxy, tert-butoxy, isopentoxy, cyclopropyloxy, cyclobutyloxy, cyclopentyloxy, thiomethyl, thioethyl, thiopropyl, thiobutyl, thiopentyl, thiocyclopropyl, thiocyclobutyl, thiocyclopentyl, thiophenyl, phenyloxy, benzyloxy, mercapto-benzyl, cresoxy and the like.

As used herein with respect to a substituting atom, and unless otherwise stated, the term "halogen" means any atom selected from the group consisting of fluorine, chlorine, bromine and iodine.

As used herein with respect to a substituting radical, and unless otherwise stated, the term "haloalkyl" means an alkyl radical (such as above defined) in which one or more hydrogen atoms are independently replaced by one or more halogens (preferably fluorine, chlorine or bromine), such as but not limited to difluoromethyl, trifluoromethyl, trifluoroethyl, octafluoropentyl, dodecafluoroheptyl, dichloromethyl and the like.

As used herein with respect to a substituting radical, and unless otherwise stated, the terms "arylalkyl", "cycloalkylalkyl", "Het¹alkyl" and "Het²alkyl" refer to an alipha-tic saturated hydrocarbon monovalent radical (preferably an alkyl radical such as defined above) onto which an aryl, cycloalkyl, Het¹ or Het² radical (such as defined above) is already linked, and wherein the said aliphatic radical and/or the said aryl or Het¹ or Het² radical may be optionally substituted with one or more substituents for instance independently selected from the group consisting of $C_{1-4}$ alkyl, trifluoromethyl, halogen, amino, nitro, hydroxyl, sulfhydryl and nitro, such as but not limited to benzyl, 4-chlorobenzyl, 2-fluorobenzyl, 4-fluorobenzyl, 3,4-dichlorobenzyl, 2,6-dichlorobenzyl, 4-ter-butylbenzyl, 3-methylbenzyl, 4-methyl benzyl, phenylpropyl, 1-naphtylmethyl, phenylethyl, 1-amino-2-phenyl-ethyl, 1-amino-2-[4-hydroxyphenyl]ethyl, 1-amino-2-[indol-2-yl] ethyl, styryl, pyridylmethyl (including all isomers thereof), pyridylethyl, 2-(2-pyridyl)-isopropyl, oxazolylbutyl, 2-thienylmethyl, pyrrolylethyl, morpholinylethyl, imidazol-1-yl-ethyl, benzodioxolylmethyl, cyclohexylmethyl, cyclopentylmethyl and 2-furylmethyl.

As used herein with respect to a substituting radical, and unless otherwise stated, the term "arylalkylidene" refers to an aliphatic saturated divalent radical (preferably an alkylidene radical such as defined above, more preferably methylidene) onto which one or two aryl radicals (such as defined above, preferably phenyl) is (are) already linked, such as but not limited to benzylidene, diphenylmethylene and the like.

As used herein with respect to a substituting radical, and unless otherwise stated, the term "arylalkenylidene" refers to an aliphatic ethylenically unsaturated divalent radical (preferably an alkenylidene radical such as defined above, more preferably propenylidene) onto which one or two aryl radicals (such as defined above, preferably phenyl) is (are) already linked, such as but not limited to cinnamylidene and the like.

As used herein with respect to a substituting radical, and unless otherwise stated, the term "arylalkynylidene" refers to an aliphatic acetylenically unsaturated divalent radical (preferably derived from an alkynyl radical such as defined above, more preferably propargyl) onto which one or two aryl radicals (such as defined above, preferably phenyl) is (are) already linked, such as but not limited to phenylpropargylidene and the like.

As used herein and unless otherwise stated, the term "solvate" includes any combination which may be formed by an azonafide derivative of this invention with a suitable inorganic solvent (e.g. hydrates) or organic solvent, such as but not limited to alcohols, ketones, esters and the like.

As used herein and unless otherwise stated, the term "antimigratory" refers to the ability of a pharmaceutical ingredient to stop the migration of cells away from the neoplastic tumor tissue and thus to reduce the colonization of new tissues by these cells.

DETAILED DESCRIPTION OF THE INVENTION

In a first aspect, the invention provides a family of substituted azonafide derivatives represented by the general formula (I) or (II):

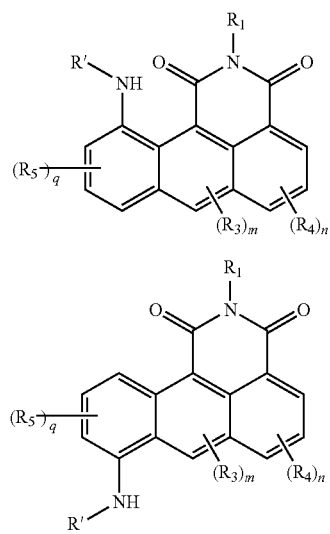

wherein each of m, n, q, $R_1$, $R_3$, R', $R_4$ and $R_5$ are as broadly defined herein-above, and/or a pharmaceutically acceptable salt thereof and/or a solvate thereof.

Within this broad family, the following embodiments are preferred n=0, and/or m=0, and/or q=0, and/or $R_1$ is an alkylene radical having 1 to 3 carbon atoms and linked to dimethylamino, and/or R' is selected from the group consisting of $C_{2-11}$ alkylcarbonyl, aminocarbonyl, alkylaminocarbonyl, alkyloxycarbonyl, aryloxycarbonyl, arylalkylcarbonyl, arylaminocarbonyl, arylaminothiocarbonyl, arylalkylaminocarbonyl and $Het^1$aminothiocarbonyl, and wherein one or more carbon atoms of said radical is (are) optionally substituted by one or more substituents independently selected from the group consisting of oxo, $Het^1$ and halogen.

In a second aspect, the invention provides a family of substituted azonafide derivatives represented by the following formula (III) or (IV):

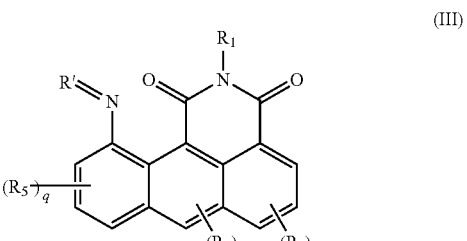

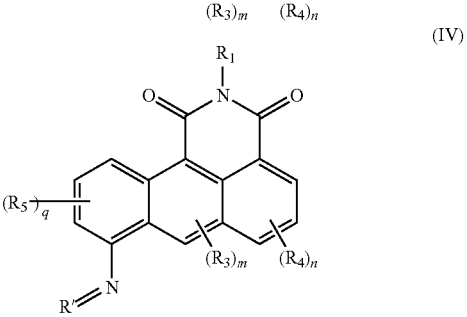

wherein each of m, n, q, $R_1$, $R_3$, R' $R_4$ and $R_5$ are as broadly defined hereinabove, and/or a pharmaceutically acceptable salt thereof and/or a solvate thereof.

Within this broad family, the following embodiments are preferred n=0, and/or m=0, and/or q=0, and/or $R_1$ is an alkylene radical having 1 to 3 carbon atoms and linked to dimethylamino or diethyl-amino, and/or R' is selected from the group consisting of alkylidene, alkenylidene, alkynylidene, cycloalkenylidene, cycloalkylidene, arylalkenylidene, arylalkynylidene, arylalkylidene, and $Het^1$alkylidene.

In another particular embodiment, the invention relates to a group of azonafide derivatives, as well as pharmaceutical compositions comprising such azonafide derivatives as an active principle, having one of the above formulae (I), (II), (III) or (IV) and being in the form of a pharmaceutically acceptable salt. The latter include any therapeutically active non-toxic salt which compounds having one of the formulae (I), (II), (III) or (IV) are able to form with a salt-forming agent. Such addition salts may conveniently be obtained by treating the azonafide derivatives of the invention with an appropriate salt-forming acid or base. For instance, azonafide derivatives having basic properties may be converted into the corresponding therapeutically active, non-toxic acid salt form by treating the free base form with a suitable amount of an appropriate acid following conventional procedures. Examples of such appropriate salt-forming acids include for instance inorganic acids resulting in forming salts such as, but not limited to, hydrohalides (e.g. hydrochloride or hydrobromide), sulfate, nitrate, phosphate, diphos-phate, carbonate, bicarbonate, and the like; and organic monocarboxylic or dicarboxylic acids resulting in forming salts such as acetate, propanoate, hydroxyacetate, 2-hydroxy-propanoate, 2-oxo-propanoate, lactate, pyruvate, oxalate, malonate, succinate, maleate, fumarate, malate, tartrate, citrate, methanesulfonate, ethanesulfonate, benzoate, 2-hydroxybenzoate, 4-amino-2-hydroxybenzoate, benzenesulfonate, p-toluene-sulfonate, salicylate, p-aminosalicylate, pamoate, bitartrate, camphor-sulfonate, edetate, 1,2-ethanedisulfonate, fumarate, gluco-heptonate, gluconate, glutamate, hexylresorcinate, hydrox-ynaphtoate, hydroxyethanesulfonate, mandelate, methylsulfate, pantothenate, stearate, as well as salts derived from ethanedioic, propanedioic, butanedioic, (Z)-2-butene-dioic, (E)2-butenedioic, 2-hydroxybutanedioic, 2,3-dihy-droxybutane-dioic, 2-hydroxy-1,2,3-propane-tricarboxylic, cyclohexane-sulfamic acid and the like.

Azonafide derivatives having one of the formulae (I), (II), (III) or (IV) having acidic properties may be converted in a similar manner into the corresponding therapeutically active, non-toxic base salt form. Examples of appropriate salt-form-ing bases include, for instance, inorganic bases like metallic hydroxides such as but not limited to those of alkali and alkaline-earth metals like calcium, lithium, magnesium, potassium and sodium, or zinc, resulting in the corresponding metal salt; organic bases such as but not limited to ammonia, alkylamines, benzathine, hydrabamine, arginine, lysine, N,N'-dibenzyl-ethylenediamine, chloroprocaine, choline, diethanolamine, ethylenediamine, N-methylglucamine, procaine and the like.

Reaction conditions for treating the azonafide derivatives having one of the formulae (I), (II), (III) or (IV) of this invention with an appropriate salt-forming acid or base are similar to standard conditions involving the same acid or base but different organic compounds with basic or acidic proper-ties, respectively. Preferably, in view of its use in a pharma-ceutical composition or in the manufacture of medicament for treating specific diseases, the pharmaceutically acceptable salt will be designed, i.e. the salt-forming acid or base will be selected so as to impart greater water-solubility, lower toxic-ity, greater stability and/or slower dissolution rate to the azonafide derivative of this invention.

In another aspect the invention relates to methods for mak-ing substituted azonafide derivatives represented by the for-mula (I) or (II) wherein each of m, n, q, $R_1$, $R_3$, R', $R_4$ and $R_5$ are as broadly defined hereinabove, by reacting an azonafide derivative (i.e. respectively a N—($R_1$-substituted)-11-amino-3H-dibenzo[deh]isoquinoline-1,3(2H)-dione or a N—($R_1$-substituted)-8-amino-3H-dibenzo[deh]isoquinoline-1,3 (2H)-dione) optionally having m substituents $R_3$ and/or n substituents $R_4$ and/or q substituents $R_5$) with an R'-contain-ing reagent being able to react with the 11-amino or 8-amino group of the azonafide derivative; said R'-containing reagent should not substantially react, under the selected reaction conditions, with other substituents (such as $R_3$, $R_4$ and $R_5$) that may optionally be present on the dibenzisoquinolinedi-one ring. Based on the following information and the general knowledge in organic chemistry, the skilled person knows how to select appropriate reagents and appropriate reaction conditions for this purpose. Suitable but non exhaustive examples of such reagents include the following:

R'-containing acyl halides or thioacyl halides, preferably R'-containing acyl chlorides or thioacyl chlorides wherein R' is a radical selected from the group consist-ing of $C_{2-7}$ alkylcarbonyl, alkenylcarbonyl, alkynylcar-bonyl, arylcarbonyl, alkyloxycarbonyl, aryloxycarbo-nyl, aryloxyalkylcarbonyl, cycloalkylcarbonyl, arylalkylcarbonyl, $Het^1$-carbonyl, $Het^1$alkylcarbonyl, $Het^1$oxycarbonyl, $Het^1$alkyloxycarbonyl, alkylthio-car-bonyl, alkenylthiocarbonyl, alkynylthiocarbonyl, arylthiocarbonyl, arylalkylthio-carbonyl, alkyloxythio-carbonyl, aryloxythiocarbonyl, alkyloxyalkylthiocarbo-nyl, aryloxyalkyl-thiocarbonyl, $Het^1$carbonyl, $Het^1$alkylthio-carbonyl, $Het^1$oxythiocarbonyl and $Het^1$alkyloxythiocarbonyl, wherein one or more carbon atoms of said radical are optionally substituted by one or more substituents independently selected from the group consisting of oxo, alkyl, cycloalkyl, alkyloxycar-bonyl, carboxyl, aminocarbonyl, mono- or di(alkyl)ami-nocarbonyl, aminosulfonyl, alkylS(=O)$_t$, hydroxy, cyano, halogen, amino, haloalkyl, alkoxy, haloalkoxy, nitro, monoalkyl- and dialkyl-amino; benzoyl chlorides suitable for use in the synthesis of the compounds of the present invention include, but are not limited to, benzoyl chloride, p-anisoyl-chloride, 2-bromobenzoyl chloride, 4-bromobenzoyl chloride, 3-chlorobenzoyl chloride, pentafluorobenzoyl chloride, 2-chlorobenzoyl chloride, p-toluoyl chloride, 4-chlorobenzoyl chloride, 2,4-dichlorobenzoyl chloride, 3,4-dichlorobenzoyl chlo-ride, 4-nitrobenzoyl chloride, 4-fluorobenzoyl chloride, 2-fluoro-benzoyl chloride, o-toluoyl chloride, m-toluoyl chloride, 4-cyanobenzoyl chloride, 3-nitrobenzoyl chlo-ride, 4-tert-butyl-benzoyl chloride, 4-biphenylcarbonyl chloride, 3,5-dimethoxybenzoyl chloride, 3-fluoroben-zoyl chloride, 2,6-dichlorobenzoyl chloride, 4-butyl-benzoyl chloride, 4-heptyloxybenzoyl chloride, 4-hexy-lbenzoyl chloride, 4-hexyloxybenzoyl chloride, 4-pentylbenzoyl chloride, m-anisoyl chloride, 2,6-dif-luoro-benzoyl chloride, 2-nitrobenzoyl chloride, 4-chloro-3-nitrobenzoylchloride, 3,4-difluoro-benzoyl chloride, 2-iodobenzoyl chloride, 1-naphthoyl chloride, o-anisoyl chloride, 2,4-difluorobenzoyl chloride, 4-(tri-fluoromethyl)benzoyl chloride, m-anisoyl chloride, 2,6-difluorobenzoyl chloride, 2-nitrobenzoyl chloride, 4-chloro-3-nitro-benzoylchloride, 3,4-difluorobenzoyl chloride, 2-iodobenzoyl chloride, 1-naphthoyl chloride, o-anisoyl chloride, 2,4-difluorobenzoyl chloride, 4-(tri-fluoromethyl)benzoyl chloride, 3-(chloro-methyl)-ben-zoyl chloride, 4-(chloromethyl)-benzoyl chloride, 3-(dichloromethyl)-benzoyl chloride, 2,3,4,5-tetrafluo-robenzoyl chloride, 2,4,6-trichlorobenzoyl chloride, 2,3,4-trifluorobenzoyl chloride, 2,4,6-trifluorobenzoyl chloride, 4-bromo-2-fluoro-benzoyl chloride, 2,3,5,6-tetrafluorobenzoyl chloride, 3,5-dinitrobenzoyl chlo-ride, 4-heptylbenzoyl chloride, 4-iodobenzoyl chloride, 4-octylbenzoyl chloride, 4-pentyl-oxybenzoyl chloride, 4-phenylazobenzoyl chloride, 4-propylbenzoyl chlo-ride, methyl 4-chloro-carbonylbenzoate, 3,5-dichlo-robenzoyl chloride, 3-fluoro-4-trifluoromethyl-benzoyl chloride, 2,6-dimethoxybenzoyl chloride, piperonyloyl chloride, 2,4-dimethoxybenzoyl chloride, 3,4-dihydro-2H-1,5-benzodioxepine-6-carbonyl chloride, 2,3-dihy-dro-1,4-benzodioxine-6-carbonyl chloride, 2,3-dihy-dro-1,4-benzodioxine-5-carbonyl chloride, 1-benzofuran-5-carbonyl chloride, 2,1,3-benzothiadia-zole-4-carbonyl chloride, 2,1,3-benzothiadiazole-5-car-bonyl chloride, 1,2,3-benzothia-diazole-5-carbonyl chloride, 2,1,3-benzoxadiazole-5-carbonyl chloride, 6-quinoxaline-carbonyl chloride, 4-(2-thienyl)-benzoyl chloride, 4-methyl-3,4-dihydro-2H-1,4-benzoxazine-7-carbonyl chloride, 4-(1,2,3-thiadiazol-4-yl)benzoyl chloride, 4-(1H-pyrazol-1-yl)benzoyl chloride, 1-me-thyl-1H-1,2,3-benzotriazole-5-carbonyl chloride, 1-benzothiophene-5-carbonyl chloride, 2,2-dimethyl-2, 3-dihydro-1-benzofuran-7-carbonyl chloride, 4-[(dipropyl-amino)sulfonyl]benzene-1-carbonyl chloride, 4-[3-(trifluoromethyl)-1H-pyrazol-1-yl]-benzoyl chloride, 2-bromo-5-methoxybenzene-1-carbonyl chloride, 5-bromo-2,3,4-trimethylbenzoyl chloride, 2-chloro-6-fluorobenzene-1-carbonyl chloride, 2,3-dimethylbenzene-1-carbonyl chloride, 3,4-dimethylbenzene-1-carbonyl chloride, 2-chloro-4-fluorobenzoyl chloride, 5,5,8,8-tetramethyl-5,6,7,8-tetrahydro-2-naphthalene-carbonyl chloride, 2-(4-methoxyphenoxy)-5-nitrobenzene-1-carbonyl chloride, 2,3-difluorobenzoyl chloride, 2-fluoro-5-(trifluoromethyl)benzoyl chloride, 2,3,6-trifluoro-benzoyl chloride, 1-isopropyl-1H-1,2,3-benzotriazole-5-carbonyl chloride, 1-isopropyl-1H-1,2,3-benzotriazole-5-carbonyl chloride, 3-fluoro-4-methylbenzoyl chloride, 3-(cyclopentyloxy)-4-methoxybenzoyl chloride, 4-fluoro-3-(trifluoromethyl)benzoyl chloride, 2,3-dihydro-1-benzofuran-7-carbonyl chloride, 3-(2-methyl-thiazol-4-yl)-benzoyl chloride, 1-isopropyl-2-(trifluoromethyl)-1H-benzimida-zole-5-carbonyl chloride, 5-bromo-2,3-dihydrobenzo[b]furan-7-carbonyl chloride, 2,4,6-trimethylbenzoyl chloride, 2-(2-thienyl)benzoyl chloride, 3-cyanobenzoyl chloride, acetylsalicyloyl chloride, 3-(5-methyl-1,2,4-oxadiazol-3-yl)-benzoyl chloride, and 4-(5-methyl-1,2,4-oxadiazol-3-yl)-benzoyl chloride. According to a particular embodiment, the benzoyl chloride reagent may be selected from the group consisting of 2-fluorobenzoyl chloride, 4-ethylbenzoyl chloride, 4-butylbenzoyl chloride, 4-methoxybenzoyl chloride, piperonyloyl chloride, 4-hexyl-benzoyl chloride, 3-chlorobenzoyl chloride, 4-fluorobenzoyl chloride, p-toluoyl chloride, 3-fluorobenzoyl chloride, 4-chlorobenzoyl chloride, benzoyl chloride, 4-tert-butylbenzoyl chloride, 4-biphenylcarbonyl chloride, o-anisoyl chloride, 1-naphthoyl chloride, 2-naphthoyl chloride, 4-pentylbenzoyl chloride, 4-bromobenzoyl chloride, 2,4-dimethoxybenzoyl chloride, 3,5-dichlorobenzoyl chloride, 3-bromobenzoyl chloride, 2-bromobenzoyl chloride 3-trifluoromethylbenzoyl chloride, 4-trifluoro-methylbenzoyl chloride and 2-ethylbenzoyl chloride. Numerous other carbonyl chlorides are known to the person skilled in the art and commercially available for use as acylating reagent for use in this invention including, but not limited to, cinnamoyl chloride, hydrocinnamoyl chloride, 2-phenylbutyryl chloride, phenylacetyl chloride 4-methoxyphenylacetyl chloride, 2-(2-naphthyl)acetyl chloride, 2-(3,5-difluorophenyl)ethanoyl chloride, 2-(1-naphthyl)ethanoyl chloride, 4-chlorophenylacetyl chloride, 3-methoxyphenylacetyl chloride, and 4-fluorophenylacetyl chloride;

R'-containing monoisocyanates and isothiocyanates wherein R' is a radical selected from the group consisting of alkylaminocarbonyl, alkenylaminocarbonyl, alkynylaminocarbonyl, arylaminocarbonyl, alkyloxyaminocarbonyl, aryloxyaminocarbonyl, aryloxyalkylaminocarbonyl, cycloalkylaminocarbonyl, arylalkylaminocarbonyl, Het[1]-aminocarbonyl, Het[1]alkylaminocarbonyl, Het[1]oxyalkylaminocarbonyl, Het[1]alkyloxyalkylaminocarbonyl, alkylaminothiocarbonyl, alkenylthioaminocarbonyl, alkynylaminothiocarbonyl, arylaminothiocarbonyl, arylalkylthioaminocarbonyl, alkyloxyalkylamino-thiocarbonyl, aryloxyalkylaminothiocarbonyl, Het[1]alkylthioaminocarbonyl, Het[1]oxyalkylaminothiocarbonyl and Het[1]alkyloxyalkylaminothiocarbonyl, wherein one or more carbon atoms of said radical is (are) optionally substituted by one or more substituents independently selected from the group consisting of oxo, alkyl, cycloalkyl, alkyloxycarbonyl, carboxyl, aminocarbonyl, mono- or di(alkyl)aminocarbonyl, aminosulfonyl, alkylS($=$O)$_r$, hydroxy, cyano, halogen, amino, haloalkyl, alkoxy, haloalkoxy, nitro, monoalkyl- and dialkyl-amino; aryl isocyanates suitable for use in the synthesis of compounds of the present invention with structural formulae (I) or (II) include, but are not limited to, 4-fluorophenyl isocyanate, phenyl isocyanate, m-tolyl isocyanate, p-tolyl isocyanate, 4-chlorophenyl isocyanate, ethyl 4-isocyanatobenzoate, 2-fluorophenyl isocyanate, 3-fluorophenyl isocyanate, $\alpha,\alpha,\alpha$-trifluoro-o-tolyl isocyanate, tolylene-2,4-diisocyanate, tolylene 2,6-diisocyanate, 4-methoxyphenyl isocyanate, 4-bromophenyl isocyanate, 2-methoxy-phenyl isocyanate, 3-Methoxyphenyl isocyanate, 2,4-dichlorophenyl isocyanate, o-tolyl isocyanate, 3,4-dichlorophenyl isocyanate, 2-nitrophenyl isocyanate, 4-nitrophenyl isocyanate, 2,4-difluorophenyl isocyanate, 2-bromophenyl isocyanate, 2,6-difluoro-phenyl isocyanate, 2-(trifluoromethoxy)phenyl isocyanate, 2-chloro-5-(trifluoromethyl)phenyl isocyanate, 4-chloro-2-(trifluoromethyl) phenyl isocyanate, 4-chloro-3-(trifluoromethyl)phenyl isocyanate, 2,5-difluorophenyl isocyanate, 4-(trifluoromethoxy)phenyl isocyanate, 2-ethoxyphenyl isocyanate, 4-ethoxyphenyl isocyanate, 4-isopropylphenyl isocyanate, 3-acetylphenyl isocyanate, 2,6-diisopropylphenyl isocyanate, 3-bromophenyl isocyanate, 3,5-dichlorophenyl isocyanate, 4-fluoro-3-nitrophenyl isocyanate, 3,5-dimethylphenyl isocyanate, 3,5-bis(trifluoromethyl)phenyl isocyanate, 3-cyanophenyl isocyanate, 4-(methylthio)phenyl isocyanate, 2-ethylphenyl isocyanate, 2,6-dimethyl-phenyl isocyanate, $\alpha,\alpha,\alpha$-trifluoro-p-tolyl isocyanate, 2,3-dichlorophenyl isocyanate, 4-methyl-3-nitrophenyl isocyanate, 2,4-dimethoxyphenyl isocyanate, 4-(chloromethyl)phenyl isocyanate, 4-bromo-2-chlorophenyl isocyanate, 2-bromo-4,6-difluoro-phenyl isocyanate, 4-bromo-2-fluorophenyl isocyanate, 4-(dimethylamino)phenyl isocyanate, 2-fluoro-5-methylphenyl isocyanate, 4-fluoro-2-nitrophenyl isocyanate, 2-fluoro-3-(trifluoromethyl) phenyl isocyanate, 2-fluoro-5-(trifluoromethyl)phenyl isocyanate, 2-fluoro-6-(trifluoromethyl)-phenyl isocyanate, 4-fluoro-2-(trifluoromethyl)phenyl isocyanate, 4-fluoro-3-(trifluoromethyl)phenyl isocyanate, 4-(heptyloxy)phenyl isocyanate, 2-iodophenyl isocyanate, 2-naphthyl isocyanate, 2-n-propylphenyl isocyanate, 4-(trifluoromethyl-thio)phenyl isocyanate, 2,3,4-trifluorophenyl isocyanate, 2,6-dichlorophenyl isocyanate, 3-nitrophenyl isocyanate, 3-chlorophenyl isocyanate, 2-chlorophenyl isocyanate, 1-naphthyl isocyanate, 2,3-dimethylphenyl isocyanate, 3-chloro-4-fluorophenyl isocyanate, 2,5-dimethylphenyl isocyanate, 3,4-difluorophenyl isocyanate, 2,3-dihydro-1-benzofuran-5-yl isocyanate, 2,3-dihydro-1,4-benzodioxin-6-yl isocyanate, 6-fluoro-4H-1,3-benzodioxin-8-yl isocyanate, 2,1,3-benzothiadiazol-4-yl isocyanate, 3,4-dihydro-2H-1,5-benzodioxepin-7-yl isocyanate, 3-(cyclopentyloxy)-4-methoxyphenyl isocyanate, 2-(methylthio)phenyl isocyanate, 2-(tert-butyl)phenyl isocyanate, 4-(tert-butyl)phenyl isocyanate, 3-chloro-2-methylphenyl isocyanate, 4-butyl-2-methylphenyl isocyanate, 2-ethyl-6-methylphenyl isocyanate, 4-chloro-3-nitrophenyl isocyanate, 4-bromo-2-methylphenyl isocyanate, 3-(methylthio)phenyl isocyanate, 5,5,8,8-tetramethyl- 5,6,7,8-tetrahydro-2-naphthalenyl isocyanate, 5-fluoro-2-methylphenyl isocyanate, 4-phenoxyphenyl isocyanate, 4-methoxy-2-methyl-phenyl isocyanate, α,α,α-trifluoro-m-tolyl isocyanate, 2,6-dibromo-4-isopropylphenyl isocyanate, 2,6-dimethoxyphenyl isocyanate, 2-(4-isocyanatophenyl)thiophene, 4-(3-isocyanatophenyl)-2-methyl-1,3-thiazole, 3-(3-isocyanatophenyl)-5-methyl-1,2,4-oxa-diazole, 1-benzothiophen-5-yl isocyanate, 1-(3-isocyanatophenyl)-1H-pyrrole, 1-(4-isocyanatophenyl)-1H-pyrrole, 3,5-dimethoxyphenyl isocyanate and 2,4,6-trichloro-phenyl isocyanate; aryl isothiocyanates suitable for use in the synthesis of the compounds of the present invention include, but are not limited to, phenyl isothiocyanate, 4-fluorophenyl isothiocyanate, methyl 2-isocyanatobenzoate, 2-chlorophenyl isothiocyanate, 3-chlorophenyl isothiocyanate, o-tolyl isothiocyanate, m-tolyl isothiocyanate, p-tolyl isothiocyanate, 2-methoxyphenyl isothiocyanate, 2-bromophenyl isothiocyanate, 3-bromophenyl isothiocyanate, 2,4-dichloro-phenyl isothiocyanate, 2-fluoro phenylisothiocyanate, 4-methoxyphenyl isothiocyanate, α,α,α-trifluoro-m-tolyl isothiocyanate, 3-fluorophenyl isothiocyanate, 3,5-bis(trifluoromethyl)phenyl isothiocyanate, 1-naphthyl isothiocyanate, 4-dimethylamino-1-naphthyl isothiocyanate, 4-(methylthio)phenyl isothiocyanate, 2-methoxy-5-methylphenyl isothiocyanate, 4-cyanophenyl isothiocyanate, 3-chloro-4-fluorophenyl isothiocyanate, 4-nitrophenyl isothiocyanate, 4-bromophenyl isothiocyanate, 2,3-dihydro-1,4-benzodioxin-6-yl isothiocyanate, 1,3-benzodioxol-5-yl isothiocyanate, 4-(1H-pyrazol-1-yl)phenyl isothiocyanate, 2-(trifluoromethyl) phenyl isothiocyanate, 2,3-dimethylphenyl isothiocyanate, 2-isopropyl phenyl isothiocyanate, 4-iso-propylphenyl isothiocyanate, 5-chloro-2-methoxyphenyl isothiocyanate, 2,4-dimethoxyphenyl isothiocyanate, 2,4-dichloro-6-methylphenyl isothiocyanate, 2-bromo-4-isopropylphenyl isothiocyanate, 5-chloro-2-fluorophenyl isothiocyanate, 4-(trifluoromethoxy)phenyl isothiocyanate, 3,5-dimethylphenyl isothiocyanate, 3,5-dimethoxyphenyl isothiocyanate, 4-chlorophenyl isothiocyanate, 3,4-dimethoxyphenyl isothiocyanate, 2,6-dimethylphenyl isothiocyanate, 3-methoxyphenyl isothiocyanate, mesityl isothiocyanate, 4-(benzyloxy)phenyl isothiocyanate, 2,4-dimethylphenyl isothiocyanate, 2-bromo-5-fluorophenyl isothiocyanate, 5-fluoro-2-methylphenyl isothiocyanate, 4-chloro-2,5-dimethoxyphenyl isothiocyanate, 2,5-dichlorophenyl isothiocyanate, 2-(tert-butyl)-4,5,6-trimethyl-3-nitrophenyl isothiocyanate, 2-isopropyl-6-methylphenyl isothiocyanate, 4-ethoxyphenyl isothiocyanate, 5-chloro-2-methylphenyl isothiocyanate, 2-ethyl-6-methylphenyl isothiocyanate and 4-(trifluoromethyl)phenyl isothiocyanate.

R'-containing halogenoalkanes (preferably monohalogenoalkanes R'X wherein X is halogen (preferably iodine, bromine or chlorine) and R' is $C_{1-12}$ alkyl optionally substituted with aryl, for instance monoiodoalkanes such as methyl iodide and ethyl iodide, monobromoalkanes such as methyl bromide, ethyl bromide and benzylbromide, and monochloroalkanes such as benzyl chloride), R'-containing halogenoalkenes (preferably monohalogenoalkenes including a $C_{2-12}$ alkenyl group, for instance monoiodoalkenes such as allyl iodide, monobromoalkenes such as allyl bromide, and, monochloroalkenes such as allyl chloride), and R'-containing halogenoalkynes (preferably monohalogenoalkynes including a $C_{2-12}$ alkynyl group, more preferably monoiodoalkynes (e.g. propargyl iodide);

R'-containing anhydrides such as, but not limited to, acetic anhydride, trifluoroacetic anhydride, succinic anhydride, phthalic anhydride, hexahydrophthalic anhydride, maleic anhydride, bromomaleic anhydride, linoleic anhydride, pivaloyl anhydride, 5-chloroisatoic anhydride, aconitic anhydride, benzoic anhydride and the like; and R'-containing sulfonyl halides, in particular sulfonyl chlorides, preferably halides selected from the group consisting of $C_{2-7}$ alkylsulfonyl, alkenylsulfonyl, alkynylsulfonyl, arylsulfonyl, aryloxyalkylsulfonyl, cycloalkylsulfonyl, arylalkylsulfonyl, Het$^1$-sulfonyl and Het$^1$alkylsulfonyl, wherein one or more carbon atoms of said radical are optionally substituted by one or more substituents independently selected from the group consisting of oxo, alkyl, cycloalkyl, alkyloxycarbonyl, carboxyl, aminocarbonyl, mono- or di(alkyl)aminocarbonyl, aminosulfonyl, alkylS(=O)$_p$, hydroxy, cyano, halogen, amino, haloalkyl, alkoxy, haloalkoxy, nitro, monoalkyl- and dialkyl-amino; aylsulfonyl chlorides suitable for use in the synthesis of the compounds of the present invention include, but are not limited to, 4-fluorobenzenesulfonyl chloride, 2-mesitylenesulfonyl chloride, 4-methoxybenzene-sulfonyl chloride, p-toluenesulfonyl chloride, pentafluorobenzene-sulfonyl chloride, benzenesulfonyl chloride, 4-bromobenzenesulfonyl chloride, N-acetylsulfanilyl chloride, 2,4,6-triisopropyl-benzenesulfonyl chloride 2-naphthalenesulfonylchloride, 4-chloro-benzenesulfonyl chloride 3,5-dichloro-2-hydroxy-benzenesulfonylchloride, 2,5-dichloro-benzenesulfonyl chloride, pipsyl chloride, 1-naphthalenesulfonylchloride, methyl 2-(chlorosulfonyl)-benzoate, 4-tert-butylbenzene-sulfonyl chloride, 3-(trifluoromethyl)benzenesulfonyl chloride, 2-bromobenzenesulfonyl chloride, 4-acetylbenzene-sulfonylchloride, 2-(trifluoromethyl)-benzenesulfonyl chloride, 3,4-dichlorobenzene-sulfonyl chloride, 3,4-dimethoxybenzenesulfonyl chloride, 3-chlorobenzenesulfonyl chloride, 2-chloro-4-fluorobenzenesulfonyl chloride, 3,5-dichlorobenzenesulfonyl chloride, 3-chloro-4-fluorobenzenesulfonyl chloride, 2,4-dichlorobenzenesulfonyl chloride, 2,5-dimethoxybenzenesulfonyl chloride, 3-bromo-benzenesulfonyl chloride, 2,3-dichlorobenzenesulfonyl chloride, 5-fluoro-2-methylbenzenesulfonyl chloride, 3-fluorobenzenesulfonyl chloride, 2,3,5,6-tetramethyl-benzenesulfonyl chloride, 3-chloro-2-methylbenzenesulfonyl chloride, 2,5-dibromo-3,6-difluoro-benzenesulfonyl chloride, 2,6-difluorobenzene-sulfonyl chloride, 2-chloro-benzenesulfonyl chloride, 5-bromo-2-methoxybenzenesulfonyl chloride, 5-chloro-2-methoxybenzenesulfonyl chloride, 2,4-difluorobenzene-sulfonyl chloride, 2-cyano-benzenesulfonyl chloride, 2-chloro-5-(trifluoromethyl)-benzenesulfonyl chloride, 4-bromomethylbenzenesulfonyl chloride, 2,4-dimethoxybenzenesulfonyl chloride, 4-chloro-3-nitrobenzenesulfonyl chloride, 4-(chlorosulfonyl)-benzoic acid, 3-nitro-benzenesulfonyl chloride, 4-nitrobenzenesulfonyl chloride, 2-(methylsulfonyl)-benzenesulfonyl chloride, 4-(methylsulfonyl)-benzene-sulfonyl chloride, 3-(chloro-sulfonyl)-benzoic acid, 2,4-dichloro-5-methylbenzene-sulfonyl chloride, 4-(trifluoro-methoxy)-benzenesulfonyl chloride, 2-methoxy-4-nitrobenzenesulfonyl chloride, 4-bromo-2-chlorobenzenesulfonyl chloride, 2,3-dihydro-1-benzofuran-5-sulfonyl chloride, 2,3-dihydro-1,4-benzodioxine-6-sulfonyl chloride, 1,3-benzothiazole-6-sulfonyl chloride, 1,3-benzothiadiazole 4 sulfonyl chloride, 2,1,3-benzothiadiazole-5-sulfonyl chloride, 2,1,3-benzoxadiazole-4-sulfonyl chloride, 3,4-dihydro-2H-1,5-benzodioxepine-7-sulfonyl chloride, 4-methyl-3,4-dihydro-2H-1,4-benzoxazine-7-sulfonyl chloride, 4-(1,3-oxazol-5-yl)benzenesulfonyl chloride, 4-(1,2,3-thiadiazol-4-yl)benzenesulfonyl chloride, 4-(1H-pyrazol-1-yl) benzenesulfonyl chloride, 4-(3-chloro-2-cyanophenoxy) benzene-1-sulfonyl chloride, 5-chlorosulfonyl-2-hydroxybenzoic acid, 4-bromo-2,5-difluoro-benzene-1-sulfonyl chloride, 4-(acetylamino)-3-chloro-benzene-1-sulfonyl chloride, 3,5-di-(trifluoromethyl)-benzene-1-sulfonyl chloride, 2-fluorobenzenesulfonyl chloride, 4-methyl-3-nitrobenzene-1-sulfonyl chloride, 5-chloro-2,1,3-benzoxadiazole-4-sulfonyl chloride, 3-(5-methyl-1,3,4-oxadiazol-2-yl) benzenesulfonyl chloride, methyl 3-(chlorosulfonyl)-4-methoxybenzoate, 4-bromo-2-(trifluoromethyl)-benzenesulfonyl chloride, 2,2-dimethyl-6-chromanesulfonyl chloride, 4-(morpholine-4-sulfonyl)benzenesulfonyl chloride, 4-(pyrrolidine-1-sulfonyl)-benzene-sulfonyl chloride, 3-(2-methyl-4-pyrimidinyl)benzenesulfonyl chloride, 2-cyano-5-methylbenzenesulfonyl chloride, 2,5-dimethylbenzenesulfonyl chloride, 4-chloro-3-(trifluoromethyl)-benzenesulfonyl chloride, 4-bromo-2-methylbenzene-1-sulfonyl chloride, 2-chloro-4-(trifluoro-methyl)-benzene-1-sulfonyl chloride, 2-chloro-4-cyano-benzene-1-sulfonyl chloride, 2,6-dichloro-4-(trifluoromethyl)-benzene-1-sulfonyl chloride, 3,4-difluorobenzene-1-sulfonyl chloride, 2-iodobenzene-1-sulfonyl chloride, 4-methyl-1-naphthalenesulfonyl chloride, 4-(trifluoromethyl)benzene-1-sulfonyl chloride, 2,6-dichlorobenzene-1-sulfonyl chloride, 2-(trifluoromethoxy)benzene-1-sulfonyl chloride, 4-cyanobenzene-1-sulfonyl chloride, 4-butoxybenzene-1-sulfonyl chloride, 2,3, 4-trifluorobenzene-1-sulfonyl chloride, 4-bromo-2-(trifluoromethoxy)benzene-1-sulfonyl chloride, 3-cyanobenzene-1-sulfonyl chloride, 3-chloro-4-methylbenzene-1-sulfonyl chloride, 4-bromo-2-ethyl-benzene-1-sulfonyl chloride, 5,5,8,8-tetramethyl-5,6,7,8-tetrahydro-2-naphthalene-sulfonyl chloride, 4-(2-chloro-6-nitrophenoxy) benzene-1-sulfonyl chloride, 3,5-dichloro-4-(2-chloro-4-nitrophenoxy)benzene-1-sulfonyl chloride, 4-pentylbenzene-1-sulfonyl chloride, 4-ethylbenzene-1-sulfonyl chloride, 4-propylbenzene-1-sulfonyl chloride, 4-butylbenzene-1-sulfonyl chloride, 3-toluenesulfonyl chloride, 4-isopropyl-benzenesulfonyl chloride, 4-(2-oxo-1-pyrrolidinyl)benzene sulfonyl chloride, 4-(2-methoxyphenoxy)benzenesulfonyl chloride, 4-(2-chloro-phenoxy)benzenesulfonyl chloride, 4-(2-methylphenoxy)benzenesulfonyl chloride, 4'-chloro(1,1'-biphenyl)-4-sulfonyl chloride, 4'-fluoro(1,1'-biphenyl)-4-sulfonyl chloride, 4'-methoxy-(1,1'-biphenyl)-4-sulfonyl chloride, 3',4'-dichloro-(1,1'-biphenyl)-4-sulfonyl chloride, 4-phenoxybenzenesulfonyl chloride, 4'-methyl-(1, 1'-biphenyl)-4-sulfonyl chloride, 5-bromo-2,3-dihydrobenzo [b]furan-7-sulphonyl chloride, 3,4,5-trifluoro-benzenesulfonyl chloride, 3-(5-methyl-1,2,4-oxadiazol-3-yl) benzenesulfonyl chloride, 4-(2-methyl-1,3-thiazol-4-yl) benzenesulfonyl chloride, 1-acetyl-5-indolinesulfonyl chloride, 3-(2-methyl-1,3-thiazol-4-yl)benzene-sulfonyl chloride and 1,3-benzodioxole-5-sulfonyl chloride.

Such reaction may be performed in any suitable solvent system for both reagents such as but not limited to acetonitrile, aromatic solvents (e.g. toluene) or halogenated solvents (e.g. dichloromethane) or even in special circumstances by using said reagent as the solvent. The skilled person will be able to readily determine the more appropriate type of solvent as well as the more appropriate concentration of reactants in said solvent in order to keep reaction control and to achieve the desired reaction product in the more expedient way. Reaction may usually be effected at moderate temperatures (i.e. between about 15° C. and about 45° C.), although the reaction rate may be increased by heating up to the boiling temperature of the solvent. Reaction is preferably carried out by using an at least stoechiometric amount, for instance a molar ratio in the range from about 1.1 to about 3.0, of the R'-containing reagent with respect to the benzisoquinolinedione derivative. When the R'-containing reagent is an halogenoalkane, halogenoalkene, or halogenoalkyne, it may be preferred to use a stoechiometric amount thereof in order to avoid the presence of by-products.

In another aspect, the invention relates to a method of making a substituted azonafide derivatives represented by one of the formulae (III) or (IV) wherein each of m, n, q, $R_1$, $R_3$, R', $R_4$ and $R_5$ are as broadly defined hereinabove, by reacting an azonafide optionally having m substituents $R_3$ and/or n substituents $R_4$ and/or q substituents $R_5$ with an aldehyde having the formula R'CH(O). Said aldehyde may be formaldehyde or may be saturated aliphatic (e.g. acetaldehyde, propionaldehyde, butyraldehyde, 4-aminobutyraldehyde optionally protected in its diacetal form, 2-ethylbutyraldehyde, malonaldehyde, α-fluoromalonaldehyde, 2-chloromalonaldehyde, bromomalonaldehyde or valeraldehyde), ethylenically unsaturated aliphatic (e.g. acrolein, allyl aldehyde and crotonaldehyde), acetylenically unsaturated aliphatic (e.g. propargylaldehyde, optionally protected in its diacetal form), cycloaliphatic (e.g. cyclohexanecarboxaldehyde, cyclooctanecarboxaldehyde), ethylenically unsaturated cycloaliphatic (e.g. 3-cyclohexene-1-carboxaldehyde), arylalkyl (e.g. 3-phenylbutyraldehyde and hydrocinnamaldehyde), arylalkenyl (e.g. cinnamaldehyde), arylalkynyl (e.g. phenylpropargyl aldehyde), aromatic (e.g. benzaldehyde and substituted derivatives thereof such as, but not limited to, salicylaldehyde, o-tolualdehyde, m-tolualdehyde, p-tolualdehyde, anisaldehyde, 2,5-dihydroxybenzaldehyde, 4-propoxybenzaldehyde, 4-phenoxy-benzaldehyde, 3-(3,4-dichlorophenoxy)benzaldehyde, 3-(3,5-dichlorophenoxy) benzaldehyde, 2-bromobenzaldehyde, 3-bromobenzaldehyde, 4-bromo-benzaldehyde, 2-chlorobenzaldehyde, 3-chlorobenzaldehyde, 4-chlorobenzaldehyde, 2-fluorobenzaldehyde, 3-fluorobenzaldehyde, 4-fluorobenzaldehyde, 2,3-dichlorobenzaldehyde, 2,4-dichlorobenzaldehyde, 2,6-dichlorobenzaldehyde, 3,4-dichlorobenzaldehyde, 3,5-dichlorobenzaldehyde, 2,3-difluorobenzaldehyde, 2,4-difluorobenzaldehyde, 2,5-difluorobenzaldehyde, 2,6-difluorobenzaldehyde, 3,4-difluorobenzaldehyde, 3,5-difluorobenzaldehyde, 2,3,4-trifluorobenzaldehyde, 2-(trifluoromethyl)benzaldehyde, 3-(trifluoromethyl)benzaldehyde, 4-(trifluoromethyl)benzaldehyde, 3-(trifluoromethoxy)benzaldehyde, 5-(trifluoromethoxy)salicylaldehyde, 3,5-dichlorosalicylaldehyde, 2-amino-benzaldehyde, 2-nitrobenzaldehyde, 3-nitrobenzaldehyde, 4-nitrobenzaldehyde, 3-cyanobenzaldehyde, 4-cyanobenzaldehyde, 4-dimethylamino-1-naphthaldehyde, 4-(dimethylamino)benzaldehyde, 4-(diethylamino)benzaldehyde, 9-anthraldehyde, 3,4,5-trimethoxybenzaldehyde, 1-naphthaldehyde and 2-naphthaldehyde), saturated or partly unsaturated or fully unsaturated heterocyclic (e.g. pyrrole-2-carboxaldehyde, 2-thiophene-carboxaldehyde, 3-thiophenecarboxaldehyde, pyrrolidine-carboxaldehyde, 4-pyridinecarboxaldehyde, 3-pyridinecarboxaldehyde and piperonal) or mixed (e.g. phenylacetaldehyde or 2-phenylpropionaldehyde).

Such reaction involving an aldehyde may be performed in any suitable solvent system for both reagents such as, but not limited to, aromatic solvents like benzene or toluene. The skilled person will be able to readily determine the more appropriate concentration of reactants in said solvent in order to keep reaction control and to achieve the desired reaction product in the more expedient way. Reaction may usually be effected at the solvent boiling temperature (e.g. between about 80° C. and about 110° C.). Reaction is preferably carried out by using an at least stoechiometric amount, for instance a molar ratio in the range from about 1.1 to about 3.0, of the aldehyde with respect to the azonafide derivative.

The present invention further provides the use of a substituted azonafide derivative represented by the formula (I), (II), (III) or (IV), or a pharmaceutically acceptable salt or a solvate thereof, as a biologically-active ingredient, i.e. an active principle, especially as a medicine or a diagnostic agent or for the manufacture of a medicament or a diagnostic kit. In particular the said medicament may be for the prevention or treatment of a pathologic condition selected from the group consisting of cell proliferative disorders.

The compounds according to this invention are active against several types of cancers, which implies that they may be used in various medical applications. The compounds according to the invention also exhibit anti-migratory effect on cancer cells (as illustrated in example 73 provided below). The compounds according to the invention have the ability to stop the migration of cells away from the neoplastic tumour tissue and thus enable to reduce the colonization of new tissues by these cells. For instance when a malignant tumour has reached a certain size, tumour cells move away from the initial tumour site and start to migrate. The actin cytoskeleton, tubulin and adhesion molecules linking the constituents of extracellular matrix to intracellular actin cytoskeleton are central to locomotion. These elements represent new potential therapeutic targets in the field of cancer therapy.

Due to these interesting properties, the compounds according to the invention are particularly suitable for use as a medicament in the treatment of diseases associated with cell proliferation and cell migration, and even in particular in the treatment of cancer. The term "diseases associated with cell proliferation and cell migration" as used herein refers to, but is not limited to, any type of cancer or condition involving cell proliferation and cell migration, including for example chronic inflammation and restenosis in cardiovascular disease. The compounds of the invention may be especially used in the treatment of cancers such as but not limited to leukaemia, non-small cell lung cancer, small cell lung cancer, CNS cancer, melanoma, ovarian cancer, renal cancer, prostate cancer, breast cancer, glioma, colon cancer, bladder cancer, sarcoma, pancreatic cancer, colorectal cancer, head and neck cancer, liver cancer and haematological cancer and lymphoma. In addition, the compounds according to the invention are also suitable in the treatment of scar tissue and wounds. Most compounds of the present invention can act as active ingredients in treating scar tissue and in promoting wound healing and tissue regeneration.

The present invention also relates to the use of the compounds according to the invention or to a pharmaceutical composition comprising said compounds in the treatment of cancer. A method of treating cancer comprises administering to an individual in need of such treatment a pharmaceutical composition comprising the compounds according to the invention. For this purpose, the pharmaceutical composition of the present invention may be administered orally, parenterally, i.e. including subcutaneous injections, intravenous, intramuscular, intrasternal injection or infusion techniques, by inhalation spray, or rectally, in dosage unit formulations containing conventional non-toxic pharmaceutically acceptable carriers, adjuvants and vehicles. In accordance with the method of the present invention, said pharmaceutical composition can be administered separately at different times during the course of therapy or concurrently in divided or single combination forms. The present invention is therefore to be understood as embracing all such regimes of simultaneous or alternating treatment and the term "administering" is to be interpreted accordingly.

Essentially, the primary modes of treatment of solid tumour cancers comprise surgery, radiation therapy and chemotherapy, separately and in combination. The compounds according to the invention are suitable for use in combination with these medicinal techniques. The compounds of the invention may be useful in increasing the sensitivity of tumour cells to radiation in radiotherapy and also in potentiating or enhancing damage to tumours by chemotherapeutic agents. The compounds and their pharmaceutically acceptable salts may also be useful for sensitising multidrug-resistant tumour cells. The compounds according to the invention are useful therapeutic compounds for administration in conjunction with other DNA-damaging cytotoxic drugs or radiation used in radiotherapy to potentiate their effect.

Therefore, due to their favorable pharmacological properties, the compounds according to this invention are particularly suitable for use as medicaments or in the preparation of medicaments and combined preparations for the treatment of patients suffering from diseases associated with cell proliferation, more especially for treating cancer.

The term "cell proliferative disorder" as used herein refers to, but is not limited to, any type of cancer or other pathologic condition involving cell proliferation such as leukemia, lung cancer, colorectal cancer, central nervous system (CNS) cancer, melanoma, ovarian cancer, kidney cancer, prostate cancer, breast cancer, glioma, bladder cancer, bone cancer, sarcoma, head and neck cancer, liver cancer, testicular cancer, pancreatic cancer, stomach cancer, oesophaegal cancer, bone marrow cancer, duodenum cancer, eye cancer (retinoblastoma) and lymphoma.

Any of the uses mentioned above may also be restricted to a non-medical use (e.g. in a cosmetic composition), a non-therapeutic use, a non-diagnostic use, a non-human use (e.g. in a veterinary composition), or exclusively an in-vitro use, or a use with cells remote from an animal.

The invention further relates to a pharmaceutical composition comprising:
(a) one or more substituted azonafide derivative represented by the formula (I), (II), (III) or (IV), and/or a pharmaceutically acceptable salt thereof and/or a solvate thereof, and
(b) one or more pharmaceutically acceptable carriers.

In another embodiment, this invention provides combined preparations, preferably synergistic combinations, of one or more azonafide derivative represented by the formulae (I), (II), (III) or (IV), and/or a pharmaceutically acceptable salt thereof and/or a solvate thereof, with one or more biologically-active drugs being preferably selected from the group consisting of antineoplastic drugs. As is conventional in the art, the evaluation of a synergistic effect in a drug combination may be made by analysing the quantification of the interactions between individual drugs, using the median effect principle described by Chou et al. in Adv. Enzyme Reg. (1984) 22:27. Briefly, this principle states that interactions (synergism, additivity, antagonism) between two drugs can be quantified using the combination index (hereinafter referred as CI) defined by the following equation:

$$CI_x = \frac{ED_x^{1c}}{ED_x^{1a}} + \frac{ED_x^{2c}}{ED_x^{2a}}$$

wherein $ED_x$ is the dose of the first or respectively second drug used alone (1a, 2a), or in combination with the second or respectively first drug (1c, 2c), which is needed to produce a given effect. The said first and second drug have synergistic or additive or antagonistic effects depending upon CI<1, CI=1, or CI>1, respectively. As will be explained in more detail herein-below, this principle may be applied to a number of desirable effects such as, but not limited to, an activity against cell proliferation.

The invention further relates to a composition or combined preparation having synergistic effects against cell proliferation and containing:
(a) one or more antineoplastic drugs, and
(b) at least one azonafide derivative represented by the general formula (I), (II), (III) or (IV), and/or a pharmaceutically acceptable salt thereof and/or a solvate thereof, and
(c) optionally one or more pharmaceutical excipients or pharmaceutically acceptable carriers, for simultaneous, separate or sequential use in the treatment or prevention of cell proliferative disorders.

Suitable antineoplastic drugs for inclusion into the synergistic antiproliferative pharmaceutical compositions or combined preparations of this invention are preferably selected from the group consisting of alkaloids, topoisomeraze inhibitors, alkylating agents (including but not limited to alkyl sulfonates, aziridines, ethylenimines, methylmelamines, nitrogen mustards and nitrosoureas), antibiotics, antimetabolites (including but not limited to folic acid analogs, purine analogs and pyrimidine analogs), enzymes, interferon and platinum complexes. More specific examples include acivicin; aclarubicin; acodazole; acronine; adozelesin; aldesleukin; altretamine; ambomycin; ametantrone; aminoglutethimide; amonafide and its derivatives, amsacrine; anastrozole; anthramycin; asparaginase; asperlin; azacitidine; azetepa; azotomycin; batimastat; benzodepa; bicalutamide; bisantrene; bisnafide; bizelesin; bleomycin; brequinar; bropirimine; busulfan; cactinomycin; calusterone; caracemide; carbetimer; carboplatin; carmustine; carubicin; carzelesin; cedefingol; chlorambucil; cirolemycin; cisplatin; cladribine; crisnatol; cyclophosphamide; cytarabine; dacarbazine; dactinomycin; daunorubicin; decitabine; dexormaplatin; dezaguanine; diaziquone; docetaxel; doxorubicin; droloxifene; dromostanolone; duazomycin; edatrexate; eflomithine; elsamitrucin; enloplatin; enpromate; epipropidine; epirubicin; erbulozole; esorubicin; estramustine; etanidazole; ethiodized oil I 131; etoposide; etoprine; fadrozole; fazarabine; fenretinide; floxuridine; fludarabine; fluorouracil; flurocitabine; fosquidone; fostriecin; gemcitabine; Gold 198; hydroxyurea; idarubicin; ifosfamide; ilmofosine; interferon α-2a; interferon α-2b; interferon α-n1; interferon α-n3; interferon β-1a; interferon γ-1b; iproplatin; irinotecan; lanreotide; letrozole; leuprolide; liarozole; lometrexol; lomustine; losoxantrone; masoprocol; maytansine; mechlorethamine; megestrol; melengestrol; melphalan; menogaril; mercaptopurine; methotrexate; metoprine; meturedepa; mitindomide; mitocarcin; mitocromin; mitogillin; mitomalcin; mitomycin; mitosper; mitotane; mitoxantrone; mycophenolic acid; nocodazole; nogala-mycin; ormaplatin; oxisuran; paclitaxel; pegaspargase; peliomycin; pentamustine; peplomycin; perfosfamide; pipobroman; piposulfan; piroxantrone; plicamycin; plomestane; porfimer; porfiromycin; prednimustine; procarbazine; puromycin; pyrazofurin; riboprine; rogletimide; safingol; semustine; simtrazene; sparfosate; sparsomycin; spirogermanium; spiromustine; spiroplatin; streptonigrin; streptozocin; strontium 89 chloride; sulofenur; talisomycin; taxane; taxoid; tecogalan; tegafur; teloxantrone; temoporfin; teniposide; teroxirone; testolactone; thiamiprine; thioguanine; thiotepa; tiazofurin; tirapazamine; topotecan; toremifene; trestolone; triciribine; trimetrexate; triptorelin; tubulozole; uracil mustard; uredepa; vapreotide; verteporfin; vinblastine; vincristine; vindesine; vinepidine; vinglycinate; vinleurosine; vinorelbine; vinrosidine; vinzolidine; vorozole; zeniplatin; zinostatin; zorubicin; and their pharmaceutically acceptable salts.

Other suitable anti-neoplastic compounds include 20-epi-1,25 dihydroxyvitamin $D_3$ and analogues thereof; 5-ethynyluracil; abiraterone; aclarubicin; acylfulvene; adecypenol; adozelesin; aldesleukin; ALL-TK antagonists; altretamine; ambamustine; amidox; amifostine; aminolevulinic acid; amrubicin; amsacrine; anagrelide; anastrozole; andrographolide; angiogenesis inhibitors; antagonist D; antagonist G; antarelix; anti-dorsalizing morphogenetic protein-1; anti-androgens such as, but not limited to, benorterone, cioteronel, cyproterone, delmadinone, oxendolone, topterone, zanoterone; anti-estrogens such as, but not limited to, clomethorone; delmadinone; nafoxidine; nitromifene; raloxifene; tamoxifen; toremifene; trioxifene and their pharmaceutically acceptable salts; antineoplaston; antisense oligonucleotides; aphidicolin glycinate; apoptosis gene modulators; apoptosis regulators; apurinic acid; ara-CDP-DL-PTBA; arginine deaminase; asulacrine; atamestane; atrimustine; axinastatin; azasetron; azatoxin; azatyrosine; baccatin III derivatives; balanol; batimastat; BCR/ABL antagonists; benzochlorins; benzoylstaurosporine; β-lactam derivatives; β-alethine; betaclamycin B; betulinic acid; bFGF inhibitor; bicalutamide; bisantrene; bisaziridinylspermine; bisnafide; bistratene A; bizelesin; breflate; bropirimine; budotitane; buthionine sulfoximine; calcipotriol; calphostin C; camptothecin derivatives; canarypox IL-2; capecitabine; carboxyamidotriazole; CaRest M3; CARN 700; cartilage derived inhibitor; carzelesin; casein kinase inhibitors; castanospermine; cecropin B; cetrorelix; chlorins; chloroquinoxaline sulfonamide; cicaprost; cis-porphyrin; clomifene and analogues thereof; clotrimazole; collismycin A and B; combretastatin and analogues thereof; conagenin; crambescidin 816; cryptophycin and derivatives thereof; curacin A; cyclopentanthraquinones; cycloplatam; cypemycin; cytarabine; cytolytic factor; cytostatin; dacliximab; dehydrodidemnin B; deslorelin; dexifosfamide; dexrazoxane; dexverapamil; didemnin B; didox; diethylnorspermine; dihydro-5-aza-cytidine; dihydrotaxol; dioxamycin; diphenyl spiromustine; docosanol; dolasetron; doxifluridine; droloxifene; dronabinol; duocarmycin SA; ebselen; ecomustine; edelfosine; edrecolomab; elemene; emitefur; episteride; estrogen agonists and antagonists; exemestane; filgrastim; finasteride; flavopiridol; flezelastine; fluasterone; fluorodaunorunicin; forfenimex; formestane; fotemustine; gadolinium texaphyrin; gallium nitrate; galocitabine; ganirelix; gelatinase inhibitors; glutathione inhibitors; hepsulfam; heregulin; hexamethylene bisacetamide; hypericin; ibandronic acid; idoxifene; idramantone; ilomastat; imidazoacridones; imiquimod; immunostimulant peptides; insulin-like growth factor-1 receptor inhibitor; interferon agonists; iobenguane; iododoxorubicin; ipomeanol; irinotecan; iroplact; irsogladine; isobengazole; isohomohalicondrin B; itasetron; jasplakinolide; kahalalide F; lamellarin-N; leinamycin; lenograstim; lentinan; leptolstatin; leukemia inhibiting factor; leuprorelin; levamisole; liarozole; lissoclinamide; lobaplatin; lombricine; lonidamine; lovastatin; loxoribine; lurtotecan; lutetium texaphyrin; lysofylline; mannostatin A; marimastat; masoprocol; maspin; matrilysin inhibitors; matrix metalloproteinase inhibitors; merbarone; meterelin; methioninase; metoclopramide; MIF inhibitors; mifepristone; miltefosine; mirimostim; mitoguazone; mitolactol; mitonafide; mitotoxin fibroblast growth factor-saporin; mofarotene; molgramostim; human chorionic gonadotrophin monoclonal antibody; mopidamol; mycaperoxide B; myriaporone; N-acetyldinaline; N-substituted benzamides; nafarelin; nagrestip; naloxone; pentazocine; napavin; naphterpin; nartograstim; nedaplatin; nemorubicin; neridronic acid; neutral endopeptidase; nilutamide; nisamycin; nitric oxide modulators; nitroxide antioxidant; nitrullyn; octreotide; okicenone; onapristone; ondansetron; ondansetron; oracin; osaterone; oxaliplatin; oxaunomycin; palauamine; palmitoylrhizoxin; pamidronic acid; panaxytriol; panomifene; parabactin; pazelliptine; peldesine; pentosan; pentostatin; pentrozole; perflubron; perillyl alcohol; phenazinomycin; phenylacetate; phosphatase inhibitors; picibanil; pilocarpine; pirarubicin; piritrexim; placetin A and B; plasminogen activator inhibitor; propyl bis-acridone; prostaglandin J2; proteasome inhibitors; protein kinase C inhibitors; protein tyrosine phosphatase inhibitors; purine nucleoside phosphorylase inhibitors; purpurins; pyrazoloacridine; raltitrexed; ramosetron; ras farnesyl protein transferase inhibitors; ras inhibitors; ras-GAP inhibitors; retelliptine; rhenium 186 etidronate; rhizoxin; retinamide; rohitukine; romurtide; roquinimex; rubiginone B1; ruboxyl; saintopin; sarcophytol A; sargramostim; sizofuran; sobu-zoxane; sodium borocaptate; sodium phenylacetate; solverol; somatomedin binding protein; sonermin; sparfosic acid; spicamycin D; splenopentin; spongistatin 1; squalamine; stem-cell division inhibitors; stipiamide; stromelysin inhibitors; sulfinosine; suradista; suramin; swainsonine; tallimustine; tamoxifen; tauromustine; tazarotene; tecogalan; tellurapyrylium; telomerase inhibitors; temozolomide; tetra-chlorodecaoxide; tetrazomine; thaliblastine; thiocoraline; thrombopoietin; thymalfasin; thymopoietin receptor agonist; thymotrinan; thyroid stimulating hormone; tin ethyl etiopurpurin; titanocene; topsentin; tretinoin; triacetyluridine; tropisetron; turosteride; tyrosine kinase inhibitors; tyrphostins; ubenimex; urogenital sinus-derived growth inhibitory factor; urokinase receptor antagonists; variolin B; velaresol; veramine; verdins; verteporfin; vinxaltine; vitaxin; zanoterone; zilascorb; and their pharmaceutically acceptable salts.

Synergistic activity of the pharmaceutical compositions or combined preparations of this invention against cell proliferation may be readily determined by means of one or more tests such as, but not limited to, the measurement of the radioactivity resulting from the incorporation of $^3$H-thymidine in culture of tumour cell lines. For instance, different tumour cell lines are selected in order to evaluate the antitumour effects of the test compounds, such as but not limited to:

RPMI1788: human Peripheral Blood Leucocytes (PBL) Caucasian tumor line,
Jurkat: human acute T cell leukemia,
EL4: C57Bl/6 mouse lymphoma, or
THP-1: human monocyte tumour line.

Depending on the selected tumour cell line, different culture media may be used, such as for example:
for RPMI1788 and THP-1: RPMI-1640+10% FCS+1% NEAA+1% sodium pyruvate+5×10$^5$ mercapto-ethanol+antibiotics (G–418 0.45 µg/ml).
for Jurkat and EL4: RPMI-1640+10% FCS+antibiotics (G-418 0.45 µg/ml).

In a specific embodiment of the synergy determination test, the tumour cell lines are harvested and a suspension of 0.27× 10$^6$ cells/ml in complete medium is prepared. The suspensions (150 µl) are added to a microtiter plate in triplicate. Either complete medium (controls) or the test compounds at the test concentrations (50 µl) are added to the cell suspension in the microtiter plate. The cells are incubated at 37° C. under 5% $CO_2$ for about 16 hours. $^3$H-thymidine is added, and the cells incubated for another 8 hours. The cells are harvested and radioactivity is measured in counts per minute (CPM) in a β-counter. The $^3$H-thymidine cell content, and thus measured radioactivity, is proportional to the proliferation of the cell lines. The synergistic effect is evaluated by the median effect analysis method as disclosed herein-before.

The pharmaceutical composition or combined preparation with synergistic activity against cell proliferation according to this invention may contain the azonafide derivative having one of the formulae (I), (II), (III) or (IV), and/or a pharmaceutically acceptable salt thereof and/or a solvate thereof, over a broad content range depending on the contemplated use and the expected effect of the preparation. Generally, the azonafide derivative content of the combined preparation is within the range of 0.1 to 99.9% by weight, preferably from 1 to 99% by weight, more preferably from 5 to 95% by weight.

The pharmaceutical compositions and combined preparations according to this invention may be administered orally or in any other suitable fashion. Oral administration is preferred and the preparation may have the form of a tablet, aqueous dispersion, dispersable powder or granule, emulsion, hard or soft capsule, syrup, elixir or gel. The dosing forms may be prepared using any method known in the art for manufacturing these pharmaceutical compositions and may comprise as additives sweeteners, flavoring agents, coloring agents, preservatives and the like. Carrier materials and excipients are detailed hereinbelow and may include, inter alia, calcium carbonate, sodium carbonate, lactose, calcium phosphate or sodium phosphate; granulating and disintegrating agents, binding agents and the like. The pharmaceutical composition or combined preparation of this invention may be included in a gelatin capsule mixed with any inert solid diluent or carrier material, or has the form of a soft gelatin capsule, in which the ingredient is mixed with a water or oil medium. Aqueous dispersions may comprise the biologically active composition or combined preparation in combination with a suspending agent, dispersing agent or wetting agent. Oil dispersions may comprise suspending agents such as a vegetable oil. Rectal administration is also applicable, for instance in the form of suppositories or gels. Injection (e.g. intramuscularly or intraperitoneally) is also applicable as a mode of administration, for instance in the form of injectable solutions or dispersions, depending upon the disorder to be treated and the condition of the patient.

The term "pharmaceutically acceptable carrier or excipient" as used herein in relation to pharmaceutical compositions and combined preparations means any material or substance with which the active principle, i.e. the azonafide derivative and optionally the antineoplastic drug, may be formulated in order to facilitate its application or dissemination to the locus to be treated, for instance by dissolving, dispersing or diffusing the said composition, and/or to facilitate its storage, transport or handling without impairing its effectiveness. The pharmaceutically acceptable carrier may be a solid or a liquid or a gas which has been compressed to form a liquid, i.e. the compositions of this invention can suitably be used as concentrates, emulsions, solutions, granulates, dusts, sprays, aerosols, pellets or powders.

Suitable pharmaceutical carriers for use in the said pharmaceutical compositions and their formulation are well known to those skilled in the art. There is no particular restriction to their selection within the present invention although, due to the usually low or very low water-solubility of the pteridine derivatives of this invention, special attention will be paid to the selection of suitable carrier combinations that can assist in properly formulating them in view of the expected time release profile. Suitable pharmaceutical carriers include additives such as wetting agents, dispersing agents, stickers, adhesives, emulsifying or surface-active agents, thickening agents, complexing agents, gelling agents, solvents, coatings, antibacterial and antifungal agents (for example phenol, sorbic acid, chlorobutanol), isotonic agents (such as sugars or sodium chloride) and the like, provided the same are consistent with pharmaceutical practice, i.e. carriers and additives which do not create permanent damage to mammals. The pharmaceutical compositions of the present invention may be prepared in any known manner, for instance by homogeneously mixing, dissolving, spray-drying, coating and/or grinding the active ingredients, in a one-step or a multi-steps procedure, with the selected carrier material and, where appropriate, the other additives such as surface-active agents. The pharmaceutical compositions of the present invention may also be prepared by micronisation, for instance in view to obtain them in the form of microspheres usually having a diameter of about 1 to 10 µm, namely for the manufacture of microcapsules for controlled or sustained release of the biologically active ingredient(s).

Suitable surface-active agents to be used in the pharmaceutical compositions of the present invention are non-ionic, cationic and/or anionic materials having good emulsifying, dispersing and/or wetting properties. Suitable anionic surfactants include both water-soluble soaps and water-soluble synthetic surface-active agents. Suitable soaps are alkaline or alkaline-earth metal salts, unsubstituted or substituted ammonium salts of higher fatty acids ($C_{10}$-$C_{22}$), e.g. the sodium or potassium salts of oleic or stearic acid, or of natural fatty acid mixtures obtainable form coconut oil or tallow oil. Synthetic surfactants include sodium or calcium salts of polyacrylic acids; fatty sulphonates and sulphates; sulphonated benzimidazole derivatives and alkylaryl-sulphonates. Fatty sulphonates or sulphates are usually in the form of alkaline or alkaline-earth metal salts, unsubstituted ammonium salts or ammonium salts substituted with an alkyl or acyl radical having from 8 to 22 carbon atoms, e.g. the sodium or calcium salt of lignosulphonic acid or dodecylsulphonic acid or a mixture of fatty alcohol sulphates obtained from natural fatty acids, alkaline or alkaline-earth metal salts of sulphuric or sulphonic acid esters (such as sodium lauryl sulphate) and sulphonic acids of fatty alcohol/ethylene oxide adducts. Suitable sulphonated benzimidazole derivatives preferably contain 8 to 22 carbon atoms. Examples of alkylaryl-sulphonates are the sodium, calcium or alcanolamine salts of dodecylbenzene sulphonic acid or dibutyl-naphtalenesulphonic acid or a naphtalene-sulphonic acid/formaldehyde condensation product. Also suitable are the corresponding phosphates, e.g. salts of phosphoric acid ester and an adduct of p-nonylphenol with ethylene and/or propylene oxide, or phospholipids. Suitable phospholipids for this purpose are the natural (originating from animal or plant cells) or synthetic phospholipids of the cephalin or lecithin type such as e.g. phosphatidylethanolamine, phosphatidylserine, phosphatidylglycerine, lysolecithin, cardiolipin, dioctanyl-phosphatidylcholine, dipalmitoylphoshatidylcholine and their mixtures.

Suitable non-ionic surfactants include polyethoxylated and polypropoxylated derivatives of alkylphenols, fatty alcohols, fatty acids, aliphatic amines or amides containing at least 12 carbon atoms in the molecule, alkylarenesulphonates and dialkylsulphosuccinates, such as polyglycol ether derivatives of aliphatic and cycloaliphatic alcohols, saturated and unsaturated fatty acids and alkylphenols, said derivatives preferably containing 3 to 10 glycol ether groups and 8 to 20 carbon atoms in the (aliphatic) hydrocarbon moiety and 6 to 18 carbon atoms in the alkyl moiety of the alkylphenol. Further suitable non-ionic surfactants are water-soluble adducts of polyethylene oxide with poylypropylene glycol, ethylene-diamino-polypropylene glycol containing 1 to 10 carbon atoms in the alkyl chain, which adducts contain 20 to 250 ethyleneglycol ether groups and/or 10 to 100 propyleneglycol ether groups. Such compounds usually contain from 1 to 5 ethyleneglycol units per propyleneglycol unit. Representative examples of non-ionic surfactants are nonylphenol-polyethoxyethanol, castor oil polyglycolic ethers, polypropylene/polyethylene oxide adducts, tributylphenoxypolyethoxyethanol, polyethyleneglycol and octylphenoxypolyethoxyethanol. Fatty acid esters of polyethylene sorbitan (such as polyoxyethylene sorbitan trioleate), glycerol, sorbitan, sucrose and pentaerythritol are also suitable non-ionic surfactants.

Suitable cationic surfactants include quaternary ammonium salts, preferably halides, having 4 hydrocarbon radicals optionally substituted with halo, phenyl, substituted phenyl or hydroxy; for instance quaternary ammonium salts containing as N-substituent at least one $C_8$-$C_{22}$ alkyl radical (e.g. cetyl, lauryl, palmityl, myristyl, oleyl and the like) and, as further substituents, unsubstituted or halogenated lower alkyl, benzyl and/or hydroxy-lower alkyl radicals.

A more detailed description of surface-active agents suitable for this purpose may be found for instance in "McCutcheon's Detergents and Emulsifiers Annual" (MC Publishing Crop., Ridgewood, N.J., 1981), "Tensid-Taschenbuch", $2^{nd}$ ed. (Hanser Verlag, Vienna, 1981) and "Encyclopaedia of Surfactants (Chemical Publishing Co., New York, 1981).

Structure-forming, thickening or gel-forming agents may be included into the pharmaceutical compositions and combined preparations of the invention. Suitable such agents are in particular highly dispersed silicic acid, such as the product commercially available under the trade name Aerosil; bentonites; tetraalkyl ammonium salts of montmorillonites (e.g., products commercially available under the trade name Bentone), wherein each of the alkyl groups may contain from 1 to 20 carbon atoms; cetostearyl alcohol and modified castor oil products (e.g. the product commercially available under the trade name Antisettle).

Gelling agents which may be included into the pharmaceutical compositions and combined preparations of the present invention include, but are not limited to, cellulose derivatives such as carboxymethylcellulose, cellulose acetate and the like; natural gums such as arabic gum, xanthum gum, tragacanth gum, guar gum and the like; gelatin; silicon dioxide; synthetic polymers such as carbomers, and mixtures thereof. Gelatin and modified celluloses represent a preferred class of gelling agents.

Other optional excipients which may be included in the pharmaceutical compositions and combined preparations of the present invention include additives such as magnesium oxide; azo dyes; organic and inorganic pigments such as titanium dioxide; UV-absorbers; stabilisers; odor masking agents; viscosity enhancers; antioxidants such as, for example, ascorbyl palmitate, sodium bisulfite, sodium metabisulfite and the like, and mixtures thereof; preservatives such as, for example, potassium sorbate, sodium benzoate, sorbic acid, propyl gallate, benzylalcohol, methyl paraben, propyl paraben and the like; sequestering agents such as ethylene-diamine tetraacetic acid; flavoring agents such as natural vanillin; buffers such as citric acid and acetic acid; extenders or bulking agents such as silicates, diatomaceous earth, magnesium oxide or aluminum oxide; densification agents such as magnesium salts; and mixtures thereof.

Additional ingredients may be included in order to control the duration of action of the biologically-active ingredient in the compositions and combined preparations of the invention. Control release compositions may thus be achieved by selecting appropriate polymer carriers such as for example polyesters, polyamino-acids, polyvinyl-pyrrolidone, ethylene-vinyl acetate copolymers, methylcellulose, carboxymethylcellulose, protamine sulfate and the like. The rate of drug release and duration of action may also be controlled by incorporating the active ingredient into particles, e.g. microcapsules, of a polymeric substance such as hydrogels, polylactic acid, hydroxymethyl-cellulose, polymethyl methacrylate and the other above-described polymers. Such methods include colloid drug delivery systems like liposomes, microspheres, microemulsions, nanoparticles, nanocapsules and so on. Depending on the route of administration, the pharmaceutical composition or combined preparation of the invention may also require protective coatings.

Pharmaceutical forms suitable for injectable use include sterile aqueous solutions or dispersions and sterile powders for the extemporaneous preparation thereof. Typical carriers for this purpose therefore include biocompatible aqueous buffers, ethanol, glycerol, propylene glycol, polyethylene glycol, complexing agents such as cyclodextrins and the like, and mixtures thereof.

Since, in the case of combined preparations including the substituted azonafide derivative having one of the formulae (I), (II), (III) or (IV), and/or a pharmaceutically acceptable salt thereof and/or a solvate thereof, and an antineoplastic drug, both ingredients do not necessarily bring out their synergistic therapeutic effect directly at the same time in the patient to be treated, the said combined preparation may be in the form of a medical kit or package containing the two ingredients in separate but adjacent form. In the latter context, each ingredient may therefore be formulated in a way suitable for an administration route different from that of the other ingredient, e.g. one of them may be in the form of an oral or parenteral formulation whereas the other is in the form of an ampoule for intravenous injection or an aerosol.

The present invention further relates to a method for preventing or treating a cell proliferative disorder in a patient, preferably a mammal, more preferably a human being. The method of this invention consists of administering to the patient in need thereof an effective amount of a substituted azonafide derivative having the formula (I), (II), (III) or (IV), and/or a pharmaceutically acceptable salt thereof and/or a solvate thereof, optionally together with an effective amount of an antineoplastic drug, or a pharmaceutical composition comprising the same, such as disclosed above in extensive details. The effective amount of the substituted azonafide derivative is usually in the range of 0.01 mg to 20 mg, preferably 0.1 mg to 5 mg, per day per kg bodyweight for humans. Depending upon the pathologic condition to be treated and the patient's condition, the said effective amount may be divided into several subunits per day or may be administered at more than one day intervals. The patient to be treated may be any warm-blooded animal, preferably a human being, suffering from said pathologic condition.

The following examples are intended to illustrate several embodiments of the present invention, including the preparation and biological evaluation of the substituted azonafides, without limiting its scope in any way. The standard nomenclature of the dibenzisoquinoline structure is as indicated herinbelow:

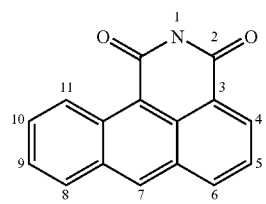

A general scheme representing one method for manufacturing the compounds of the invention is shown in appended figure 1 and will be illustrated by the series of examples below. The anthracene derivatives to be used as starting materials for the performance of this method may be prepared by treating an anthracene with oxalyl chloride, followed by oxidation with hydrogen peroxide in accordance with the procedure described by E. D. Bergman and R Ikan in *J. Org. Chem.*, 23, 907 (1958).

EXAMPLE 1

Preparation of 8- and 11-nitro-1,9-dicarboxylic-anhydride-anthracene

This method is based on the teaching of example 9 of U.S. Pat. No. 5,635,506 and proceeds according to the reaction shown below:

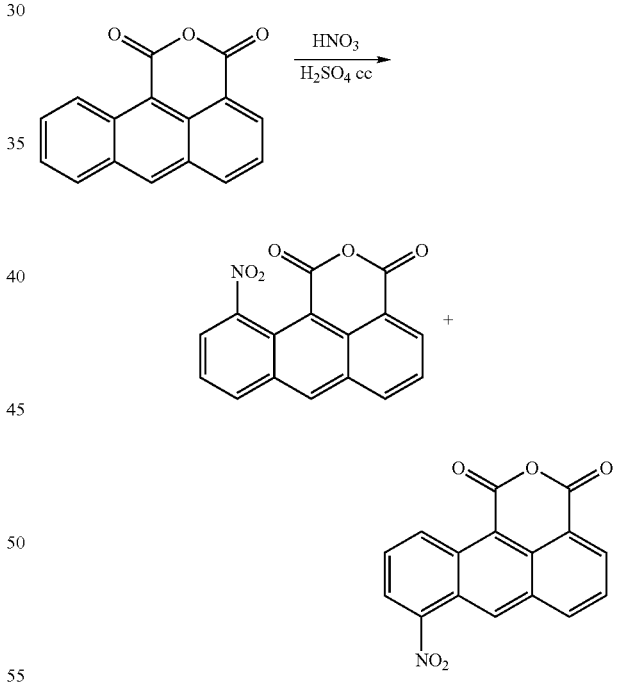

A mixture of 1.010 g (4.07 mmol) of 1,9-dicarboxylic-anhydride-anthracene in 30 mL of concentrated sulfuric acid was stirred at −12° C. before adding 358 mg (1 molar equivalent) of 65% nitric acid (in 1 mL of sulfuric acid). The resulting mixture was stirred during 15 minutes and then was poured in 100 mL of iced water. The resulting yellow solid was filtrated, washed and dried. The dry solid product (1.100 g, yield: 91%) was determined by NMR $^1$H spectra analysis to be a mixture of two regioisomers which were not easily separable at this stage and were used in the following reaction without further purification.

EXAMPLE 2

Preparation of a Mixture of 2-[2-(dimethylamino) ethyl]-11-nitro-1H-dibenzo[de,h]isoquinoline-1,3 (2H)-dione and 2-[2-(dimethylamino)ethyl]-8-nitro-1H-dibenzo[de,h]isoquinoline-1,3(2H)-dione This method is based on the teaching of example 10 of U.S. Pat. No. 5,635,506 and proceeds according to the reaction shown below:

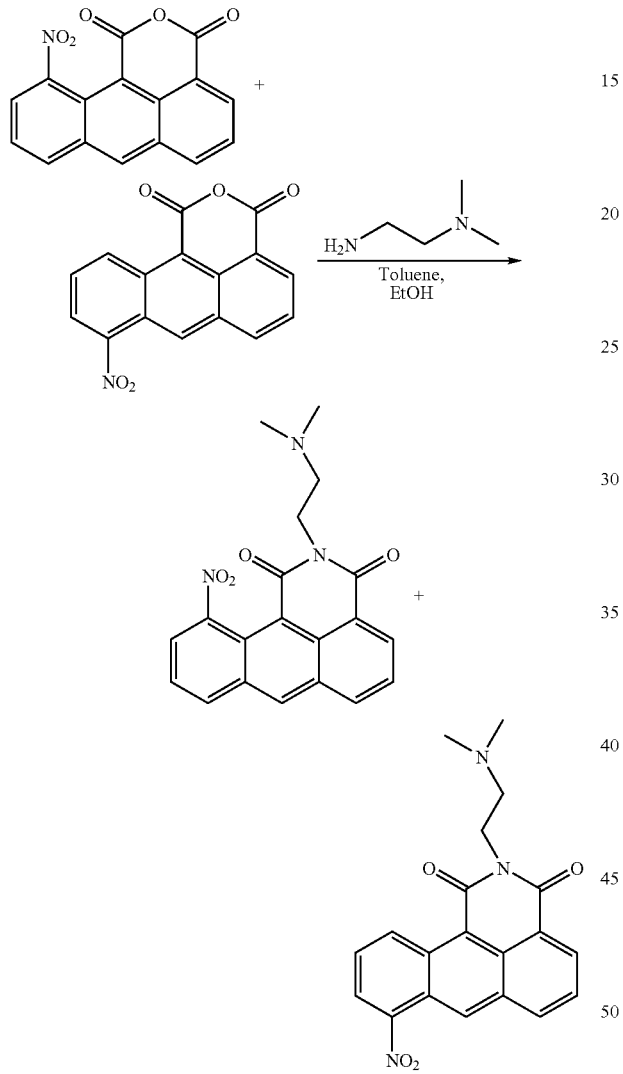

EXAMPLES 3 and 4

Preparation of 11-amino-2-[2-(dimethylamino) ethyl]-1H-dibenzo[de,h]isoquinoline-1,3(2H)-dione and 8-amino-2-[2-(dimethylamino)ethyl]-1H-dibenzo[de,h]isoquinoline-1,3(2H)-dione This method is based on the teaching of example 12 of U.S. Pat. No. 5,635,506 and proceeds according to the reaction shown below:

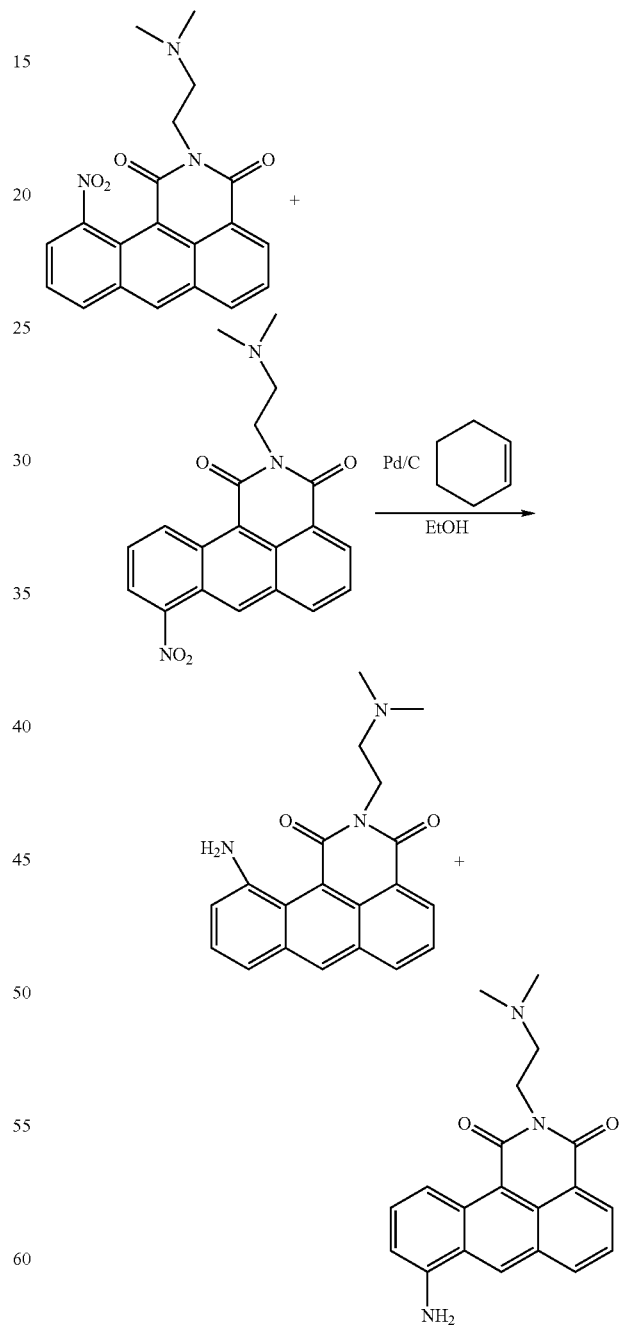

A suspension of 1.4 g (4.78 mmol) of the mixture of 8- and 11-nitro-1,9-dicarboxylic-anhydride-anthracenes (obtained in example 1) in 100 mL of toluene and 20 mL of ethanol was treated with 0.630 ml (1.2 molar equivalent) of N,N-dimethyl-aminopropyldiamine. The mixture was refluxed for 3 hours until it could be determined by thin layer chromatography (TLC) that the starting product mixture had disappeared. The mixture was then evaporated and the resulting residue was submitted to a flash chromatography on silica (eluent $CH_2Cl_2$/methanol in a 95:5 volume ratio) to give 1.230 g (yield: 70%) of a mixture of the two regioisomers respectively substituted in positions 8 and 11 of the anthracene moiety.

A suspension of 1.230 g (3.35 mmol) of a mixture (obtained in example 2) of 2-[2-(dimethylamino)ethyl]-11-nitro-1H-dibenzo[de,h]isoquinoline-1,3(2H)-dione and 2-[2-

(dimethylamino)ethyl]-8-nitro-1H-dibenzo[de,h]isoquinoline-1,3(2H)-dione and 887 mg (0.25 molar equivalent) of a palladium/carbon hydrogenation catalyst in 60 mL of ethanol was stirred at 20° C. 12 mL of cyclohexene were then added before refluxing the resulting mixture during 18 hours. 887 mg of the catalyst were then added again and reflux was prolonged during 8 hours. The reaction mixture was then cooled, filtered on Celite and washed by 2 L of a solution of $CH_2Cl_2$/methanol in a 1/1 ratio. The solvent was then evaporated under vacuum and the residue was purified by flash chromatography on silica (eluent $CH_2Cl_2$/methanol in a 95:5 volume ratio). In this way, two products were isolated in amounts of 350 mg and 185 mg respectively (yields: 31% and 13%). The major product was determined via $^1H$ NMR spectra analysis to be 11-amino-2-[2-(dimethylamino)ethyl]-1H-dibenzo[de,h]isoquinoline-1,3(2H)-dione (formula below) and the minor product to be 8-amino-2-[2-(dimethylamino)ethyl]-1H-dibenzo[de,h]isoquinoline-1,3(2H)-dione.

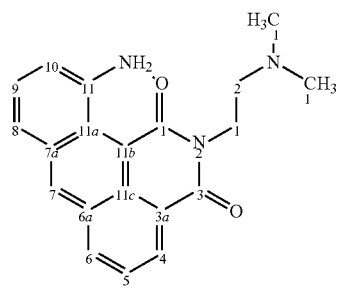

The major product was characterized by the following techniques:

melting point (hereinafter referred as m.p.): 189° C.;

Mass spectrum (respectively Electronic Ionisation Mass Spectrometry hereinafter referred as EIMS or Electro Spray Ionisation Mass Spectrometry hereinafter referred as ESIMS): 333 (M+), and 262;

Proton nuclear magnetic resonance (hereinafter referred as $^1H$ NMR) (CDCl$_3$): 8.80 (H-7, s); 8.67 (H-4, d, J=6.9 Hz); 8.33 (H-6, d, J=7.5 Hz); 7.70 (H-5, t, J=7.2 Hz); 7.66 (H-8, d, J=6.3 Hz); 7.50 (H-9, t, J=6.9 Hz); 7.16 (H-10, d, J=7.2 Hz); 4.42 (CH$_2$—N, t, J=7.5 Hz); 3.36 (NH2, bs); 2.78 (CH$_2$—N, t, J=7.5 Hz) and 2.45 (N(CH$_3$)$_2$, s); and Carbon nuclear magnetic resonance (hereinafter referred as $^{13}C$ NMR) (CDCl$_3$): 166.3; 164.4; 143.7; 138.2; 135.5; 134.8; 133.9; 128.8; 127.8; 125.5; 124.0; 122.3; 121.7; 117.8; 117.2; 57.0; 48.2; 45.5; and 38.9.

The minor product was similarly characterized by:
m.p.: 238° C.; and
$^1H$ NMR (CDCl$_3$): 9.27 (H-7, s); 9.03 (H-7, s); 8.67 (H-4, d, J=6 Hz); 8.33 (H-6, d, J=7.5 Hz); 7.70 (H-5, t, J=7.2 Hz); 7.61 (H-8, d, J=6.2 Hz); 6.88 (H-9, t, d=6.9 Hz); 4.44 (CH$_2$—N, t, J=7.5 Hz); 4.23 (NH2, bs); 2.76 (CH$_2$—N, t, J=7.5 Hz) and 2.08 (N(CH$_3$)$_2$, s).

EXAMPLE 5

Preparation of 11-{[(1Z)-(2,5-dihydroxyphenyl)methylidene}amino]-2-[2-(dimethylamino)ethyl]-1H-dibenzo[de,h]isoquinoline-1,3(2H)-dione A mixture of 100 mg (0.30 mmole) of 2-[2-(dimethylamino)ethyl]-11-amino-3H-dibenzo[deh]isoquinoline-1,3(2H)-dione (obtained in example 3), 5 mL of toluene and 50 mg (1.2 molar equivalent) of 2,5-dihydroxybenzaldehyde was refluxed for 3 hours. After cooling, toluene was evaporated under reduced pressure and the residue was submitted to a flash chromatography on silica (eluent: $CH_2Cl_2$/methanol in a 95:5 volume ratio) and then 90/10), thus resulting in 120 mg (yield: 88%) of the desired product (formula below) as an orange powder.

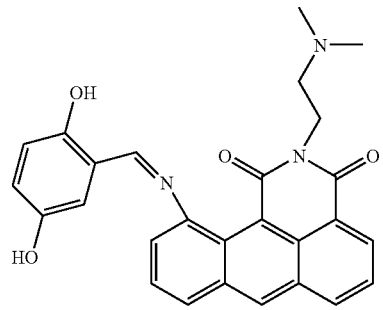

which was characterized as follows:
m.p.: 225° C.;
EIMS: 453(M+), 383, and 262;
$^1H$ NMR (300 MHz, DMSO) as follows: 11.83 (OH, s), 9.20 (H-7, s); 9.10 (OH, s); 8.88 (H arom, s); 8.58 (H-4, d, J=6.9 Hz); 8.18 (H-6, d, J=8.1 Hz); 7.87 (H-9, t, J=7.8 Hz); 7.77 (H-5, t, J=8.4 Hz); 7.52 (H-8, d, J=8.4 Hz); 7.12 (N=CH, s); 6.89 (H-9, dd, J=9 and 3 Hz); 6.80 (H arom, d, J=8.7 Hz); 4.01 (CH$_2$—N, t, J=7.5 Hz); 2.40 (CH$_2$—N, t, J=7.5 Hz) and 2.08 (N(CH$_3$)$_2$, s) and;

$^{13}C$ NMR (75.4 MHz, DMSO): 163.1, 162.3, 161.0, 152.7, 149.6, 146.8, 135.1, 134.5, 133.1, 132.5, 128.4, 127.5, 127.2, 127.0, 126.3, 126.0, 121.9, 120.5, 119.8, 117.7, 117.0, 116.9, 116.8, 56.0, 45.0 and 38.0.

EXAMPLE 6

Preparation of 8-{[(1Z)-(2,5-dihydroxyphenyl)methylidene]amino}-2-[2-(dimethylamino)ethyl]-1H-dibenzo[de,h]isoquinoline-1,3(2H)-dione A mixture of 50 mg (0.150 mmole) of 8-amino-2-[2-(dimethylamino)ethyl]-1H-dibenzo[de,h]isoquinoline-1,3(2H)-dione (obtained in example 4), 5 mL of toluene and 25 mg (1.2 molar equivalent) of 2,5-dihydroxybenzaldehyde was refluxed for 3 hours. After cooling, toluene was evaporated under reduced pressure and the residue was submitted to a flash chromatography on silica (eluent: $CH_2Cl_2$/methanol in a 95:5 and then a 90:10 volume ratio), thus resulting in 60 mg (yield: 88%) of the desired product (formula below) as a deep red powder.

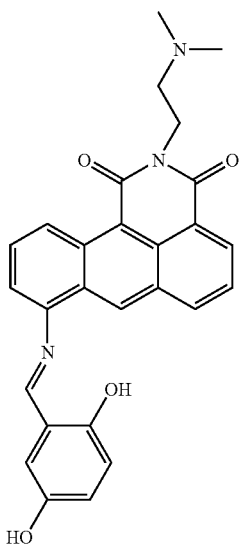

which was characterized as follows:
 m.p.: 205° C.;
 EIMS: 453(M+), 383 and 262; and
 $^1$H NMR (300 MHz, DMSO): 11.48 (OH, s), 9.77 (H-11, d, J=9.3 Hz); 9.31 (H-7, s); 9.19 (OH, s); 8.96 (H arom, s); 8.63 (H-4, d, J=8.4 Hz); 8.60 (H arom, d, J=7.2 Hz); 7.8-8.0 (H-5=H10, m); 7.44 (H-Arom, d, J=7.2 Hz); 7.25 (N=CH, s); 6.9-7.0 (H-9+Arom, m); 4.22 (CH$_2$—N, t, J=7.5 Hz); 2.58 (CH$_2$—N, t, J=7.5 Hz) and 2.25 (N(CH$_3$)$_2$, s).

EXAMPLE 7

Preparation of 11-{[(1Z)-1,3-benzodioxol-5-ylmethylidene]amino}-2-[2-(dimethylamino)ethyl]-1H-dibenzo[de,h]isoquinoline-1,3(2H)-dione Synthesis of this compound proceeds according to the scheme below:

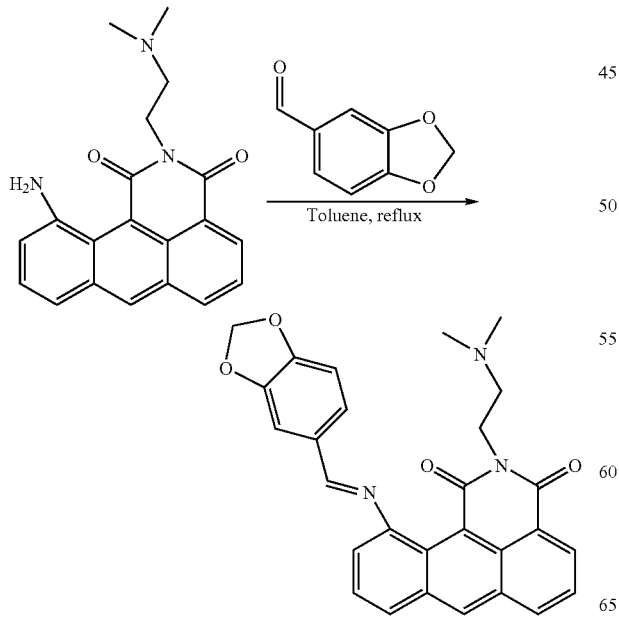

100 mg of 11-amino-2-[2-(dimethylamino)ethyl]-1H-dibenzo[de,h]isoquinoline-1,3(2H)-dione (obtained in example 3) (0.30 mmol), 10 mL of toluene and 54 mg of piperonal (1.2 molar equivalent) were refluxed for 60 hours. After cooling, the solvent was evaporated under reduce pressure and the residue was submitted to a flash chromatography on silica (eluent: CH$_2$Cl$_2$/methanol in a 95:5 and then a 90:10 volume ratio) to provide 88 mg (yield=63%) of the desired compound as a brown powder which was characterized as follows:
 m.p. 198° C.;
 EIMS: 465(M+), 422, 395 and 377;
 $^1$H NMR (300 MHz, DMSO): 8.76 (H-7, s); 8.65 (H-4, dd, J=8.0 Hz); 8.60 (N=CH, s); 8.32 (H-6, d, J=7.8 Hz); 7.90 (H-Arom, d; J=7.8 Hz); 7.71 (H-9, t, J=7.2 Hz); 7.77 (H-5, t, J=6.9 Hz); 7.5 (H Arom, s); 7.37 (H arom, d, J=8.1); 7.16 (H-10, d, J=7.2) 6.89 (H-8, dd, J=9 and 3 Hz); 6.80 (H-8, d, J=7.8 Hz); 4.20 (CH$_2$—N, t, J=7.5 Hz); 2.53 (CH$_2$—N, t, J=7.5 Hz) and 2.21 (N(CH$_3$)$_2$, s); and
 $^{13}$C NMR (75.4 MHz, DMSO): 164.3, 163.1; 157.0; 150.5; 149.9; 148.4; 134.1; 133.9; 133.8; 132.3; 131.6; 128.9; 128.1; 127.1; 125.9; 125.9; 125.6; 123.0; 119.3; 118.5; 108.3; 106.9; 101.5; 56.7; 45.3 and 38.4.

EXAMPLE 8

Preparation of 8-{[(1E)-1,3-benzodioxol-5-ylmethylidene]amino}-2-[2-(dimethylamino)ethyl]-1H-dibenzo[de,h]isoquinoline-1,3(2H)-dione Synthesis of this compound proceeds according to the scheme below:

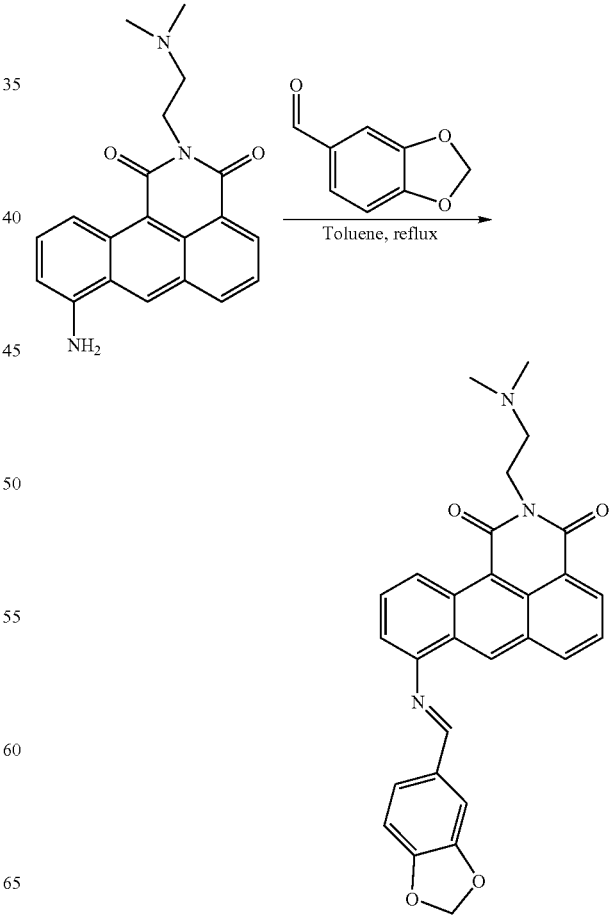

100 mg of 8-amino-2-[2-(dimethylamino)ethyl]-1H-dibenzo[de,h]isoquinoline-1,3(2H)-dione (obtained in example 4) (0.30 mmol), 10 mL of toluene and 54 mg of piperonal (1.2 equivalent) were refluxed for 18 hours. After cooling, the solvent was evaporated under reduce pressure and the residue was submitted to a flash chromatography on silica (eluent: $CH_2Cl_2$/methanol in a 95:5 and then a 90:10 volume ratio) to provide 130 mg (yield=93%) of the desired product as a deep orange powder which was characterized as follows:

EIMS: 465(M+) and 394;

$^1$H NMR (300 MHz, DMSO): 9.82 (H-11, d, J=9.6 Hz); 9.37 (H-7, s); 8.70 (H-4, dd, J=6.9 and 1.2 Hz); 8.49 (H-2', s); 8.33 (H-6', d, J=7.8 Hz); 7.77 (H-5, d, J=9.3 Hz); 7.73 (CH=N, s); 7.67 (H-10, d, J=9.6 and 7.5 Hz); 7.39 (H-6, dd, J=7.5 and 1.2 Hz); 6.94 (H-9, d, J=7.8 Hz); 6.10 (O—$CH_2$—O, s); 4.42 ($CH_2$—N, t, J=7.5 Hz); 2.72 ($CH_2$—N, t, J=7.5 Hz) and 2.40 (N($CH_3$)$_2$, s); and $^{13}$C NMR (75.4 MHz, DMSO): 165.2, 163.7, 160.0, 151.0, 150.0, 148.6, 135.8, 133.9, 133.6, 132.9, 131.7, 131.1, 128.9, 128.4, 126.4, 125.1, 124.3, 122.2, 114.8, 112.1, 108.4, 107.0, 101.8, 101.7, 56.9, 45.7 and 38.3.

EXAMPLE 9

Preparation of methyl {2-[2-(dimethylamino)ethyl]-1,3-dioxo-2,3-dihydro-1H-dibenzo[de,h]isoquinolin-11-yl}carbamate A solution of 100 mg (0.30 mmole) of 11-amino-2-[2-(dimethylamino)ethyl]-1H-dibenzo[de,h]isoquinoline-1,3(2H)-dione (obtained in example 3), 7 mL of dichloromethane, 23 μL of methyl chloroformate and 41 μL of triethylamine were added. The mixture was magnetically stirred at 20° C. during 4 hours. The solvent was then evaporated under reduced pressure and the residue was submitted to a flash chromatography on silica (eluent: $CH_2Cl_2$/methanol in a 97:3 volume ratio) to provide 102 mg (yield: 87%) of the desired product (formula below) as an orange powder

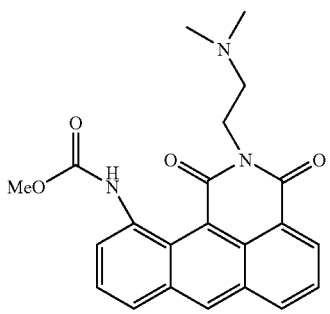

which was characterized as follows:

EIMS: 391(M+), 320 and 288;

$^1$H NMR (300 MHz, CDCl$_3$): 9.27 (N—H, s); 8.83 (H-7, s); 8.74 (H-4, dd, J=6.0 Hz, J=1.5 Hz); 8.33 (H-6, d, J=7.5 Hz); 8.08 (H-8, d, J=7.2 Hz); 7.96 (H-10, d, J=7.2 Hz); 7.72 (H-5, dd, J=7.4 and 6.0 Hz); 7.68 (H-9, t, J=7.5 Hz); 4.47 ($CH_2$—N, t, J=7.0 Hz); 3.74 (O—$CH_3$, s)°; 2.76 ($CH_2$—N, t, J=6.6 Hz); and 2.40 (N($CH_3$)$_2$, s); and $^{13}$C NMR (75.4 MHz, CDCl$_3$): 166.8, 163.6, 155.6, 137.6, 134.8, 134.1, 133.2, 129.0, 128.2, 128.1, 127.7, 127.4, 126.8, 125.6, 122.3, 116.6, 57.3, 52.1, 45.8 and 39.1.

EXAMPLE 10

Preparation of 4-chloro-N-{2-[2-(dimethylamino)ethyl]-1,3-dioxo-2,3-dihydro-1H-dibenzo[de,h]isoquinolin-11-yl}butanamide A solution of 100 mg (0.30 mmole) of 11-amino-2-[2-(dimethylamino)ethyl]-1H-dibenzo[de,h]isoquinoline-1,3(2H)-dione (obtained in example 3) in 4 mL of acetonitrile was stirred at 20° C. 68 μL of 4-chlorobutyryl chloride were added. The mixture was magnetically stirred at 20° C. during 3 hours. The solvent was then evaporated under reduced pressure and the residue was submitted to a flash chromatography on silica (eluent: $CH_2Cl_2$/methanol in a 97:3 volume ratio) to provide 70 mg (yield: 53%) of the desired product (formula below) as an orange powder

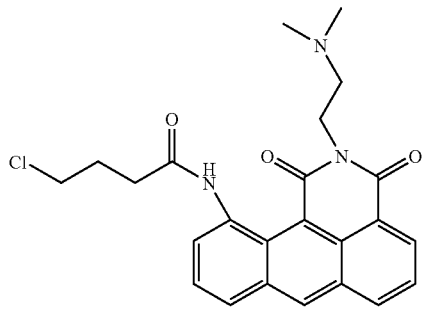

which was characterized as follows:

EIMS: 437(M−1); 331; 71 and 58;

$^1$H NMR (300 MHz, CDCl$_3$): 10.23 (N—H, s); 8.87 (H-7, s); 8.78 (H-4, dd, J=7.0 Hz, J=1.5 Hz); 8.35 (H-6, dd, J=8.4 Hz, J=0.7 Hz); 8.16 (H-8, d, J=7.0 Hz); 8.01 (H-10, d, J=8.1 Hz); 7.73 (H-5, dd, J=8.0 and 7 Hz,); 7.68 (H-9, t, J=7.8 Hz); 4.47 ($CH_2$—N, t, J=7.0 Hz); 3.66 ($CH_2$—CO, t, J=6.2 Hz); 2.76 ($CH_2$—N, t, J=7.0 Hz); 2.65 (Cl—$CH_2$, t, J=7.0 Hz); 2.42 (N($CH_3$)$_2$, s); and 2.22 (Cl—$CH_2$—$CH_2$, quin, J=6.6 Hz); and $^{13}$C NMR (CDCl$_3$) ppm: 171.0; 166.7; 163.9; 138.4; 135.60; 134.8; 134.2; 132.1; 129.7; 129.50; 128.6; 128.5; 127.9; 126.8; 125.9; 122.2; 116.34; 57.0; 45.5; 44.6; 39.0; 34.4; and 28.1.

EXAMPLE 11

Preparation of 2-(4-chlorophenyl)-N-{2-[2-(dimethylamino)ethyl]-1,3-dioxo-2,3-dihydro-1H-dibenzo[de,h]isoquinolin-11-yl}acetamide

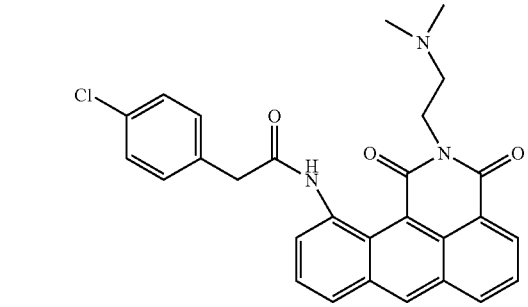

A solution of 100 mg (0.30 mmole) of 11-amino-2-[2-(dimethylamino)ethyl]-1H-dibenzo[de,h]isoquinoline-1,3(2H)-dione (obtained in example 3) in 7 mL of dichloromethane was magnetically stirred at 20° C. 113 µL (2 molar equivalents) of 4-chlorophenylacetyl chloride were added. The mixture was magnetically stirred at room temperature during 3 hours. The solvent was then evaporated under reduced pressure and the residue was submitted to a flash chromatography on silica (eluent: $CH_2Cl_2$/methanol in a 97:3 volume ratio) to provide 122 mg (yield: 84%). of the desired product (formula above) as an orange powder which was characterized as follows:

EIMS: 485(M−1); 414; 360; 315; 289; 246; 218; 190; 125; 89; 71 and 58;

$^1$H NMR (300 MHz, $CDCl_3$) 10.26 (N—H, s); 8.86 (H-7, s); 8.77 (H-4, dd, J=7.0 Hz, J=1.5 Hz); 8.35 (H-6, dd, J=8.4 Hz, J=1.1 Hz); 8.13 (H-8, d, J=6.6 Hz); 8.00 (H-10, d, J=7.7 Hz); 7.74 (H-5, dd, J=8.0 and 7 Hz,); 7.68 (H-9, t, J=7.8 Hz); 7.34 (4H-arom, m); 4.37 ($CH_2$—N, t, J=6.6 Hz); 3.73 (Ph-$CH_2$—CO, s); 2.72 ($CH_2$—N, t, J=7.0 Hz); 2.42 (N($CH_3$)$_2$, s); and $^{13}$C NMR (75.4 MHz, $CDCl_3$): 169.2; 166.7; 163.5; 138.2; 135.2; 134.6; 134.0; 133.5; 133.1; 132.3; 130.7; 129.6; 128.8; 128.3; 126.7; 125.7; 57.3; 45.7; 44.2; and 39.3.

EXAMPLE 12

Preparation of 1-(1,3-benzodioxol-5-yl)-3-{2-[2-(dimethylamino)ethyl]-1,3-dioxo-2,3-dihydro-1H-dibenzo[de,h]isoquinolin-11-yl}urea A solution of 100 mg (0.30 mmole) of 11-amino-2-[2-(dimethylamino)ethyl]-1H-dibenzo[de,h]isoquinoline-1,3(2H)-dione (obtained in example 3) in 4 mL of acetonitrile was stirred at 20° C. 3,4-(methylenedioxy)phenyl isocyanate (2 molar equivalents) in 3 mL acetonitrile were added. The mixture was magnetically stirred at 20° C. during 18 hours. The solvent was then evaporated under reduced pressure and the residue was submitted to a flash chromatography on silica (eluent: $CH_2Cl_2$/methanol in a 95:5 volume ratio) to provide 125 mg (yield: 84%) of the desired product (formula below) as an orange powder.

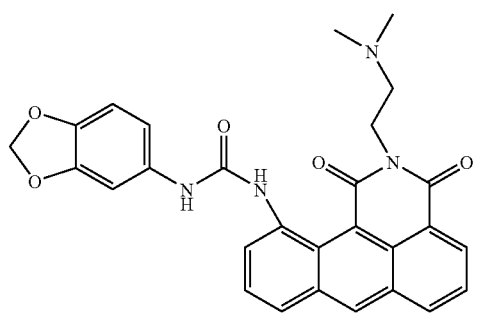

which was characterized as follows:

EIMS: 496(M+); 482; 347; 333; 302; 290; 276; 262; 246; 218; 208; 190; 176; 163; 151; 137; 106; 79; 72; and 58; and $^1$H NMR (300 MHz, $CDCl_3$): 8.86 (H-7, s); 8.74 (H-4, dd, J=7.3 Hz, J=1.5 Hz); 8.37 (H-6, dd, J=8.4 Hz, J=1.1 Hz); 8.09 (H-8, d, J=7.3 Hz, J=1.5 Hz); 7.97 (H10, d, J=8.4 Hz); 7.73 (H-5, dd, J=8.4 and 7.3 Hz); 7.70 (H-9, t, J=7.2 Hz); 7.16 (H-arom, d, J=2.2 Hz); 6.82 (H-arom, dd, J=8.4 Hz, J=2.2 Hz); 6.73 (H-arom, d, J=8.1 Hz); 5.92 (O—$CH_2$—O, s); 4.40 ($CH_2$—N, t, J=7.0 Hz); 2.76 ($CH_2$—N, t, J=7.0 Hz); and 2.38 (N($CH_3$)$_2$, s).

EXAMPLE 13

Preparation of 1-{2-[2-(dimethylamino)ethyl]-1,3-dioxo-2,3-dihydro-1H-dibenzo[de,h]isoquinolin-11-yl}-3-pentylurea A solution of 100 mg (0.30 mmole) of 11-amino-2-[2-(dimethylamino)ethyl]-1H-dibenzo[de,h]isoquinoline-1,3(2H)-dione (obtained in example 3) in 4 mL of acetonitrile was stirred at 20° C. 156 µL (4 molar equivalents) of pentyl isocyanate in 3 mL acetonitrile were added. The mixture was magnetically stirred at 20° C. during 18 hours. The solvent was then evaporated under reduced pressure and the residue was submitted to a flash chromatography on silica (eluent: $CH_2Cl_2$/methanol in a 95:5 ratio) to provide 37 mg (yield: 28%) of the desired product (formula below) as an orange powder

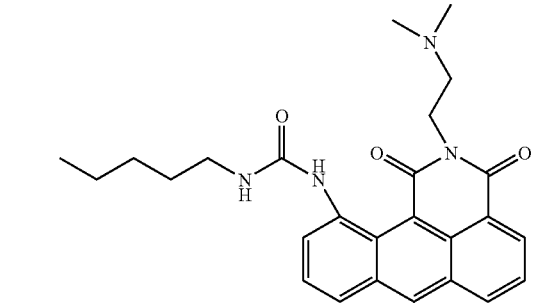

which was characterized as follows:

EIMS: 446(M+); 375; 359; 347; 333; 315; 288; 262; 246; 229; 218; 203; 190; 176; 163; 112; 98; 87; 70; and 58; and $^1$H NMR (300 MHz, $CDCl_3$): 8.88 (N—H, s); 8.77 (H-7, s); 8.74 (H-4, dd, J=7.0 Hz, J=1.1 Hz); 8.32 (H-6, dd, J=8.4 Hz, J=1.1 Hz); 8.07 (H-8, d, J=7.3 Hz, J=1.1 Hz); 7.87 (H-10, d, J=7.7 Hz); 7.72 (H-5, dd, J=8.4 and 7.0 Hz); 7.65 (H-9, t, J=7.5 Hz); 4.82 (N—H, s); 4.43 ($CH_2$—N, t, J=6.7 Hz); 3.24 ($CH_2$—NH, q, J=7.0 Hz); 2.76 ($CH_2$—N, t, J=6.6 Hz); 2.42 (N($CH_3$)$_2$, s); 1.55 (NH—$CH_2$—$CH_2$—, m); 1.33 (4H-alkyl, m); 0.89 ($CH_3$—$CH_2$, m).

EXAMPLE 14

Preparation of 1-(1,3-benzodioxol-5-yl)-3-{2-[2-(dimethylamino)ethyl]-1,3-dioxo-2,3-dihydro-1H-dibenzo[de,h]isoquinolin-8-yl}urea A solution of 100 mg (0.30 mmole) of 8-amino-2-[2-(dimethylamino)ethyl]-1H-dibenzo[de,h]isoquinoline-1,3(2H)-dione (obtained in example 4) in 4 mL of acetonitrile was stirred at 20° C. 3,4-(methylenedioxy)phenyl isocyanate (4 molar equivalents) in 3 mL acetonitrile were added. The mixture was magnetically stirred at 20° C. during 24 hours. The solvent was then evaporated under reduced pressure and the residue was submitted to a flash chromatography on silica (eluent: $CH_2Cl_2$/methanol in a 95:5 volume ratio) to provide 76 mg (yield: 51%). of the desired product (formula below) as an orange powder

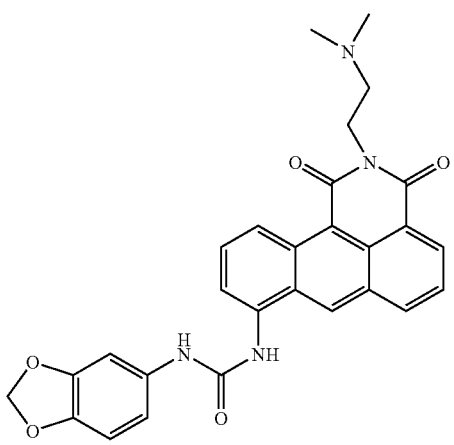

which was characterized by its mass spectrum as follows: 496(M+); 359; 315; 301; 288; 271; 262; 245; 231; 217; 188; 176; 163; 137; 109; 79; 71; 58; and 52.

EXAMPLE 15

Preparation of 1-(1,3-benzodioxol-5-yl)-3-{2-[2-(dimethylamino)ethyl]-1,3-dioxo-2,3-dihydro-1H-dibenzo[de,h]isoquinolin-8-yl}urea hydrochloride A solution 20 mg of the compound of example 14 in 2 mL of diethyl ether was magnetically stirred. 10 μL of HCl 12N in 100 μL of methanol (3 molar equivalents) were added. The resulting precipitate was filtered and dried under reduced pressure. The red solid obtained (yield: 100%; formula below)

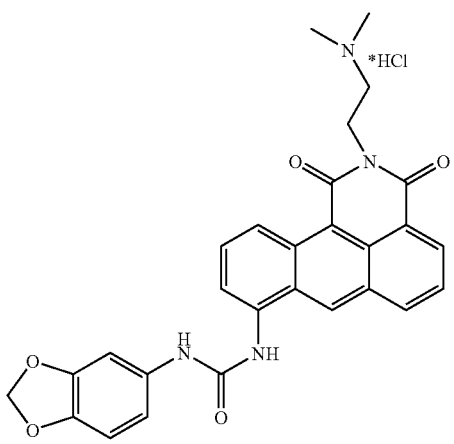

was characterized by NMR $^1$H (CDCl$_3$) as follows: 10.10 (CO—N—H, s); 9.9 (CO—N—H, s); 9.86 (N(CH$_3$)$_2$. HCl, s); 9.58 (1H, d, J=9 Hz); 9.50 (Me$_2$N.HCl, s); 8.66 (2H, m); 8.21 (H-8, d, J=7.2 Hz); 7.88 (2H, q, J=8.1 Hz); 7.33 (1H, s); 6.89 (2H, s); 5.99 (O—CH$_2$—O, s); 4.50 (CH$_2$—N, t, J=5.7 Hz); 3.50 (CH$_2$—N, t, J=5.1 Hz); and 2.93 (N(CH$_3$)$_2$, d, J=4.2 Hz) ppm.

EXAMPLE 16

Preparation of the hydrochloride salt of N-({2-[2-(dimethylamino)ethyl]-1,3-dioxo-2,3-dihydro-1H-dibenzo[de,h]isoquinolin-8-yl}carbamoyl)benzamide hydrochloride A solution of 100 mg (0.30 mmole) of 2-[2-(dimethylamino)ethyl]-8-amino-3H-dibenzo[deh]isoquinoline-1,3 (2H)-dione (obtained in example 4) in 3 mL of acetonitrile was stirred at room temperature. 176 mg (4 molar equivalents) of benzoyl isocyanate in 2 mL acetonitrile were added. The mixture was magnetically stirred at 20° C. during 24 hours. The solvent was then evaporated under reduced pressure and the residue was submitted to a flash chromatography on silica (eluent: CH$_2$Cl$_2$/methanol in a 90:10 volume ratio) to provide 123 mg (yield: 79%) of the desired product as an orange powder.

A solution of 20 mg of this solid powder in 2 mL diethyl ether were magnetically stirred. 10 μL of HCl 12N in 100 μL of methanol (3 eq.) were added. The resulting precipitate was filtered and dried under reduced pressure. The red solid powder obtained (yield: 100%, formula below)

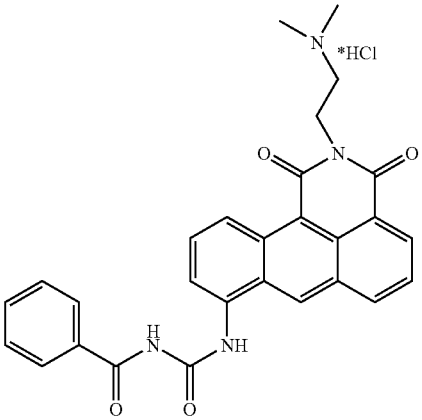

was characterized as follows:

EIMS: 480(M+); 359; 333; 288; 262; 245; 231; 217; 188; 176; 163; 147; 121; 105; 78; 71; and 58;

$^1$H NMR (CDCl$_3$) ppm: 11.49 (CO—N—H, s); 11.39 (CO—N—H, s); 9.75 (2H, m); 9.74 (Me$_2$N.HCl, s); 9.36 (1H, s); 8.69 (2H, m); 8.16 (3H, m); 7.92 (2H arom, m); 7.72 (1H arom., m); 7.61 (2H arom, t, J=7.8 Hz); 4.51 (CH$_2$—N, t, J=5.1 Hz); 3.52 (CH$_2$—N, m); 2.93 (N(CH$_3$)$_2$, 2×s).

EXAMPLE 17

Preparation ethyl {2-[2-(dimethylamino)ethyl]-1,3-dioxo-2,3-dihydro-1H-dibenzo[de,h]isoquinolin-11-yl}carbamate To a solution of 100 mg (0.30 mmole) of 11-amino-2-[2-(dimethylamino)ethyl]-1H-dibenzo[de,h]isoquinoline-1,3 (2H)-dione (obtained in example 3), in 5 mL of dichloromethane, 57 μL of ethyl chloroformate and 85 μL (2 eq) of triethylamine were added. The mixture was magnetically stirred at 20° C. during 4 hours. The solvent was then evaporated under reduced pressure and the residue was submitted to a flash chromatography on silica (eluent: CH$_2$Cl$_2$/methanol in a 97:3 volume ratio) to provide 111 mg (yield: 83%) of the desired product (formula below) as an orange powder.

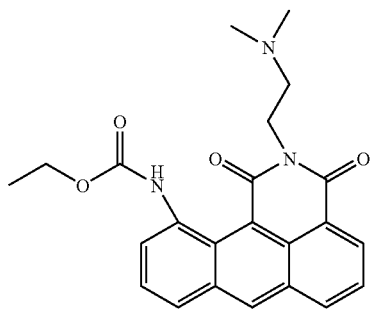

which was characterized as follows:

EIMS: 405(M+); 359; 334; 315; 288; 262; 246; 218; 203; 90; 177; 63; 71; and 58;

$^1$H NMR (300 MHz, CDCl$_3$): 9.22 (N—H, s); 8.82 (H-7, s); 8.74 (H-4, dd, J=7.0 Hz, J=1.5 Hz); 8.33 (H-6, dd, J=7.2 Hz, J=1.1 Hz); 8.10 (H-8, d, J=7.3 Hz); 7.94 (H-10, d, J=7.7 Hz); 7.71 (H-5, dd, J=7.4 and 7.2 Hz); 7.68 (H-9, t, J=7.8 Hz); 4.48 (CH$_2$—N, t, J=6.6 Hz); 4.20 (O—CH$_2$—CH$_3$, q, J=7.3 Hz); 2.79 (CH$_2$—N, t, J=6.6 Hz); 2.36 (N(CH$_3$)$_2$, s); and 1.32 (CH$_2$—CH$_3$, t, J=7.0 Hz); and $^{13}$C NMR (75.4 MHz, CDCl$_3$): 166.8; 163.6; 155.2; 137.6; 134.8; 133.8; 133.2; 128.9; 128.1; 127.6; 127.3; 126.7; 125.5; 122.2; 61.0; 57.2; 45.7; 39.0; 14.6.

EXAMPLE 18

Preparation phenyl {2-[2-(dimethylamino)ethyl]-1,3-dioxo-2,3-dihydro-1H-dibenzo[de,h]isoquinolin-11-yl}carbamate To a solution of 100 mg (0.30 mmole) of 11-amino-2-[2-(dimethylamino)ethyl]-1H-dibenzo[de,h]isoquinoline-1,3 (2H)-dione (obtained in example 3), in 5 mL of dichloromethane, 75 µL of phenyl chloroformate and 85 µL (2 molar equivalents) of triethylamine were added. The mixture was magnetically stirred at 20° C. during 3 hours. The solvent was then evaporated under reduced pressure and the residue was submitted to a flash chromatography on silica (eluent: CH$_2$Cl$_2$/methanol in a 97:3 volume ratio) to provide 94 mg (yield: 69%) of the desired product (formula below) as a red powder.

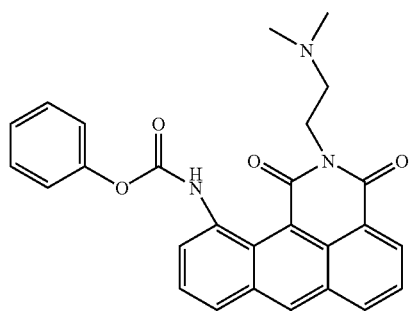

which was characterized as follows:

EIMS: 359; 315; 288; 258; 245; 215; 188; 176; 163; 94; 71; and 58;

NMR $^1$H (CDCl$_3$) ppm: 9.77 (N—H, s); 8.88 (H-7, s); 8.78 (H-4, dd, J=7.0 Hz, J=1.1 Hz); 8.37 (H-6, dd, J=7.2 Hz, J=1.1 Hz); 8.17 (H-8, d, J=7.3 Hz); 8.00 (H-10, d, J=7.3 Hz); 7.73 (H-5, dd, J=6.9 and 7.2 Hz); 7.70 (H-9, t, J=7.8 Hz); 7.37 (H-aro, td, J=7.7 Hz, J=1.1 Hz); 7.20 (H-aro, td, J=5.5 Hz, J=2.2 Hz); 4.51 (CH$_2$—N, t, J=6.6 Hz); 2.80 (CH$_2$—N, t, J=6.6 Hz); and 2.36 (N(CH$_3$)$_2$, s); and NMR $^{13}$C(CDCl$_3$) ppm 167.0; 163.5; 153.3; 150.9; 137.8; 134.9; 134.3; 133.8; 132.7; 129.2; 129.1; 128.2; 127.8; 127.6; 126.7; 125.7; 125.3; 122.3; 121.7; 116.5; 57.4; 45.8; and 39.2.

EXAMPLE 19

Preparation of 5-(1-hydroxydecylidene)-2,2-dimethyl-1,3-dioxane-4,6-dione

Synthesis proceeds according to the scheme shown below:

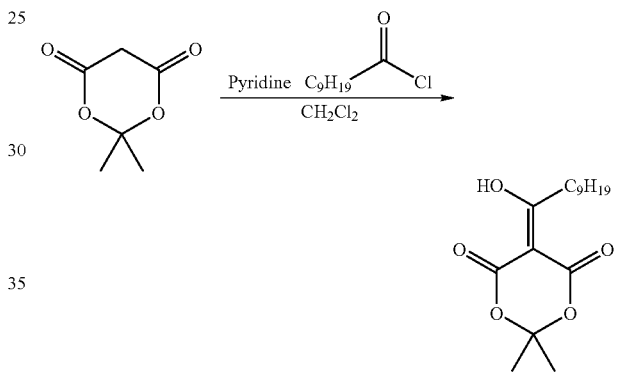

To a cooled solution (0° C.) of 360 mg (2.5 mmoles) 2,2-dimethyl-1,3-dioxane-4,6-dione in 3 mL of dichloromethane under argon atmosphere were added 460 µL (2.2 molar equivalents) pyridine and 520 µL (1.1 molar equivalent) decanoyl chloride. The solution was stirred at 0° C. for 1 hour (after which time it became yellow) and then 18 hours at 20° C. Then the organic layer was washed with diluted iced HCl (1N) and was evaporated to give the desired product (formula above) as a brown oil (700 mg) which was used in the next reaction step without further purification.

EXAMPLE 20

Preparation of N-{2-[2-(dimethylamino)ethyl]-1,3-dioxo-2,3-dihydro-1H-dibenzo[de,h]isoquinolin-11-yl}-3-oxododecanamide To a solution of 100 mg (0.30 mmole) of 11-amino-2-[2-(dimethylamino)ethyl]-1H-dibenzo[de,h]isoquinoline-1,3 (2H)-dione (obtained in example 3) in 8 mL of toluene, magnetically stirred at 20° C., 103 mg of the compound of example 19 were added. The mixture was refluxed during 2.5 hours, and then allowed to cool to 20° C. The solvent was then evaporated under reduced pressure and the residue was submitted to a flash chromatography on silica (eluent: CH$_2$Cl$_2$/methanol in a 97:3 volume ratio) to provide 79 mg (yield: 63%) of the desired product (formula below) as a red powder.

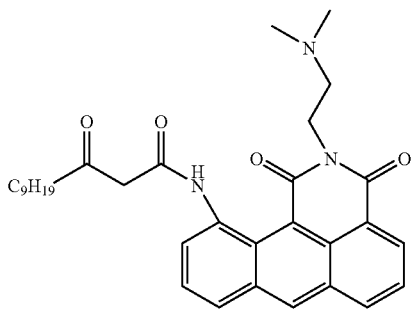

which was characterized as follows:

EIMS: 489(M+); 418; 315; 288; 262; 246; 218; 190; 163; 84; and 71;

NMR $^1$H (CDCl$_3$) ppm: 10.38 (N—H, s); 8.85 (H-7, s); 8.77 (H-4, dd, J=7.3 Hz, J=1.5 Hz); 8.35 (H-6, dd, J=8.4 Hz, J=1.1 Hz); 8.17 (H-8, d, J=7.4 Hz); 8.00 (H-10, d, J=8.1 Hz); 7.75 (H-5, dd, J=7.4 and 7.2 Hz); 7.69 (H-9, t, J=7.8 Hz); 4.48 (CH$_2$—N, t, J=7.0 Hz); 3.58 (CO—CH$_2$—CO, s); 2.81 (CH$_2$—CH$_2$—CO, t, J=7.3 Hz); 2.64 (CH$_2$—N, t, J=7.4 Hz); 2.44 (N(CH$_3$)$_2$, s); 1.61 (CH$_2$—CH$_2$—CO, t, J=7.2 Hz); 1.22 (H-ali, m); and 0.88 (CH$_3$, m); and NMR $^{13}$C (CDCl$_3$) ppm 204.8; 166.2; 164.9; 163.6; 137.6; 135.0; 134.3; 133.8; 132.1; 129.3; 129.1; 128.3; 128.2; 127.5; 126.6; 125.6; 122.1; 116.5; 56.7; 52.1; 45.3; 43.4; 38.9; 35.4; 31.8; 29.4; 29.2; 29.0; 25.0; 23.4; 22.6; and 14.1.

EXAMPLE 21

Preparation of 5-(1-hydroxy-3-phenylpropylidene)-2,2-dimethyl-1,3-dioxane-4,6-dione Synthesis proceeds according to the scheme shown below, wherein Ph means phenyl:

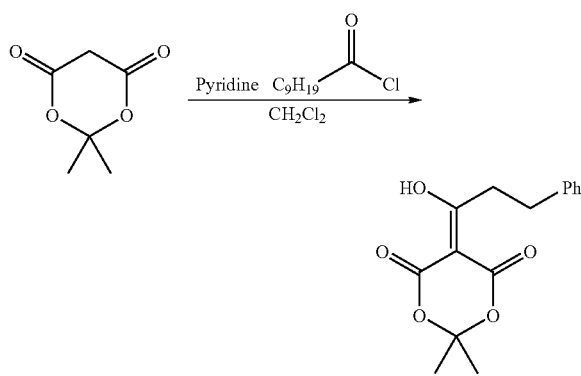

To a cooled solution (0° C.) of 360 mg (2.5 mmoles) 2,2-dimethyl-1,3-dioxane-4,6-dione in 3 mL of dichloromethane under argon atmosphere were added 440 μL of (2.1 molar equivalent) pyridine and 407 μL (1.1 molar equivalent) of hydroxycinna-moyl chloride. The solution was stirred at 0° C. for 1 hour (aftzer which time it became yellow) and then 18 hours at 20° C. Then the organic layer was washed with diluted iced HCl (1N) and was evaporated to provide the desired product (formula above) as a brown oil (640 mg) which was used in the next reaction step without further purification.

EXAMPLE 22

Preparation of N-{2-[2-(dimethylamino)ethyl]-1,3-dioxo-2,3-dihydro-1H-dibenzo[de,h]isoquinolin-11-yl}-3-oxo-5-phenylpentanamide To a solution of 100 mg (0.30 mmole) of 11-amino-2-[2-(dimethylamino)ethyl]-1H-dibenzo[de,h]isoquinoline-1,3 (2H)-dione (obtained in example 3) in 8 mL of toluene, magnetically stirred at 20° C., 95 mg of the compound of example 21 were added. The mixture was refluxed during 4.5 hours and then allowed to cool to 20° C. The solvent was then evaporated under reduced pressure and the residue was submitted to a flash chromatography on silica (eluent: CH$_2$Cl$_2$/methanol in a 97:3 volume ratio) to provide 81 mg (yield: 53%) of the desired product (formula below) as a red powder.

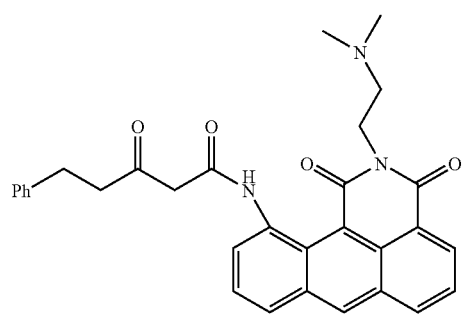

which was characterized as follows:

EIMS: 507(M+); 465; 436; 333; 262; 190; 164; 105; 91; 71; and 58;

NMR $^1$H (CDCl$_3$) ppm: 10.39 (N—H, s); 8.85 (H-7, s); 8.77 (H-4, dd, J=7.0 Hz, J=1.5 Hz); 8.35 (H-6, dd, J=7.8 Hz, J=0.7 Hz); 8.12 (H-8, d, J=7.0 Hz); 8.01 (H-10, d, J=8.1 Hz); 7.75 (H-5, dd, J=7.4 and 7.2 Hz); 7.69 (H-9, t, J=7.8 Hz); 7.20 (H-arom, m); 4.47 (CH$_2$—N, t, J=6.6 Hz); 3.58 (CO—CH$_2$—CO, s); 2.96 (Ph-CH$_2$—CH$_2$—CO, m); 2.74 (CH$_2$—N, t, J=6.7 Hz); and 2.40 (N(CH$_3$)$_2$, s);

NMR $^{13}$C (CDCl$_3$) ppm 203.4; 166.7; 164.7; 163.5; 140.5; 137.9; 135.1; 134.5; 133.8; 131.8; 129.5; 129.1; 128.5; 128.4; 128.2; 128.1; 127.6; 126.5; 126.1; 125.7; 122.1; 116.3; 57.0; 52.2; 45.7; 44.8; and 39.4.

EXAMPLE 23

Preparation of ethyl 6-({2-[2-(dimethylamino)ethyl]-1,3-dioxo-2,3-dihydro-1H-dibenzo[de,h]isoquinolin-11-yl}amino)-4,6-dioxohexanoate 100 mg of 11-amino-2-[2-(dimethylamino)ethyl]-1H-dibenzo[de,h]isoquinoline-1,3(2H)-dione (obtained in example 3) (0.30 mmol), 7 mL of toluene and 70 mg of ethyl 4-(2,2-dimethyl-4,6-dioxo-1,3-dioxan-5-ylidene)-4-hydroxybutanoate (1.1 molar equivalent) were refluxed for 6 hours. After cooling, the solvent was evaporated under reduced pressure and the residue was submitted to a flash chromatography on silica (eluent: CH$_2$Cl$_2$/methanol in a 97:3 volume ratio) to provide 48 mg yield=29% of the desired product (formula below) as a red powder.

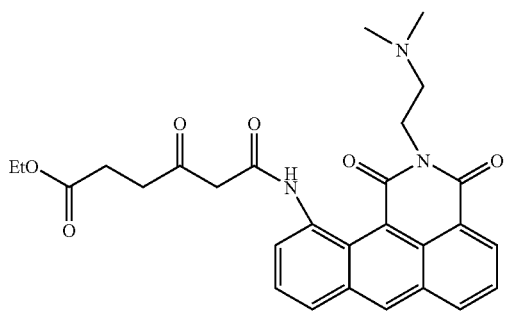

which was characterized as follows:

EIMS: 503(M+); 458; 432; 404; 333; 262; 190; 101; 71; and 58; and

NMR $^1$H (CDCl$_3$) ppm: 10.41 (N—H, s); 8.84 (H-7, s); 8.76 (H-4, dd, J=7.3 Hz, J=1.5 Hz); 8.35 (H-6, dd, J=7.8 Hz, J=0.7 Hz); 8.14 (H-8, d, J=7.3 Hz); 8.00 (H-10, d, J=8.1 Hz); 7.77 (H-5, dd, J=7.5 and 7.7 Hz); 7.70 (H-9, t, J=7.5 Hz); 4.46 (CH$_2$—N, t, J=7.0 Hz); 4.09 (CH$_3$—CH$_2$O, q, J=7.0 Hz); 3.64 (CO—CH$_2$—CO, s); 2.96 (CO—CH$_2$—CH$_2$—CO, t, J=6.6 Hz); 2.75 (CH$_2$—N, t, J=7.0 Hz); 2.60 (CO—CH$_2$—CH$_2$—CO, t, J=6.6 Hz); 2.40 (N(CH$_3$)$_2$, s); and 1.22 (CH$_3$—CH$_2$O, t, J=7.3 Hz).

EXAMPLE 24

Preparation of 4-fluorophenyl {2-[2-(dimethylamino)ethyl]-1,3-dioxo-2,3-dihydro-1H-dibenzo[de,h]isoquinolin-11-yl}carbamate 100 mg of 11-amino-2-[2-(dimethylamino)ethyl]-1H-dibenzo[de,h]isoquinoline-1,3(2H)-dione (obtained in example 3) (0.30 mmol) were dissolved in 6 ml of dichloromethane. 85 μl (2 molar equivalents) of triethylamine and 105 mg (2 molar equivalents) of 4-fluorophenyl chloroformate were respectively added. The reaction mixture was maintained at 20° C. for 3 hours. The solvent was then evaporated under reduced pressure and the residue was submitted to a flash chromatography on silica, (eluent: CH$_2$Cl$_2$/methanol in a 95/5 volume ratio) to provide 103 mg (yield=66%) of the desired product (formula below) as an orange powder.

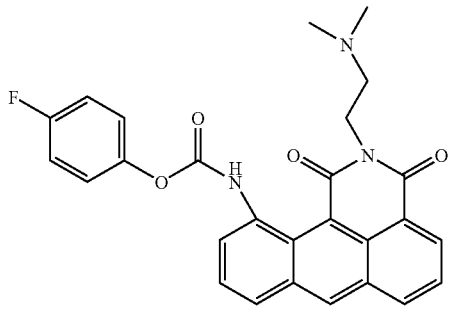

which was characterized as follows:

MS: 471 (M+), 391, 384, 359, 190, 112, 83, and 71;

NMR $^1$H (CDCl$_3$) ppm: 9.22 (N—H, s); 8.89 (H-7, s); 8.79 (H-4, dd, J=6.9 Hz, J=1.5 Hz); 8.37 (H-6, dd, J=7.4 Hz, J=0.9 Hz); 8.17 (H-8, d, J=7.2 Hz); 8.01 (H-10, d, J=7.8 Hz); 7.77 (H-5, dd, J=6.9 and 7.7 Hz); 7.70 (H-9, t, J=7.2 Hz); 4.50 (CH$_2$—N, t, J=6.9 Hz); 2.77 (CH$_2$—N, t, J=6.6 Hz); and 2.35 (N(CH$_3$)$_2$, s); and NMR $^{13}$C (CDCl$_3$) ppm: 166.6; 164.0; 158.5; 153.6; 146.9; 137.8; 135.3; 134.5; 134.0; 132.7; 129.2; 128.5; 128.0; 127.6; 126.9; 125.9; 123.3; 123.2; 122.3; 116.1; 115.8; 57.1; 45.6; and 38.9.

EXAMPLE 25

Preparation of octyl {2-[2-(dimethylamino)ethyl]-1,3-dioxo-2,3-dihydro-1H-dibenzo[de,h]isoquinolin-11-yl}carbamate 100 mg of 11-amino-2-[2-(dimethylamino)ethyl]-1H-dibenzo[de,h]isoquinoline-1,3(2H)-dione (obtained in example 3) (0.30 mmol) were dissolved in 6 ml dichloromethane. 85 μl (2 molar equivalents) of triethylamine and 127 mg (2 molar equivalents) of octyl chloroformate were respectively added. The reaction mixture was maintained at 20° C. for 3 hours. The solvent was then evaporated under reduce pressure and the residue was submitted to a flash chromatography on silica (eluent: CH$_2$Cl$_2$/methanol in a 95/5 volume ratio) to provide 137 mg (yield=85%) of the desired product (formula below) as an orange powder.

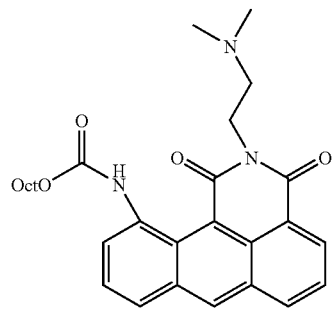

which was characterized as follows:

MS: 489(M+), 418, 315, 288, 262, 246, 218, 190, 163, and 71;

NMR $^1$H (CDCl$_3$) ppm: 9.22 (N—H, s); 8.85 (H-7, s); 8.75 (H-4, dd, J=7.0 Hz, J=1.5 Hz); 8.34 (H-6, dd, J=8.4 Hz, J=1.1 Hz); 8.10 (H-8, d, J=7.3 Hz); 7.96 (H, d, J=7.3 Hz); 7.73 (H-5, dd, J=6.9 and 8.4 Hz); 7.68 (H-9, t, J=7.2 Hz); 4.47 (CH$_2$—N, t, J=7.0 Hz); 4.12 (CH$_2$—O, t, J=7 Hz); 2.75 (CH$_2$—N, t, J=7.0 Hz); 2.40 (N(CH$_3$)$_2$, s); 1.67 (CH$_2$—CH$_2$—O, m); 1.28 (10H, m); and 0.88 (CH$_3$—CH$_2$, t, J=7.0 Hz); and NMR $^{13}$C (CDCl$_3$) ppm: 166.8; 163.5; 155.3; 137.6; 134.8; 134.1; 133.2; 128.9; 128.1; 128.1; 127.3; 126.7; 125.5; 122.2; 65.3; 57.2; 45.8; 39.1; 31.7; 29.2; 29.2; 29.0; 22.6; and 14.0.

EXAMPLE 26

Preparation of allyl {2-[2-(dimethylamino)ethyl]-1,3-dioxo-2,3-dihydro-1H-dibenzo[de,h]isoquinolin-11-yl}carbamate 100 mg of 11-amino-2-[2-(dimethylamino)ethyl]-1H-dibenzo[de,h]isoquinoline-1,3(2H)-dione (obtained in example 3) (0.30 mmol) were dissolved in 6 ml dichloromethane. 85 μl (2 molar equivalents) triethylamine and 65 μl (2 molar equivalents) of allyl chloroformate were added. The reaction mixture was stirred at 20° C. for 3 hours. The solvent was then evaporated under reduced pressure and the residue was submitted to a flash chromatography on silica (eluent: CH$_2$Cl$_2$/methanol in a 95/5 volume ratio) to provide 70 mg (yield=51%) of the desired product (formula below) as an orange powder.

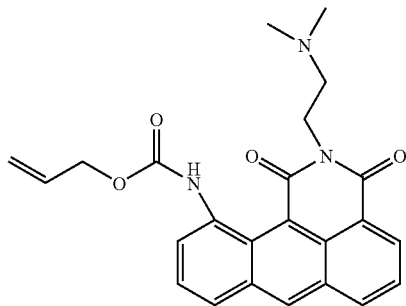

which was characterized as follows:

MS: 417 (M+), 346, 315, 288, 262, 246, 218, 190, 177, 163, and 71;

NMR $^1$H (CDCl$_3$) ppm: 9.33 (N—H, s); 8.84 (H-7, s); 8.74 (H-4, dd, J=7.0 Hz, J=1.1 Hz); 8.33 (H-6, dd, J=8.4 Hz, J=1.1 Hz); 8.10 (H-8, d, J=7.3 Hz); 7.96 (H-10, d, J=7.3 Hz); 7.73 (H-5, dd, J=7.0 and 8.4 Hz); 7.68 (H-9, t, J=7.3 Hz); 5.97 (CH$_2$=CH, m); 5.35 (CH$_2$=CH, dd, J=17.2 Hz, J=1.5 Hz); 5.23 (CH$_2$=CH, dd, J=10.3 Hz, J=1.1 Hz); 4.64 (O—CH$_2$, dt, J=5.9 Hz, J=1.1 Hz); 4.46 (CH$_2$—N, t, J=7.0 Hz); 2.74 (CH$_2$—N, t, J=7.0 Hz) and 2.38 (N(CH$_3$)$_2$, s); and NMR $^{13}$C (CDCl$_3$) ppm: 166.9; 154.9; 137.7; 134.8; 134.2; 133.8; 132.8; 129.0; 128.1; 127.6; 127.5; 126.7; 125.6; 122.2; 117.91; 116.5; 65.8; 57.0; 28; 45.8; and 39.1.

EXAMPLE 27

Preparation of isobutyl {2-[2-(dimethylamino)ethyl]-1,3-dioxo-2,3-dihydro-1H-dibenzo[de,h]isoquinolin-11-yl}carbamate

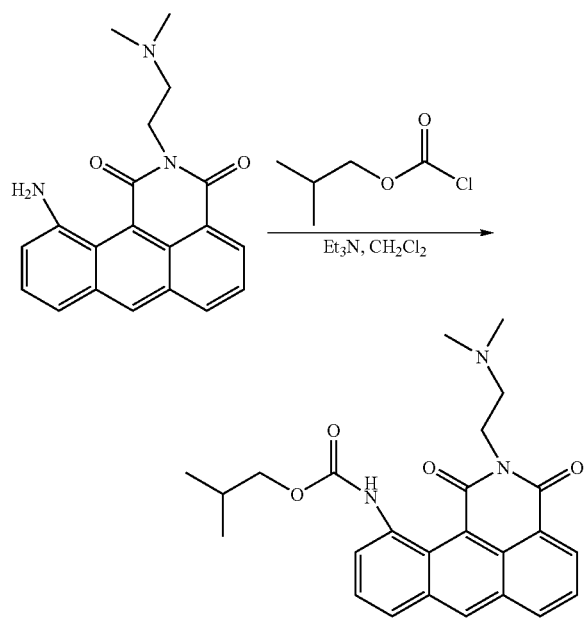

100 mg of 11-amino-2-[2-(dimethylamino)ethyl]-1H-dibenzo[de,h]isoquinoline-1,3(2H)-dione (obtained in example 3) (0.30 mmole) were dissolved in 6 ml of dichloromethane. 85 µl (2 molar equivalent) of triethylamine and 78 µl (2 molar equivalent) of isobutyl chloroformate were respectively added. The reaction mixture was maintained at room temperature for 3 hours. The solvent was then evaporated under reduced pressure and the residue was submitted to a flash chromatography (SiO2, CH2Cl2/MeOH 95/5) to provide 92 mg (yield=7%) of the desired product (formula shown hereinabove) as an orange powder which was characterized as follows:

ESIMS (+°): 434, 389.

NMR $^1$H (CDCl$_3$) ppm: 9.26 (N—H, s); 8.85 (H-7, s); 8.76 (H-4, dd, J=7.0 Hz, J=1.5 Hz); 8.34 (H-6, dd, J=8.4 Hz, J=1.1 Hz); 8.10 (H-8, d, J=7.3 Hz); 7.96 (H-10, d, J=8.4 Hz); 7.74 (H-5, dd, J=7.3 Hz, J=8.4 Hz); 7.69 (H-9, t, J=8.0 Hz); 4.46 (CH$_2$—N, t, J=7.0 Hz); 3.91 (CH$_2$—O, d, J=6.6 Hz); 2.75 (CH$_2$—N, t, J=7.0 Hz); 2.40 (N(CH$_3$)$_2$, s); 1.99 (Me-CH-Me, m); 0.99 (CH$_3$—, s); and 0.96 (CH$_3$—, s); and NMR $^{13}$C (CDCl$_3$) ppm: 166.8; 163.6; 155.3; 137.7; 134.9; 134.2; 133.8; 133.3; 129.0; 128.1; 127.7; 127.4; 126.7; 125.6; 122.6; 116.5; 57.2; 45.8; 39.2; 28.0; and 19.2.

EXAMPLE 28

Preparation of 4-chlorobutyl {2-[2-(dimethylamino)ethyl]-1,3-dioxo-2,3-dihydro-1H-dibenzo[de,h]isoquinolin-11-yl}carbamate

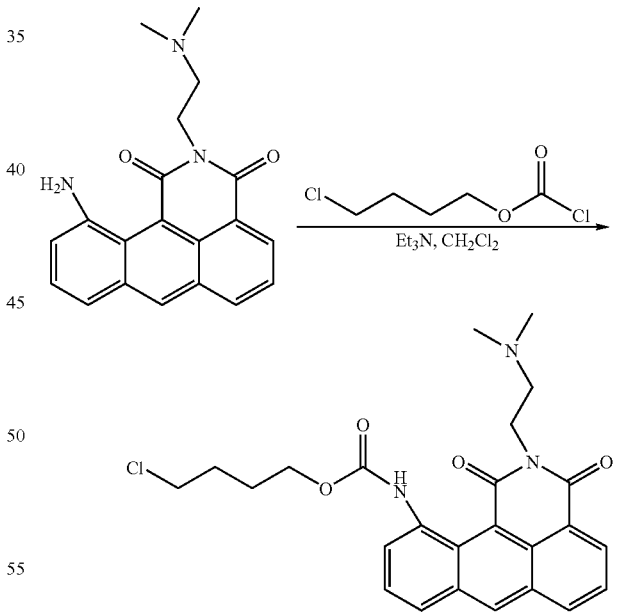

100 mg of 11-amino-2-[2-(dimethylamino)ethyl]-1H-dibenzo[de,h]isoquinoline-1,3(2H)-dione (obtained in example 3) (0.30 mmole) were dissolved in 6 ml of dichloromethane. 85 µl (2 molar equivalents) of triethylamine and 82 µl (2 molar equivalents) of 4-chlorobutyl chloroformate were respectively added. The reaction mixture was maintained at room temperature for 3 hours. The solvent was then evaporated under reduced pressure and the residue was submitted to a flash chromatography (SiO2, CH2Cl2/MeOH 95/5). 119 mg of the desired product (formula shown hereinabove) were isolated as an orange powder (yield=85%) which was characterized as follows:

ESIMS (+°): 468, and 434;

NMR $^1$H (CDCl$_3$) ppm: 9.30 (N—H, s); 8.86 (H-7, s); 8.76 (H-4, dd, J=7.0 Hz, J=1.1 Hz); 8.35 (H-6, dd, J=8.8 Hz, J=1.5 Hz); 8.10 (H-8, d, J=7.3 Hz); 7.98 (H-10, d, J=7.7 Hz); 7.75 (H-5, dd, J=7.0 Hz, J=8.1 Hz); 7.70 (H-9, t, J=8.1 Hz); 4.47 (CH$_2$—N, t, J=6.6 Hz); 4.17 (CO—O—CH$_2$, t, J=6.2 Hz); 3.59 (Cl—CH$_2$, t, J=6.2 Hz); 2.75 (CH$_2$—N, t, J=7.0 Hz); 2.40 (N(CH$_3$)$_2$, s); and 1.88 (—CH$_2$—CH$_2$—, m); and NMR $^{13}$C (CDCl$_3$) ppm: 166.9; 163.5; 155.0; 137.7; 134.9; 134.2; 133.9; 133.1; 129.1; 128.2; 127.7; 127.5; 126.8; 125.6; 122.3; 116.5; 64.2; 57.2; 45.8; 44.5; 39.2; 29.1; and 26.5.

EXAMPLE 29

Preparation of n-butyl {2-[2-(dimethylamino)ethyl]-1,3-dioxo-2,3-dihydro-1H-dibenzo[de,h]isoquinolin-11-yl}carbamate

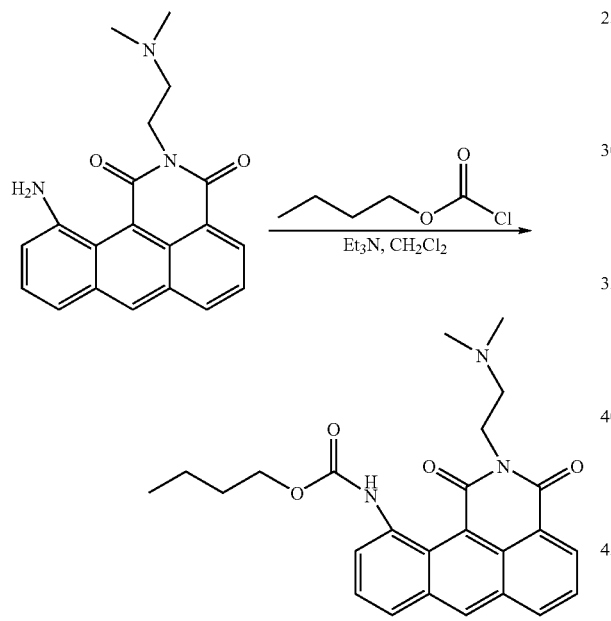

100 mg of 11-amino-2-[2-(dimethylamino)ethyl]-1H-dibenzo[de,h]isoquinoline-1,3(2H)-dione (obtained in example 3) (0.30 mmole) were dissolved in 6 ml of dichloromethane. 85 μl (2 molar equivalents) of triethylamine and 77 μl (2 molar equivalents) of butyl chloroformate were respectively added. The reaction mixture was maintained at room temperature for 3 hours. The solvent was then evaporated under reduced pressure and the residue was submitted to a flash chromatography (SiO2, CH2Cl2/MeOH 95/5). 119 mg of the desired product the desired product (formula shown hereinabove) were isolated as an orange powder (yield=83%) which was characterized as follows:

ESIMS (+°): 434; and 389;

NMR $^1$H (CDCl$_3$) ppm: 9.23 (N—H, s); 8.77 (H-7, s); 8.71 (H-4, dd, J=7.0 Hz, J=1.1 Hz); 8.28 (H-6, dd, J=8.8 Hz, J=1.1 Hz); 8.09 (H-8, d, J=7.3 Hz); 7.90 (H-10, d, J=8.4 Hz); 7.70 (H-5, dd, J=7.3 Hz, J=8.4 Hz); 7.65 (H-9, t, J=7.7 Hz); 4.46 (CH$_2$—N, t, J=7.0 Hz); 4.14 (CO—O—CH$_2$, t, J=6.6 Hz); 2.75 (CH$_2$—N, t, J=7.0 Hz); 2.40 (N(CH$_3$)$_2$, s); 1.68 (O—CH$_2$—CH$_2$, m); 1.43 (CH$_3$—CH$_2$—, m); and 0.96 (CH$_3$—, t, J=7.3 Hz); and NMR $^{13}$C (CDCl$_3$) ppm: 166.8; 163.6; 155.3; 137.7; 134.8; 134.1; 133.8; 133.3; 129.0; 128.1; 127.7; 127.3; 126.7; 125.6; 122.3; 116.5; 65.0; 57.2; 45.8; 39.1; 31.1; 19.1; and 13.8.

EXAMPLE 30

Preparation of 1-{2-[2-(dimethylamino)ethyl]-1,3-dioxo-2,3-dihydro-1H-dibenzo[de,h]isoquinolin-11-yl}-3-[4-bromophenyl]thiourea

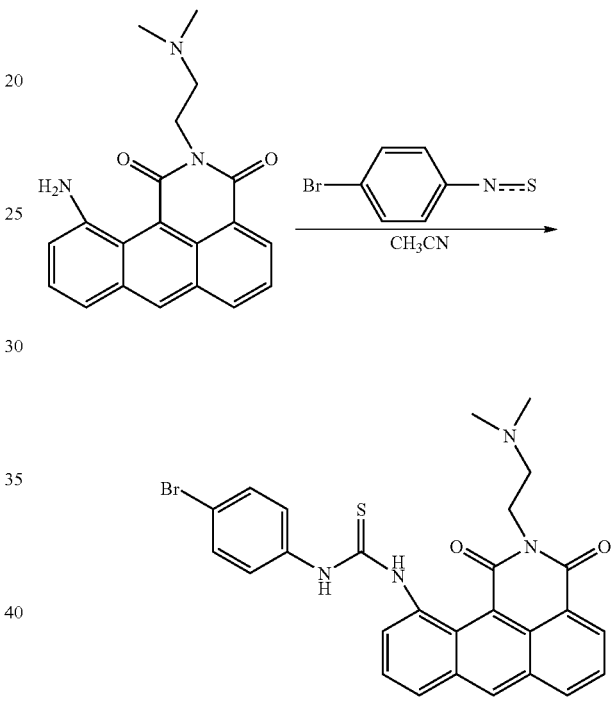

100 mg of 11-amino-2-[2-(dimethylamino)ethyl]-1H-dibenzo[de,h]isoquinoline-1,3(2H)-dione (obtained in example 3) (0.30 mmole) were dissolved in 6 ml of acetonitrile. 128 μl (2 molar equivalents) of 4-bromophenyl isothiocyanate was added and the reaction mixture was maintained at room temperature for 16 hours. The solvent was then evaporated under reduced pressure and the residue was submitted to a flash chromatography (SiO2, CH2Cl2/MeOH 95/5). 147 mg of the desired product (formula shown hereinabove) were isolated as a red powder (yield=90%) which was characterized as follows:

ESIMS (+°): 547-549, 531-533, 334.1; and

NMR $^1$H (CDCl$_3$+MeOD): 8.99 (H-7, s); 8.75 (H-4, dd, J=7.0 Hz, J=1.1 Hz); 8.28 (H-6, dd, J=8.4 Hz, J=0.7 Hz); 8.19 (H-8, d, J=7.7 Hz); 8.10 (H-10, d, J=7.3 Hz); 7.80 (H-5, dd, J=7.3 Hz, J=8.4 Hz); 7.76 (H-9, t, J=7.7 Hz); 7.51 (H-arom, d, J=8.8 Hz); 7.39 (H-arom, d, J=8.4 Hz); 4.24 (CH$_2$—N, t, J=7.0 Hz); 2.67 (CH$_2$—N, t, J=7.0 Hz); and 2.33 (N(CH$_3$)$_2$, s).

EXAMPLE 31

Preparation of 1-{2-[2-(dimethylamino)ethyl]-1,3-dioxo-2,3-dihydro-1H-dibenzo[de,h]isoquinolin-11-yl}-3-[4-(trifluoromethoxy)phenyl]thiourea

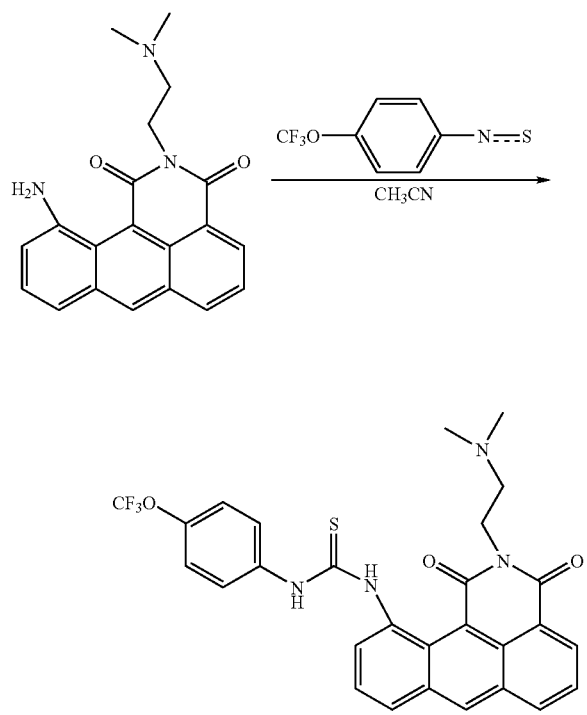

100 mg of 11-amino-2-[2-(dimethylamino)ethyl]-1H-dibenzo[de,h]isoquinoline-1,3(2H)-dione (obtained in example 3) (0.30 mmole) were dissolved in 6 ml of acetonitrile. 97 μl (2 molar equivalents) of 4-(trifluoromethoxy)phenyl isothiocyanate was added and the reaction mixture was maintained at room temperature for 16 hours. The solvent was then evaporated under reduced pressure and the residue was submitted to a flash chromatography (SiO2, CH2Cl2/MeOH 95/5). 151 mg of the desired product (formula shown hereinabove) were isolated as a red powder (yield=91%) which was characterized as follows:

ESIMS (+): 553.0; 334.1; 289.1; 219.9; and 167.5;

NMR $^1$H (DMSO) ppm: 10.31 (—NH—CS—NH—, s); 9.99 (—NH=S—NH—, s); 9.26 (H-arom, s); 8.60 (H-arom, t, J=7.0 Hz); 8.27 (H-arom, d, J=8.0 Hz); 7.94 (H-arom, d, J=7.0 Hz); 7.81 (H-arom, m); 7.65 (H-arom, d, J=8.8 Hz); 7.32 (H-arom, d, J=8.4 Hz); 4.16 (—CH$_2$—N—, t, J=6.6 Hz); 2.50 (—CH$_2$—N—, t); and 2.11 (N(CH$_3$)$_2$, s); and NMR $^{13}$C (DMSO): 179.8; 164.2; 162.8; 144.4; 144.3; 138.5; 137.1; 135.1; 134.2; 133.5; 133.4; 132.1; 129.3; 128.1; 128.0; 127.6; 126.4; 125.9; 124.5; 121.7; 121.6; 121.1; 118.3; 116.6; 56.3; 54.8; and 45.1.

EXAMPLE 32

Preparation of 1-{2-[2-(dimethylamino)ethyl]-1,3-dioxo-2,3-dihydro-1H-dibenzo[de,h]isoquinolin-11-yl}-3-[2-methoxyethyl]thiourea

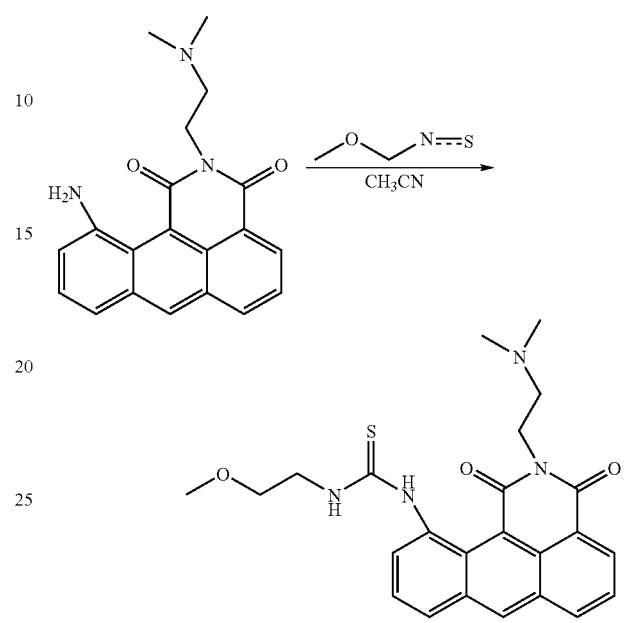

100 mg of 11-amino-2-[2-(dimethylamino)ethyl]-1H-dibenzo[de,h]isoquinoline-1,3(2H)-dione (obtained in example 3) (0.30 mmole) were dissolved in 6 ml of acetonitrile. 170 μl (5 molar equivalents) of 2-methoxyethyl isothiocyanate was added and the reaction mixture was maintained at 60° C. for 16 hours. The solvent was then evaporated under reduced pressure and the residue was submitted to a flash chromatography (SiO2, CH2Cl2/MeOH 95/5). 125 mg of the desired product (formula shown hereinabove) were isolated as a red powder (yield=93%) which was characterized as follows:

ESIMS (+°): 451.2; 334.1;

NMR $^1$H (CDCl$_3$) ppm: 9.56 (N—H, s); 9.25 (H-7, s); 8.60 (2H, m); 8.27 (H-6, dd, J=5.7 Hz, J=1.8 Hz); 7.70-7.90 (4H, m, H-8, H-10, H-5, H-9); 4.26 (CH$_2$—N, t, J=7.0 Hz); 3.54 (CO—CH$_2$, t, J=6.9 Hz); 3.21 (CO—CH$_3$, s); 2.65 (CH$_2$—N, t, J=6.9 Hz); and 2.23 (N(CH$_3$)$_2$, s).

EXAMPLE 33

Preparation of 1-{2-[2-(dimethylamino)ethyl]-1,3-dioxo-2,3-dihydro-1H-dibenzo[de,h]isoquinolin-11-yl}-3-[4-isopropylphenyl]thiourea

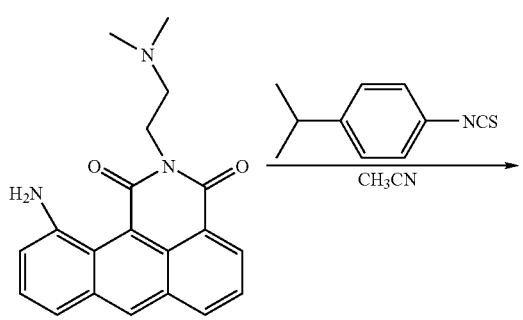

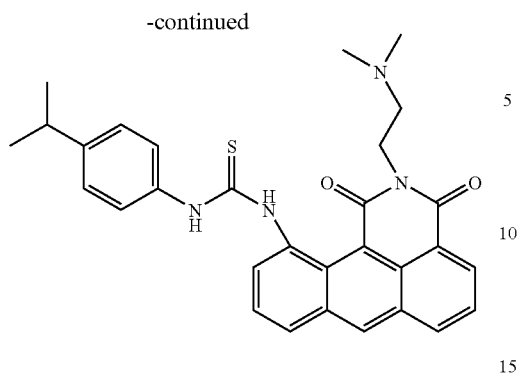

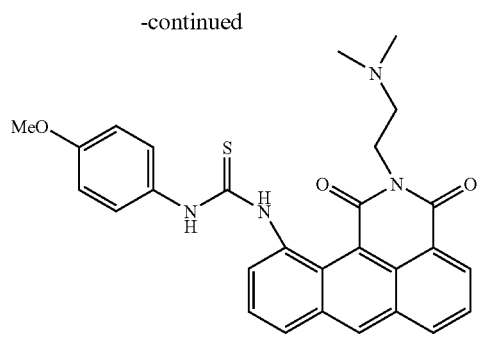

300 mg of 11-amino-2-[2-(dimethylamino)ethyl]-1H-dibenzo[de,h]isoquinoline-1,3(2H)-dione (obtained in example 3) (0.90 mmole) were dissolved in 20 ml of acetonitrile. 309 µl (2 molar equivalents) of 4-isopropylphenyl isothiocyanate was added and the reaction mixture was maintained at room temperature for 16 hours. Two more equivalents of 4-isopropylphenyl isothiocyanate was added and the reaction mixture was again stirred for 24 hours at room temperature. The solvent was then evaporated under reduced pressure and the residue was submitted to a flash chromatography (SiO2, CH2Cl2/MeOH 95/5). 428 mg of the desired product (formula shown hereinabove) were isolated as a red powder (yield=93%) which was characterized as follows:

ESIMS (+°): 511.2; 334.1; and

NMR $^1$H (CDCl$_3$+MeOD) ppm: 8.93 (H-7, s); 8.73 (H-4, dd, J=7.0 Hz, J=1.1 Hz); 8.40 (H-6, dd, J=8.8 Hz, J=1.1 Hz); 8.14 (H-8, dd, J=8.4 Hz, J=0.7 Hz); 8.07 (H-10, d, J=7.3 Hz, J=1.1 Hz); 7.77 (H-9, t, J=7.3 Hz); 7.75 (H-5, dd, J=6.9 and 8.1 Hz); 7.35 (2H-arom, d, J=8.8 Hz); 7.28 (2H-arom, d, J=8.4 Hz); 4.21 (CH$_2$—N, t, J=7.0 Hz); 2.93 (Me-CH-Me, m); 2.62 (CH$_2$—N, t, J=7.0 Hz) and 2.28 (N(CH$_3$)$_2$, s); 1.27 (CH$_3$—, s); and 1.25 (CH$_3$—, s).

EXAMPLE 34

Preparation of 1-{2-[2-(dimethylamino)ethyl]-1,3-dioxo-2,3-dihydro-1H-dibenzo[de,h]isoquinolin-11-yl}-3-[4-methoxyphenyl]thiourea 300 mg of 11-amino-2-[2-(dimethylamino)ethyl]-1H-dibenzo[de,h]isoquinoline-1,3(2H)-dione (obtained in example 3) (0.90 mmole) are dissolved in 20 ml of acetonitrile. 250 µl (2 molar equivalents) of 4-methoxyphenyl isothiocyanate was added and the reaction mixture was maintained at room temperature for 16 hours. Two more equivalents of 4-methoxyphenyl isothiocyanate was added and the reaction mixture was stirred for 24 hours at room temperature. The solvent was then evaporated under reduced pressure and the residue was submitted to a flash chromatography (SiO2, CH2Cl2/MeOH 95/5). 409 mg of UN the desired product (formula shown hereinabove) were isolated as a red powder (yield=91%) which was characterized as follows:

ESIMS (+): 499.1; 334.1; and

NMR $^1$H (CDCl$_3$+MeOD) ppm: 8.93 (H-7, s); 8.73 (H-4, dd, J=7.3 Hz, J=1.5 Hz); 8.39 (H-6, dd, J=8.3 Hz, J=1.1 Hz); 8.14 (2H-arom, d, J=8.1 Hz); 7.77 (H-9, t, J=4.4 Hz); 7.74 (H-5, dd, J=8.4 Hz, J=4.4 Hz); 7.36 (2H-arom, d, J=9.2 Hz); 6.99 (2H-arom, d, J=8.8 Hz); 4.15 (CH$_2$—N, t, J=7.0 Hz); 3.84 (CH$_3$—O—, s); 2.93 (Me-CH-Me, m); 2.60 (CH$_2$—N, t, J=7.0 Hz) and 2.30 (N(CH$_3$)$_2$, s).

EXAMPLE 35

Preparation of 1-{2-[2-(dimethylamino)ethyl]-1,3-dioxo-2,3-dihydro-1H-dibenzo[de,h]isoquinolin-11-yl}-3-[ethyl]thiourea

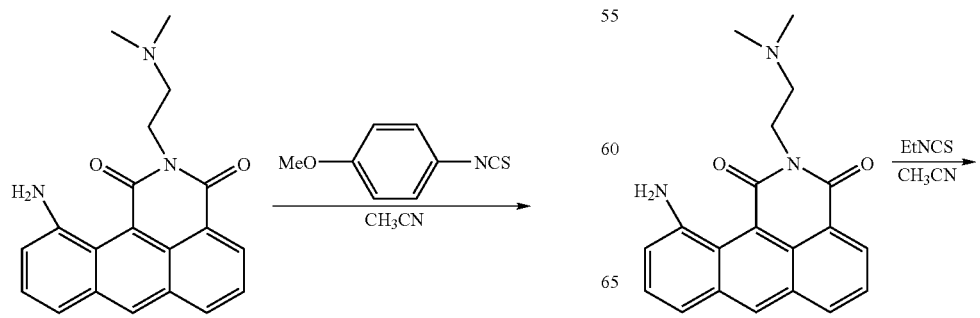

-continued

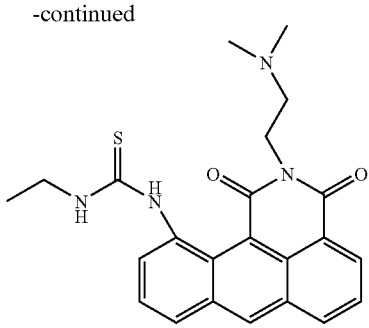

100 mg of 11-amino-2-[2-(dimethylamino)ethyl]-1H-dibenzo[de,h]isoquinoline-1,3(2H)-dione (obtained in example 3) (0.30 mmole) were dissolved in 6 ml of acetonitrile. 52 μl (2 molar equivalents) of ethyl isothiocyanate was added and the reaction mixture was maintained at room temperature for 16 hours. The solvent was then evaporated under reduced pressure and the residue was submitted to a flash chromatography (SiO2, CH2Cl2/MeOH 95/5). 92 mg of the desired product (formula shown hereinabove) were isolated as a red powder (yield=73%) which was characterized as follows:

ESIMS (+): 421.3; and

NMR $^1$H (DMSO) ppm: 9.40 (—NH—CS—NH, s); 9.26 (H-arom, s); 8.62 (2H-arom, td, J=7.0 Hz, J=1.1 Hz); 8.26 (H-arom, dd, J=7.7 Hz, J=1.5 Hz); 7.82 (3H-arom, m); 7.80 (—NH—CS—NH, s); 4.25 (CH$_2$—N, t, J=7.0 Hz); 2.66 (—CH$_2$—NH—, t, J=6.2 Hz); 2.28 (N(CH$_3$)$_2$, s), and 1.04 (CH$_3$—CH$_2$—, m).

EXAMPLE 36

Preparation of 1-{2-[2-(dimethylamino)ethyl]-1,3-dioxo-2,3-dihydro-1H-dibenzo[de,h]isoquinolin-11-yl}-3-[allyl]thiourea

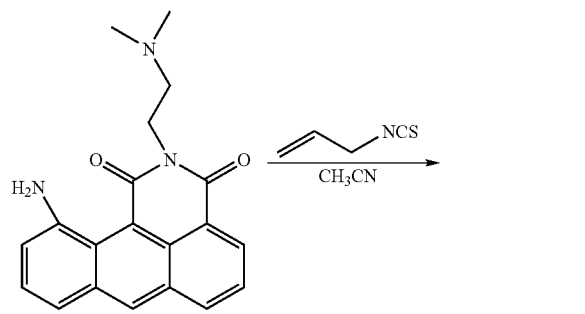

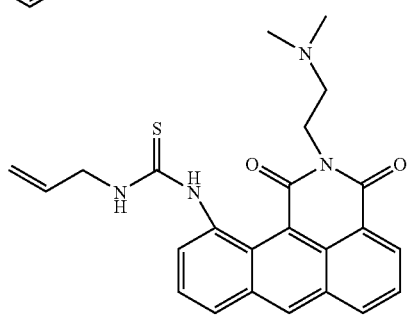

100 mg of 11-amino-2-[2-(dimethylamino)ethyl]-1H-dibenzo[de,h]isoquinoline-1,3(2H)-dione (obtained in example 3) (0.30 mmole) were dissolved in 6 ml of acetonitrile. 58 μl (2 molar equivalents) of allyl isothiocyanate was added and the reaction mixture was maintained at room temperature for 16 hours. The solvent was then evaporated under reduced pressure and the residue was submitted to a flash chromatography (SiO2, CH2Cl2/MeOH 95/5). 90 mg of the desired product (formula shown hereinabove) were isolated as a red powder (yield=69%) which was characterized as follows:

ESIMS (+): 433.3; and

NMR $^1$H (DMSO) ppm: 9.50 (—NH—CS—NH, s); 9.27 (H-arom, s); 8.63 (2H-arom, td, J=7.0 Hz, J=1.1 Hz); 8.28 (H-arom, dd, J=8.1 Hz, J=1.1 Hz); 8.03 (—NH—CS—NH, s); 7.83 (3H-arom, m); 5.82 (CH$_2$=CH—, m); 5.14 (CH$_2$=CH—, d, J=17.6 Hz); 5.05 (CH$_2$=CH—, d, J=9.9 Hz); 4.28 (—CH$_2$—N—, t, J=6.6 Hz); 4.05 (H-allylic, t, J=5.1 Hz); 2.75 (—CH$_2$—N—, t, J=5.9 Hz); and 2.34 (N(CH$_3$)$_2$, s).

EXAMPLE 37

Preparation of 1-{2-[2-(dimethylamino)ethyl]-1,3-dioxo-2,3-dihydro-1H-dibenzo[de,h]isoquinolin-11-yl}-3-[2-methoxyphenyl]thiourea

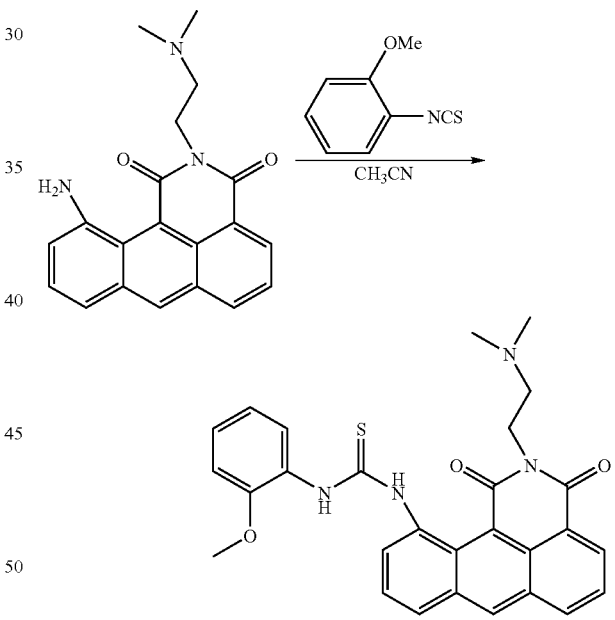

100 mg of 11-amino-2-[2-(dimethylamino)ethyl]-1H-dibenzo[de,h]isoquinoline-1,3(2H)-dione (obtained in example 3) (0.30 mmole) were dissolved in 8 ml of acetonitrile. 83 μl (2 molar equivalents) of 2-methoxyphenyl isothiocyanate was added and the reaction mixture was maintained at room temperature for 45 hours at 55° C. The solvent was then evaporated under reduced pressure and the residue was submitted to a flash chromatography (SiO2, CH2Cl2/MeOH 95/5). 142 mg of the desired product (formula shown hereinabove) were isolated as a red powder (yield=95%) which was characterized as follows:

ESIMS (+): 499.4;

NMR $^1$H (DMSO) ppm: 10.27 (—NHCS—NH—, bs); 10.06 (—NHCS—NH—, bs); 9.28 (H-arom, s); 8.62 (3H- arom, m); 8.34 (2H-arom, m); 8.03 (2H-arom, m); 7.86 (2H-arom, m); 7.35 (H-arom, td, J=8.4 Hz, J=1.5 Hz); 4.19 (—CH$_2$—N—, t, J=7.0 Hz); and 2.51 (2.13 (N(CH$_3$)$_2$, s); and NMR $^{13}$C (CDCl$_3$+MeOD) ppm: 179.5; 165.5; 163.5; 151.1; 137.4; 135.0; 134.2; 133.6; 133.4; 132.0; 129.7; 128.9; 128.4; 128.4; 126.4; 126.1; 126.1; 125.7; 124.1; 121.9; 120.4; 116.2; 56.2; 55.3; 44.8; and 38.1.

EXAMPLE 38

Preparation of 1-{2-[2-(dimethylamino)ethyl]-1,3-dioxo-2,3-dihydro-1H-dibenzo[de,h]isoquinolin-11-yl}-3-[3-pyridyl]thiourea

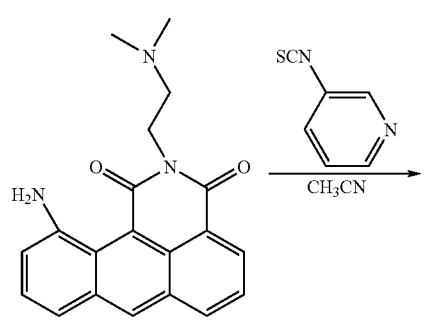

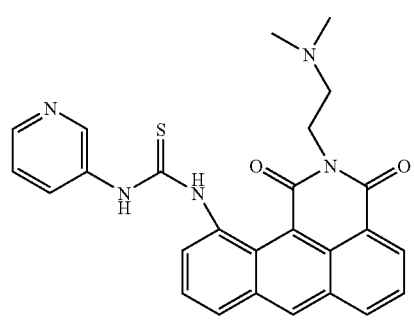

100 mg of 11-amino-2-[2-(dimethylamino)ethyl]-1H-dibenzo[de,h]isoquinoline-1,3(2H)-dione (obtained in example 3) (0.30 mmole) were dissolved in 8 ml of acetonitrile. 67 µl (2 molar equivalents) of 3-pyridyl isothiocyanate was added and the reaction mixture was maintained at room temperature for 16 hours. The solvent was then evaporated under reduced pressure and the residue was submitted to a flash chromatography (SiO2, CH2Cl2/MeOH 95/5). 132 mg of the desired product (formula shown hereinabove) were isolated as a red powder (yield=94%) which was characterized as follows:

ESIMS (+): 470.3, 334.3, and 235.9;
NMR $^1$H (DMSO) ppm: 10.01 (—NHCS—NH—, s); 9.41 (—NHCS—NH—, s); 9.28 (H-arom, s); 8.62 (2H-arom, td, J=7.0 Hz, J=1.5 Hz); 8.27 (H-arom, d, J=7.7 Hz); 7.86 (4H-arom, m); 7.16 (H-arom, td, J=8.4 Hz, J=1.5 Hz); 7.06 (H-arom, d, J=7.3 Hz); 6.91 (H-arom, td J=7.7 Hz, J=1.1 Hz); 4.11 (—CH$_2$—N—, t, J=7.0 Hz); 3.82 (CH$_3$—O—, s); 2.55 (—CH$_2$—N—, t, J=5.9 Hz); and 2.13 (6H, N(CH$_3$)$_2$, s); and NMR $^{13}$C (DMSO) ppm: 180.2; 164.1; 162.9; 145.4; 145.3, 145.0, 144.8, 137.0; 136.1; 135.1; 134.1; 133.5; 132.0; 130.6; 129.3; 128.0; 128.0; 127.6; 126.4; 125.9; 123.1; 123.0; 121.7; 116.6; 56.2; 48.5; and 45.1.

EXAMPLE 39

Preparation of 1-{2-[2-(dimethylamino)ethyl]-1,3-dioxo-2,3-dihydro-1H-dibenzo[de,h]isoquinolin-11-yl}-3-[2-trifluoromethoxy4-bromophenyl]thiourea

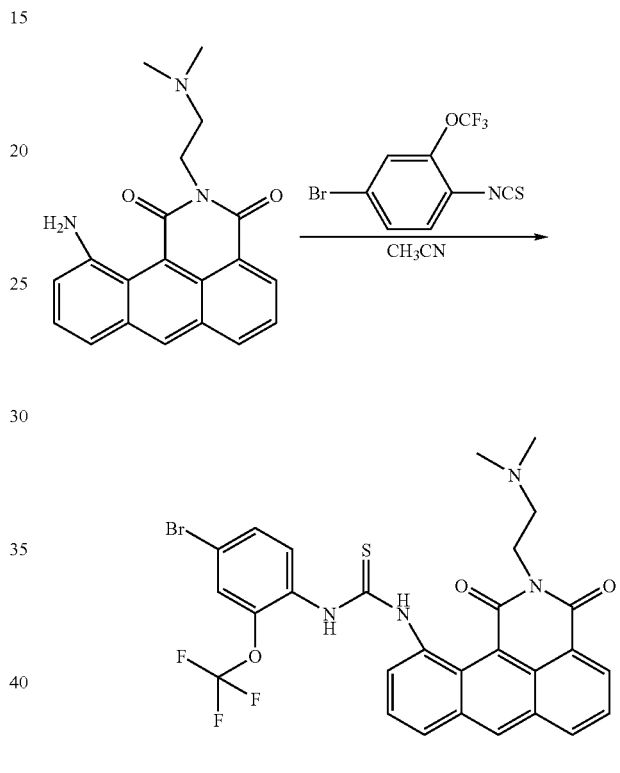

200 mg of 11-amino-2-[2-(dimethylamino)ethyl]-1H-dibenzo[de,h]isoquinoline-1,3(2H)-dione (obtained in example 3) (0.60 mmole) were dissolved in 15 ml of acetonitrile. 357 mg (2 molar equivalents) of 4-bromo-2-(trifluoromethoxy)phenyl isothiocyanate was added and the reaction mixture was maintained at room temperature for 16 hours. The solvent was then evaporated under reduced pressure and the residue was submitted to a flash chromatography (SiO2, CH2Cl2/MeOH 95/5). 356 mg of the desired product (formula shown hereinabove) were isolated as a red powder (yield=94%) which was characterized as follows:

ESIMS (+): 631.3, 633.3 (M+2); and
NMR $^1$H (DMSO) ppm: 10.2 (—NHCS—NH—, s); 9.91 (—NHCS—NH—, bs); 9.28 (H-arom, s); 8.63 (2H-arom, bt, J=7.0 Hz); 8.32 (H-arom, d, J=7.7 Hz) 7.8-8.0 (4H-arom, m); 7.62 (H-arom, s); 7.60 (H-arom, d, J=2.1 Hz); 4.18 (—CH$_2$—N—, t, J=7.0 Hz); 2.57 (—CH$_2$—N—, t, J=5.9 Hz); and 2.20 (6H, N(CH$_3$)$_2$, s).

EXAMPLE 40

Preparation of 1-{2-[2-(dimethylamino)ethyl]-1,3-dioxo-2,3-dihydro-1H-dibenzo[de,h]isoquinolin-11-yl}-3-[2-furylmethyl]thiourea

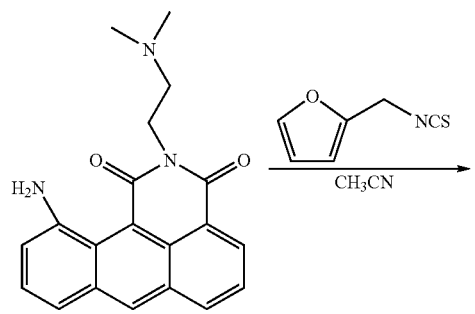

200 mg of 11-amino-2-[2-(dimethylamino)ethyl]-1H-dibenzo[de,h]isoquinoline-1,3(2H)-dione (obtained in example 3) (0.60 mmole) were dissolved in 15 ml of acetonitrile. 120 µl (2 molar equivalents) of 2-furylmethyl isothiocyanate was added and the reaction was maintained at room temperature overnight then for 5 hours at 55° C. The solvent was then evaporated under reduced pressure and the residue was submitted to a flash chromatography (SiO2, CH2Cl2/MeOH 95/5). 212 mg of the desired product (formula shown hereinabove) were isolated as a red powder (yield=75%) which was characterized as follows:

ESIMS (+): 470.3, 334.3, 235.9;

NMR $^1$H (DMSO) ppm: 9.58 (—NHCS—NH—, s); 9.22 (H-arom, s); 8.58 (2H-arom, td, J=7.0 Hz, J=1.5 Hz); 8.38 (H-arom, t, J=5.4 Hz); 8.24 (H-arom, d, J=8.1 Hz); 7.86-7.73 (3H-arom, m); 7.55 (1H-arom, s); 6.40 (H-furanyl, m); 6.27 (H-furanyl, bs); 4.64 (CH$_2$—NHCS—NH—, d, J=5.7 Hz); 4.22 (—CH$_2$—N—, t, J=7.0 Hz); 2.65 (—CH$_2$—N—, t, J=6.9 Hz); and 2.26 (6H, N(CH$_3$)$_2$, s); and NMR $^{13}$C (DMSO) ppm: 181.9; 164.6; 163.6; 152.3; 142.6; 137.3; 135.6; 134.8; 134.2; 133.9; 132.1; 129.6; 128.8; 128.7; 128.2; 127.2; 126.5; 122.4; 117.5; 111.0; 107.7; 56.9; and 45.9.

EXAMPLE 41

Preparation of 1-{2-[2-(dimethylamino)ethyl]-1,3-dioxo-2,3-dihydro-1H-dibenzo[de,h]isoquinolin-11-yl}-3-[4-trifluoromethylphenyl]thiourea

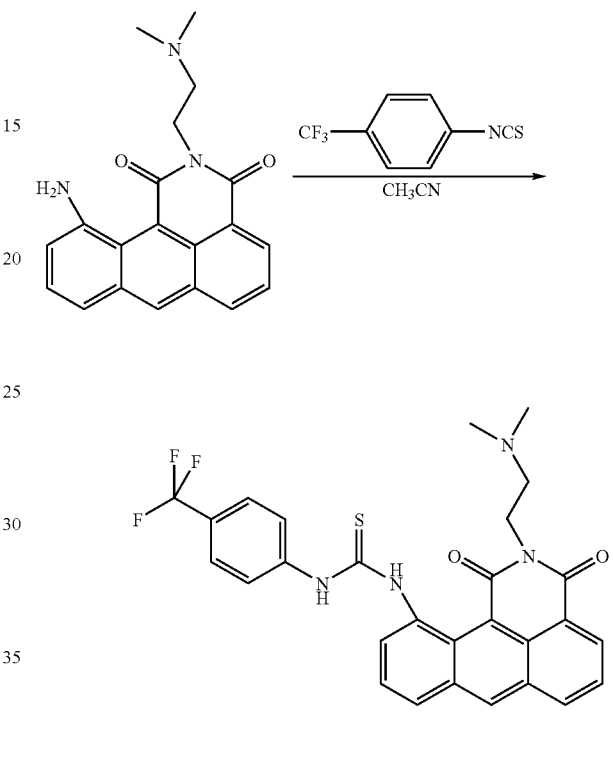

200 mg of 11-amino-2-[2-(dimethylamino)ethyl]-1H-dibenzo[de,h]isoquinoline-1,3(2H)-dione (obtained in example 3) (0.60 mmole) were dissolved in 10 ml of acetonitrile. 244 mg (2 molar equivalents) of 4-(trifluoromethyl)phenyl isothiocyanate was added and the reaction mixture was maintained at room temperature for 16 hours. The solvent was then evaporated under reduced pressure and the residue was submitted to a flash chromatography (SiO2, CH2Cl2/MeOH 95/5). 290 mg of the desired product (formula shown hereinabove) were isolated as a red powder (yield=90%) which was characterized as follows:

ESIMS (+): 537.3;

NMR $^1$H (DMSO) ppm: 10.55 (—NHCS—NH—, s); 10.1 (—NHCS—NH—, bs); 9.27 (H-arom, s); 8.62 (2H-arom, bt, J=7.0 Hz); 8.29 (H-arom, d, J=8.4 Hz); 7.8-8.0 (4H-arom, m); 7.66 (H-arom, d, J=8.7 Hz); 4.15 (—CH$_2$—N—, t, J=7.0 Hz); 2.51(—CH$_2$—N—, t, J=5.9 Hz); and 2.08 (6H, N(CH$_3$)$_2$, s); and NMR $^{13}$C (DMSO) ppm: 179.6; 164.1; 162.8; 143.2; 143.1; 137.1; 135.1; 134.1; 133.5; 133.4; 132.1; 129.5; 128.4; 127.6; 126.4; 125.9; 125.5; 124.0; 123.6; 122.3; 121.6; 116.6; 56.2; 45.0 (X2).

EXAMPLE 42

Preparation of 1-(1,3-benzodioxol-4-yl)-3-{2-[2-(dimethylamino)ethyl]-1,3-dioxo-2,3-dihydro-1H-dibenzo[de,h]isoquinolin-11-yl}thiourea

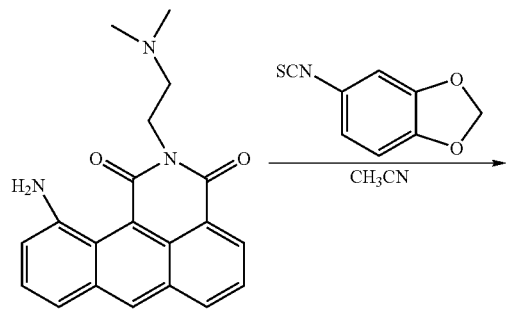

EXAMPLE 43

Preparation of 1-(2,1,3-Benzothiadiazol-5-yl)-3-{2-[2-(dimethylamino)ethyl]-1,3-dioxo-2,3-dihydro-1H-dibenzo[de,h]isoquinolin-11-yl}thiourea

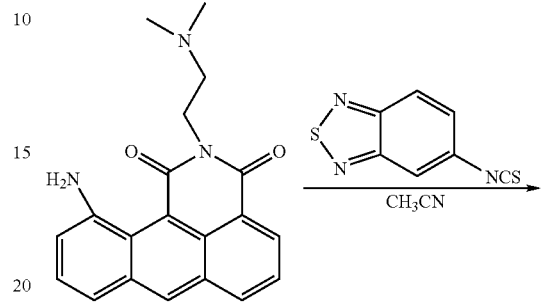

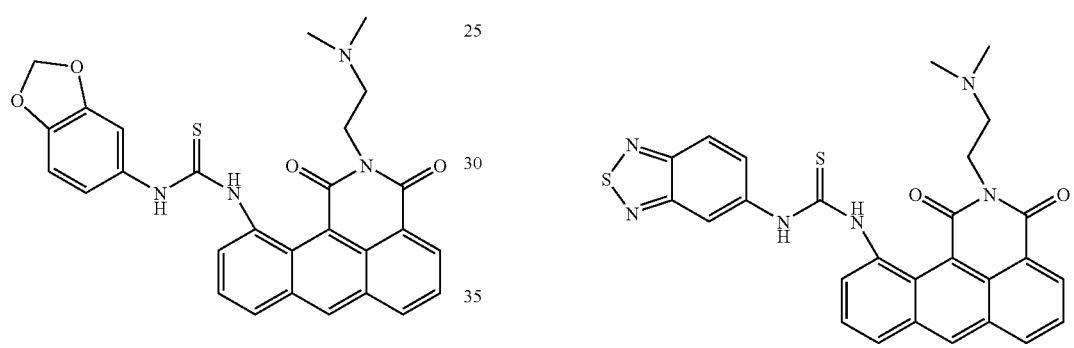

200 mg of 11-amino-2-[2-(dimethylamino)ethyl]-1H-dibenzo[de,h]isoquinoline-1,3(2H)-dione (obtained in example 3) (0.60 mmole) were dissolved in 10 ml of acetonitrile. 215 mg (2 molar equivalents) of 1,3-benzodioxol-5-yl isothyocyanate was added and the reaction mixture was maintained at room temperature for 16 hours. The solvent was then evaporated under reduced pressure and the residue was submitted to a flash chromatography (SiO2, CH2Cl2/MeOH 95/5). 246 mg of the desired product (formula shown hereinabove) were isolated as a red powder (yield=80%) which was characterized as follows:

ESIMS (+): 513.3, 334.3, and 257.3;

NMR $^1$H (DMSO) ppm: 9.98 (—NHCS—NH—, s); 9.81 (—NHCS—NH—, bs); 9.26 (H-arom, s); 8.61 (2H-arom, bt, J=7.5 Hz); 8.25 (H-arom, d, J=7.8 Hz); 7.98 (H-arom, d, J=7.0 Hz); 7.87-7.74 (2H-arom, m); 7.12 (1H-arom, s); 6.92 (H-arom, d, J=8.1 Hz); 6.84 (1H-arom, dd, J=7.8 Hz and 2 Hz); 6.02 (2H, —O—CH$_2$—O—, s); 4.10 (—CH$_2$—N—, t, J=7.0 Hz); 2.50 (—CH$_2$—N—, t, J=5.9 Hz); and 2.17 (6H, N(CH$_3$)$_2$, s); and NMR $^{13}$C (DMSO) ppm: 179.9; 164.5; 162.8; 147.0; 144.6; 137.3; 135.1, 134.5, 133.6; 133.3; 132.2; 129.5; 128.4; 127.9; 127.6; 126.3; 125.9, 121.6, 117.6, 116.2, 107.9, 106.2, 101.2, 56.2; 54.8, and 45.2.

215 mg of 11-amino-2-[2-(dimethylamino)ethyl]-1H-dibenzo[de,h]isoquinoline-1,3(2H)-dione (obtained in example 3) (0.645 mmole) were dissolved in 10 ml of acetonitrile. 250 mg (2 molar equivalents) of 2,1,3-benzothiadiazol-5-yl isothiocyanate was added and the reaction mixture was maintained at room temperature for 16 hours. The solvent was then evaporated under reduced pressure and the residue was submitted to a flash chromatography (SiO2, CH2Cl2/MeOH 95/5). 303 mg of the desired product (formula shown hereinabove) were isolated as a red powder (yield=89%) which was characterized as follows:

ESIMS (+): 527.4, 334.3, and 264.3;

NMR $^1$H (DMSO) ppm: 10.63 (—NHCS—NH—, s); 10.26 (—NHCS—NH—, bs); 9.26 (H-arom, s); 8.60 (2H-arom, bt, J=7.5 Hz); 8.44 (1H-arom, bs); 8.29 (H-arom, d, J=7.8 Hz); 7.98-8.03 (2H-arom, m); 7.88-7.77 (3H-arom, m); 4.15 (—CH$_2$—N—, t, J=7.0 Hz); 2.52 (—CH$_2$—N—, t, J=5.9 Hz); and 2.04 (6H, N(CH$_3$)$_2$, s); and NMR $^{13}$C (DMSO) ppm: 180.3; 164.7; 163.5, 155.2, 152.2; 141.6, 137.8, 137.7, 135.7; 135.7; 134.7; 134.2; 134.0; 130.1; 128.9; 128.7; 127.1, 127.0, 126.6, 126.2, 122.3, 121.1, 117.3, 110.9, 56.8; 55.4, 45.6.

EXAMPLE 44

Preparation of 1-(1,3-benzodioxol-4-ylmethyl)-3-{2-[2-(dimethylamino)ethyl]-1,3-dioxo-2,3-dihydro-1H-dibenzo[de,h]isoquinolin-11-yl}thiourea

EXAMPLE 45

Preparation of 1-{2-[2-(dimethylamino)ethyl]-1,3-dioxo-2,3-dihydro-1H-dibenzo[de,h]isoquinolin-11-yl}-3-[2-(trifluoromethoxy)phenyl]thiourea

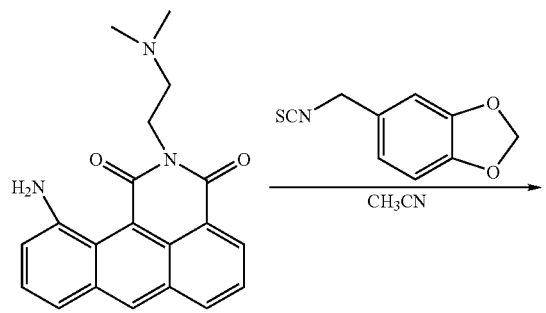

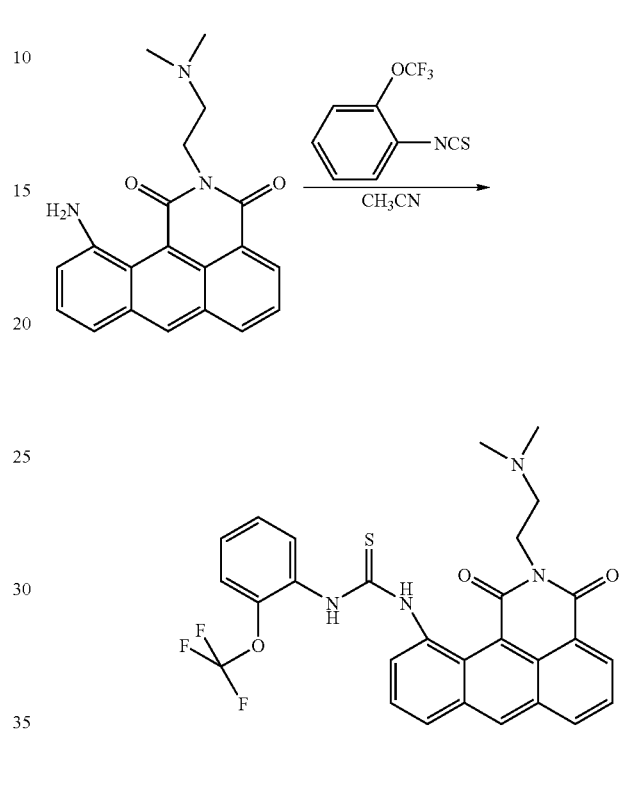

300 mg of 11-amino-2-[2-(dimethylamino)ethyl]-1H-dibenzo[de,h]isoquinoline-1,3(2H)-dione (obtained in example 3) (0.90 mmole) were dissolved in 10 ml of acetonitrile. 348 mg (2 molar equivalents) of 1,3-benzodioxol-5-ylmethyl isothiocyanate was added and the reaction mixture was maintained at room temperature for 48 hours. The solvent was then evaporated under reduced pressure and the residue was submitted to a flash chromatography (SiO2, CH2Cl2/MeOH 95/5). 392 mg of the desired product (formula shown hereinabove) were isolated as a red powder (yield=83%) which was characterized as follows:

ESIMS (+): 527.4;

NMR $^1$H (DMSO) ppm: 9.51 (—NHCS—NH—, bs); 9.23 (H-arom, s); 8.59 (2H-arom, dd, J=9.0 Hz and 7.2 Hz); 8.26 (2H-arom, d, J=7.8 Hz); 7.73-7.87 (3H-arom, m); 6.77 (2H-arom, m); 5.96 (2H, —O—CH$_2$—O—, s); 4.57 (—NHCS—NH—, d, J=8 Hz); 4.19 (—CH$_2$—N—, t, J=7.0 Hz); 2.66 (—CH$_2$—N—, t, J=5.9 Hz); and 2.27 (6H, N(CH$_3$)$_2$, s); and NMR $^{13}$C (DMSO) ppm: 163.9, 162.9, 146.9, 145.9; 136.6, 134.9, 134.0, 133.6; 133.3; 132.8; 131.4; 128.9; 128.2; 128.1; 127.6; 126.2, 121.7, 120.3, 116.8, 107.8, 107.7, 100.6, 56.2; 54.8; 47.1, and 45.1.

250 mg of 11-amino-2-[2-(dimethylamino)ethyl]-1H-dibenzo[de,h]isoquinoline-1,3(2H)-dione (obtained in example 3) (0.75 mmole) were dissolved in 10 ml of acetonitrile. 240 μL (2 molar equivalents) of 2-(trifluoromethoxy) phenyl isothiocyanate was added and the reaction mixture was maintained at room temperature for 20 hours. The solvent was then evaporated under reduced pressure and the residue was submitted to a flash chromatography (SiO2, CH2Cl2/MeOH 95/5). 368 mg of the desired product (formula shown hereinabove) were isolated as a red powder (yield=89%) which was characterized as follows:

ESIMS (+): 553.45;

NMR $^1$H (DMSO) ppm; 10.09 (—NHCS—NH—, s); 9.87 (—NHCS—NH—, s) 9.28 (H-arom, s); 8.63 (2H-arom, d, J=7.3 Hz); 8.29 (H-arom, d, J=8.4 Hz); 7.97 (H-arom, d, J=7.0 Hz); 7.89 (H-arom, t, J=8.1 Hz); 7.82 (2H-arom, td, J=7.0 Hz, J=2.2 Hz); 7.34-7.45 (3H-arom, m); 4.14 (—CH$_2$—N—, t, J=6.6 Hz); 2.52 (—CH$_2$—N—, t); and 2.15 (6H, N(CH$_3$)$_2$, s); and NMR $^{13}$C (DMSO) ppm: 180.85; 164.22; 162.84; 142.26; 137.16; 135.17; 134.24; 133.62; 133.39; 132.04; 131.47; 129.25; 128.76; 128.22; 128.07; 127.72; 127.15; 126.95; 126.41; 125.97; 121.69; 121.61; 121.05; 118.28; 116.29; 56.22; 54.81; and 45.14.

EXAMPLES 46 to 49

Preparation of 1-{2-[2-(dimethylamino)ethyl]-1,3-dioxo-2,3-dihydro-1H-dibenzo[de,h]isoquinolin-8-yl}-3-[substituted]thiourea The same procedure as in example 14 is repeated except that 3,4-(methylenedioxy)phenyl isocyanate is replaced with one of the following isothiocyanates:
4-(trifluoromethoxy)phenyl isothiocyanate
5-(isothiocyanatomethyl)-1,3-benzodioxole
4-chlorophenyl isothiocyanate, and
4-cyanophenyl isothiocyanate.

The following compounds are obtained in good yield:
1-{2-[2-(dimethylamino)ethyl]-1,3-dioxo-2,3-dihydro-1H-dibenzo[de,h]isoquinolin-8-yl}-3-[4-(trifluoromethoxy)phenyl]thiourea (example 27);
1-(1,3-benzodioxol-4-ylmethyl)-3-{2-[2-(dimethylamino)ethyl]-1,3-dioxo-2,3-dihydro-1H-dibenzo[de,h]isoquinolin-8-yl}thiourea (example 28);
1-(4-chlorophenyl)-3-{2-[2-(dimethylamino)ethyl]-1,3-dioxo-2,3-dihydro-1H-dibenzo[de,h]isoquinolin-8-yl}thiourea (example 29); and
1-(4-cyanophenyl)-3-{2-[2-(dimethylamino)ethyl]-1,3-dioxo-2,3-dihydro-1H-dibenzo[de,h]isoquinolin-8-yl}thiourea (example 30).

EXAMPLES 50 and 51

Preparation of 2-[2-(dimethylamino)ethyl]-N-8-{(N'-substituted-acetamide)}-3H-dibenzo[deh]isoquinoline-1,3(2H)-diones The same procedure as in example 16 is repeated except that benzoyl isocyanate is replaced with one of the following isocyanates:
2-chloroacetyl isocyanate, and
trichloroacetyl isocyanate.

The following compounds are obtained in good yield:
2-chloro-N-({2-[2-(dimethylamino)ethyl]-1,3-dioxo-2,3-dihydro-1H-dibenzo[de,h]isoquinolin-8-yl}carbamoyl)acetamide (example 31); and
2,2,2-trichloro-N-({2-[2-(dimethylamino)ethyl]-1,3-dioxo-2,3-dihydro-1H-dibenzo[de,h]isoquinolin-8-yl}carbamoyl)acetamide (example 32).

EXAMPLE 52

Preparation of ethyl ({2-[2-(dimethylamino)ethyl]-1,3-dioxo-2,3-dihydro-1H-dibenzo[de,h]isoquinolin-8-yl}carbamoyl)carbamate The same procedure as in example 16 is repeated except that benzoyl isocyanate is replaced with ethoxycarbonyl isocyanate, thus resulting in good yield into ethyl ({2-[2-(dimethylamino)ethyl]-1,3-dioxo-2,3-dihydro-1H-dibenzo[de,h]isoquinolin-8-yl}carbamoyl)carbamate.

EXAMPLE 53

Preparation of 1-(2-chloroethyl)-3-{2-[2-(dimethylamino)ethyl]-1,3-dioxo-2,3-dihydro-1H-dibenzo[de,h]isoquinolin-11-yl}urea The same procedure as in example 13 is repeated except that pentyl isocyanate is replaced with 2-chloroethylisocyanate, thus resulting in good yield into 1-(2-chloroethyl)-3-{2-[2-(dimethylamino)ethyl]-1,3-dioxo-2,3-dihydro-1H-dibenzo[de,h]isoquinolin-11-yl}urea.

EXAMPLES 54 to 58

Preparation of 2-[2-(dimethylamino)ethyl]-N-11-{(N'-substituted-thiourea)}-3H-dibenzo[deh]isoquinoline-1,3(2H)-diones The same procedure as in example 12 is repeated except that 3,4-(methylenedioxy)phenyl isocyanate is replaced with one of the following isothiocyanates:
4-chlorophenyl isothiocyanate,
4-cyanophenyl isothiocyanate,
ethyl-4-thiocyanatobenzoate,
4-(trifluoromethoxy)phenyl isothiocyanate, and
4-methoxyphenylisothiocyanate.

The following compounds are obtained in good yield:
1-(4-chlorophenyl)-3-{2-[2-(dimethylamino)ethyl]-1,3-dioxo-2,3-dihydro-1H-dibenzo[de,h]isoquinolin-11-yl}thiourea (example 35),
1-(4-cyanophenyl)-3-{2-[2-(dimethylamino)ethyl]-1,3-dioxo-2,3-dihydro-1H-dibenzo[de,h]isoquinolin-11-yl}thiourea (example 36),
ethyl 4-{[({2-[2-(dimethylamino)ethyl]-1,3-dioxo-2,3-dihydro-1H-dibenzo[de,h]isoquinolin-11-yl}amino)carbonothioyl]amino}benzoate (example 37),
1-{2-[2-(dimethylamino)ethyl]-1,3-dioxo-2,3-dihydro-1H-dibenzo[de,h]isoquinolin-11-yl}-3-[4-(trifluoromethoxy)phenyl]thiourea (example 38), and
1-{2-[2-(dimethylamino)ethyl]-1,3-dioxo-2,3-dihydro-1H-dibenzo[de,h]isoquinolin-11-yl}-3-(4-methoxyphenyl)thiourea (example 39).

EXAMPLES 59 to 72

Preparation of 2-[2-(dimethylamino)ethyl]-N-11-{(N'-substituted-amide)}-3H-dibenzo[deh]isoquinoline-1,3(2H)-diones The same procedure as in example 9 is repeated except that methyl chloroformate is replaced with one of the following monocarboxylic acid chlorides:
ethyl 4-chloro-4-oxobutanoate
ethyl 3-chloro-3-oxopropanoate
4-methoxyphenylacetyl chloride,
trichloroacetyl chloride,
trifluoroacetyl chloride,
benzoyl chloride,
1-naphthoyl chloride,
2-naphthoyl chloride,
4-propylbenzoyl chloride,
4-pentylbenzoyl chloride,
caproyl chloride,
hydrocinnamoyl chloride,
capryloyl chloride, and
n-butyryl chloride.

The following compounds are thus obtained in good yield:
ethyl 4-({2-[2-(dimethylamino)ethyl]-1,3-dioxo-2,3-dihydro-1H-dibenzo[de,h]isoquinolin-11-yl}amino)-4-oxobutanoate (example 40),
ethyl 4-({2-[2-(dimethylamino)ethyl]-1,3-dioxo-2,3-dihydro-1H-dibenzo[de,h]isoquinolin-11-yl}amino)-4-oxopropanoate (example 41), 2-(4-chlorophenyl)-N-{2-[2-(dimethylamino)ethyl]-1,3-dioxo-2,3-dihydro-1H-dibenzo[de,h]isoquinolin-11-yl}acetamide (example 42), 2,2,2-trichloro-N-{2-[2-(dimethylamino)ethyl]-1,3-dioxo-2,3-dihydro-1H-dibenzo[de,h]isoquinolin-11-yl}acetamide (example 43), N-{2-[2-(dimethylamino)ethyl]-1,3-dioxo-2,3-dihydro-1H-dibenzo[de,h]isoquinolin-11-yl}-2,2,2-trifluoroacetamide (example 44), N-{2-[2-(dimethylamino)ethyl]-1,3-dioxo-2,3-dihydro-1H-dibenzo[de,h]isoquinolin-11-yl}benzamide (example 45), N-{2-[2-(dimethylamino)ethyl]-1,3-dioxo-2,3-dihydro-1H-dibenzo[de,h]isoquinolin-11-yl}-1-naphthamide (example 46), N-{2-[2-(dimethylamino)ethyl]-1,3-dioxo-2,3-dihydro-1H-dibenzo[de,h]isoquinolin-11-yl}-2-naphthamide (example 47), N-{2-[2-(dimethylamino)ethyl]-1,3-dioxo-2,3-dihydro-1H-dibenzo[de,h]isoquinolin-11-yl}-4-propylbenzamide (example 48), N-{2-[2-(dimethylamino)ethyl]-1,3-dioxo-2,3-dihydro-1H-dibenzo[de,h]isoquinolin-11-yl}-4-pentylbenzamide (example 49), N-{2-[2-(dimethylamino)ethyl]-1,3-dioxo-2,3-dihydro-1H-dibenzo[de,h]isoquinolin-11-yl}hexanamide (example 50), N-{2-[2-(dimethylamino)ethyl]-1,3-dioxo-2,3-dihydro-1H-dibenzo[de,h]isoquinolin-11-yl}-3-phenylpropanamide (example 51), N-{2-[2-(dimethylamino)ethyl]-1,3-dioxo-2,3-dihydro-1H-dibenzo[de,h]isoquinolin-11-yl}octanamide (example 52), and N-{2-[2-(dimethylamino)ethyl]-1,3-dioxo-2,3-dihydro-1H-dibenzo[de,h]isoquinolin-11-yl}butanamide (example 53).

EXAMPLES 73 to 77

Preparation of 2-[2-(dimethylamino)ethyl]-N-8-(N'-substituted-methyleneamino)-3H-dibenzo[deh]isoquinoline-1,3(2H)-diones The same procedure as in example 6 is repeated except that 2,5-dihydroxy-benzaldehyde is replaced with one of the following aldehydes:

vanillin,
3,4,5-trimethoxybenzaldehyde,
4-cyanobenzaldehyde,
6-nitropiperonal, and
propionaldehyde.

The following compounds are thus obtained in good yield:

2-[2-(dimethylamino)ethyl]-8-{[(1Z)-(4-hydroxy-3-methoxyphenyl)-methylene]amino}-1H-dibenzo[deh]isoquinoline-1,3(2H)-dione (example 54), 2-[2-(dimethylamino)ethyl]-8-{[(1Z)-(3,4,5-trimethoxyphenyl)methylene]-amino}-1H-dibenzo[deh]isoquinoline-1,3(2H)-dione (example 55), 4-[(Z)-({2-[2-(dimethylamino)ethyl]-1,3-dioxo-2,3-dihydro-1H-dibenzo[de,h]-isoquinolin-8-yl}imino)methyl]benzonitrile (example 56), 2-[2-(dimethylamino)ethyl]-11-{[(1Z)-(6-nitro-1,3-benzodioxol-5-yl)methylene]amino}-1H-dibenzo[de,h]isoquinoline-1,3(2H)-dione (example 57), and 2-[2-(dimethylamino)ethyl]-8-[(1E)-propylideneamino]-1H-dibenzo[de,h]isoquinoline-1,3(2H)-dione (example 58).

EXAMPLE 78

Preparation of methyl {2-[2-(dimethylamino)ethyl]-1,3-dioxo-2,3-dihydro-1H-dibenzo[de,h]isoquinolin-8-yl}carbamate The same procedure as in example 9 is repeated except that the azonafide derivative of example 3 is replaced by the azonafide derivative of example 4. methyl {2-[2-(dimethylamino)ethyl]-1,3-dioxo-2,3-dihydro-1H-dibenzo[de,h]isoquinolin-8-yl}carbamate is thus obtained in good yield.

EXAMPLE 79

Preparation of 4-chloro-N-{2-[2-(dimethylamino)ethyl]-1,3-dioxo-2,3-dihydro-1H-dibenzo[de,h]isoquinolin-8-yl}butanamide The same procedure as in example 10 is repeated except that the azonafide derivative of example 3 is replaced by the azonafide derivative of example 4. The desired product, 4-chloro-N-{2-[2-(dimethylamino)ethyl]-1,3-dioxo-2,3-dihydro-1H-dibenzo[de,h]isoquinolin-8-yl}butanamide, is thus obtained in good yield.

EXAMPLE 80

Preparation of 2-(4-chlorophenyl)-N-{2-[2-(dimethylamino)ethyl]-1,3-dioxo-2,3-dihydro-1H-dibenzo[de,h]isoquinolin-8-yl}acetamide The same procedure as in example 11 is repeated except that the azonafide derivative of example 3 is replaced by the azonafide derivative of example 4. 2-(4-chlorophenyl)-N-{2-[2-(dimethylamino)ethyl]-1,3-dioxo-2,3-dihydro-1H-dibenzo[de,h]isoquinolin-8-yl}acetamide is thus obtained in good yield.

EXAMPLE 81

Preparation of 1-{2-[2-(dimethylamino)ethyl]-1,3-dioxo-2,3-dihydro-1H-dibenzo[de,h]isoquinolin-8-yl}-3-pentylurea The same procedure as in example 13 is repeated except that the azonafide derivative of example 3 is replaced by the azonafide derivative of example 4. The desired product, 1-{2-[2-(dimethylamino)ethyl]-1,3-dioxo-2,3-dihydro-1H-dibenzo[de,h]isoquinolin-8-yl}-3-pentylurea, is thus obtained in good yield.

EXAMPLE 82

Preparation of N-({2-[2-(dimethylamino)ethyl]-1,3-dioxo-2,3-dihydro-1H-dibenzo[de,h]isoquinolin-11-yl}carbamoyl)benzamide The same procedure as in example 16 is repeated except that the azonafide derivative of example 4 is replaced by the azonafide derivative of example 3. The desired product, N-({2-[2-(dimethylamino)ethyl]-1,3-dioxo-2,3-dihydro-1H-dibenzo[de,h]isoquinolin-11-yl}carbamoyl)benzamide, is thus obtained in moderate yield.

EXAMPLE 83

Preparation of ethyl {2-[2-(dimethylamino)ethyl]-1, 3-dioxo-2,3-dihydro-1H-dibenzo[de,h]isoquinolin-8-yl}carbamate The same procedure as in example 17 is repeated except that the azonafide derivative of example 3 is replaced by the azonafide derivative of example 4. ethyl {2-[2-(dimethylamino)ethyl]-1,3-dioxo-2,3-dihydro-1H-dibenzo[de,h]isoquinolin-8-yl}carbamate is thus obtained in good yield.

EXAMPLE 84

Preparation of phenyl {2-[2-(dimethylamino)ethyl]-1,3-dioxo-2,3-dihydro-1H-dibenzo[de,h]isoquinolin-8-yl}carbamate The same procedure as in example 18 is repeated except that the azonafide derivative of example 3 is replaced by the azonafide derivative of example 4. phenyl {2-[2-(dimethylamino)ethyl]-1,3-dioxo-2,3-dihydro-1H-dibenzo[de,h]isoquinolin-8-yl}carbamate is thus obtained in good yield.

EXAMPLE 85

Preparation of N-{2-[2-(dimethylamino)ethyl]-1,3-dioxo-2,3-dihydro-1H-dibenzo[de,h]isoquinolin-8-yl}-3-oxododecanamide The same procedure as in example 20 is repeated except that the azonafide derivative of example 3 is replaced by the azonafide derivative of example 4. N-{2-[2-(dimethylamino)ethyl]-1,3-dioxo-2,3-dihydro-1H-dibenzo[de,h]isoquinolin-8-yl}-3-oxododecanamide is thus obtained in good yield.

EXAMPLE 86

Preparation of N-{2-[2-(dimethylamino)ethyl]-1,3-dioxo-2,3-dihydro-1H-dibenzo[de,h]isoquinolin-8-yl}-3-oxo-5-phenylpentanamide The same procedure as in example 22 is repeated except that the azonafide derivative of example 3 is replaced by the azonafide derivative of example 4. N-{2-[2-(dimethylamino)ethyl]-1,3-dioxo-2,3-dihydro-1H-dibenzo[de,h]isoquinolin-8-yl}-3-oxo-5-phenylpentanamide is thus obtained in good yield.

EXAMPLE 87

Preparation of ethyl 6-({2-[2-(dimethylamino)ethyl]-1,3-dioxo-2,3-dihydro-1H-dibenzo[de,h]isoquinolin-8-yl}amino)-4,6-dioxohexanoate The same procedure as in example 23 is repeated except that the azonafide derivative of example 3 is replaced by the azonafide derivative of example 4. ethyl 6-({2-[2-(dimethylamino)ethyl]-1,3-dioxo-2,3-dihydro-1H-dibenzo[de,h]isoquinolin-8-yl}amino)-4,6-dioxohexanoate is thus obtained in good yield.

EXAMPLE 88

Preparation of 4-fluorophenyl {2-[2-(dimethylamino)ethyl]-1,3-dioxo-2,3-dihydro-1H-dibenzo[de,h]isoquinolin-8-yl}carbamate The same procedure as in example 24 is repeated except that the azonafide derivative of example 3 is replaced by the azonafide derivative of example 4. The desired product, 4-fluorophenyl-{2-[2-(dimethylamino)ethyl]-1,3-dioxo-2,3-dihydro-1H-dibenzo[de,h]isoquinolin-8-yl}carbamate is thus obtained in good yield.

EXAMPLE 89

Preparation of octyl {2-[2-(dimethylamino)ethyl]-1, 3-dioxo-2,3-dihydro-1H-dibenzo[de,h]isoquinolin-8-yl}carbamate The same procedure as in example 25 is repeated except that the azonafide derivative of example 3 is replaced by the azonafide derivative of example 4. The desired product, octyl-{2-[2-(dimethylamino)ethyl]-1,3-dioxo-2,3-dihydro-1H-dibenzo[de,h]isoquinolin-8-yl}carbamate is thus obtained in good yield.

EXAMPLE 90

Preparation of allyl {2-[2-(dimethylamino)ethyl]-1, 3-dioxo-2,3-dihydro-1H-dibenzo[de,h]isoquinolin-8-yl}carbamate The same procedure as in example 26 is repeated except that the azonafide derivative of example 3 is replaced by the azonafide derivative of example 4. Allyl{2-[2-(dimethylamino)ethyl]-1,3-dioxo-2,3-dihydro-1H-dibenzo[de,h]isoquinolin-8-yl}carbamate is thus obtained in good yield.

EXAMPLE 91

Effect of Azonafide Derivatives on Overall Cell Growth

MTT tests were performed in order to rapidly, i.e. within 5 days, measure the effect of azonafide derivatives of this invention on the overall cell growth. The test measures the number of metabolically active living cells that are able to transform the yellow product 3-(4,5-dimethylthiazol-2-yl)-2,5-diphenyl tetrazolium bromide (herein referred as MTT) into the blue product formazan dye by mitochondrial reduction. The amount of formazan obtained at the end of the experiment, measured by means of a spectrophotometer, is directly proportional to the number of living cells. Optical density determination thus enables a quantitative measurement of the effect of the investigated compounds as compared to the control condition (untreated cells) and/or to other reference compounds.

Height human cancer cell lines described in table 1 were used in the following MTT tests. These cell lines cover six histological cancer types, being prostate, glioma, pancreas, colon, lung and breast cancers. Cells were allowed to grow in 96-well micro-wells with a flat bottom with an amount of 100 µl of cell suspension per well with 1,000 to 4,000 cells/well depending on the cell type used. Each cell line was seeded in a well known MEM 5% serum culture medium.

TABLE 1

| Cell line | ATCC code | tissue | literature reference |
|---|---|---|---|
| PC3 | CRL-1435 | Prostate | Invest. Urol. 17: 16-23, 1979; Cancer Res. 40: 524-534, 1980 |
| Hs683 | HTB-138 | Glioma | J. Natl. Cancer Inst. 56: 843-849, 1976; ibid. 58: 1455-1463, 1977 |
| U-373MG | HTB-17 | Glioma | Acta Pathol. Microbial. Scand. 74: 465-486, 1968 |
| BxPC3 | CRL-1687 | Pancreas | Cancer Invest. 4: 15-23, 1986; Clin. Lap. Med. 2: 567-578, 1982 |
| HCT-15 | CCL-225 | Colon | Cancer Res. 39: 1020-1025, 1979 |
| LoVo | CCL-229 | Colon | Exp. Cell Res. 101: 414-416, 1976; J. Natl. Cancer Inst. 61: 75-83, 1978; Cancer Res. 39: 2630-2636, 1979 |
| A549 | CCL-185 | Lung | J. Natl. Cancer Inst. 51: 1417-1423, 1973; Int. J. Cancer 17: 62-70, 1976 |
| MCF-7 | HTB-22 | Breast | J. Natl. Cancer Inst. 51: 1409-1416, 1973 |

The detailed experimental procedure was as following: after a 24-hour period of incubation at 37° C., the culture medium was replaced by 100 µl of fresh medium in which the compound to be tested was dissolved at the following molar concentrations: $10^{-9}$ M, $5.10^{-9}$ M, $10^{-8}$ M, $5.10^{-8}$ M, $10^{-7}$ M, $5.10^{-7}$ M, $10^{-6}$ M, $5.10^{-6}$ M and $10^{-5}$ M. Each experiment was repeated 6 times.

After 72 hours of incubation at 37° C. with (experimental conditions) or without (control condition) the compound to be tested, the medium was replaced by 100 µl MTT dissolved in RPMI at a concentration of 1 mg/ml. The micro-wells were subsequently incubated during 3 hours at 37° C. and centrifuged at 400 g during 10 minutes. MTT was removed and formazan crystals formed were dissolved in 100 µl DMSO. The micro-wells were shaken for 5 minutes and read on a spectrophotometer at wavelengths of 570 nm (maximum formazan absorbance) and 630 nm (back-ground noise).

For each experimental condition, the mean optical density was calculated, as well as the percentage of remaining living cells in comparison with the control.

Table 2 below shows the $IC_{50}$ values obtained for the human cancer cell lines (mean of six cell lines) for various azonafide derivatives of this invention. $IC_{50}$ represents the range of molar concentrations of the compound tested that resulted in a 50% inhibition of overall tumor cells growth. $IC_{50}$ values for compounds of examples 3 to 26 were obtained on cell lines Hs683, U-373MG, HCT-15, LoVo, A549 and MCF-7 described in Table 1. $IC_{50}$ values for compounds from examples 27 to 45 were obtained on cell lines PC3, U-373MG, BxPC3, LoVo, A549 and MCF-7 described in Table 1.

TABLE 2

| Compound of example | $IC_{50}$ (M) |
|---|---|
| 3 | $10^{-5}$-$5 \cdot 10^{-6}$ |
| 4 | $5 \cdot 10^{-6}$-$10^{-6}$ |
| 5 | $>10^{-5}$ |
| 6 | $5 \cdot 10^{-6}$-$10^{-6}$ |
| 7 | $>10^{-5}$ |
| 8 | $5 \cdot 10^{-6}$-$10^{-6}$ |
| 9 | $10^{-5}$-$5 \cdot 10^{-6}$ |
| 10 | $5 \cdot 10^{-6}$-$10^{-6}$ |
| 11 | $>10^{-5}$ |
| 12 | $10^{-5}$-$5 \cdot 10^{-6}$ |
| 13 | $10^{-5}$-$5 \cdot 10^{-6}$ |
| 14 | $>10^{-5}$ |
| 15 | $>10^{-5}$ |
| 16 | $5 \cdot 10^{-6}$-$10^{-6}$ |
| 17 | $>10^{-5}$ |
| 18 | $>10^{-5}$ |
| 20 | $>10^{-5}$ |
| 22 | $>10^{-5}$ |
| 23 | $>10^{-5}$ |
| 24 | $>10^{-5}$ |
| 25 | $10^{-5}$-$5 \cdot 10^{-6}$ |
| 27 | $>10^{-5}$ |
| 28 | $>10^{-5}$ |
| 29 | $>10^{-5}$ |
| 30 | $>10^{-5}$ |
| 31 | $>10^{-5}$ |
| 32 | $10^{-5}$-$5 \cdot 10^{-6}$ |
| 33 | $>10^{-5}$ |
| 34 | $>10^{-5}$ |
| 35 | $>10^{-5}$ |
| 36 | $>10^{-5}$ |
| 37 | $>10^{-5}$ |
| 38 | $>10^{-5}$ |
| 39 | $>10^{-5}$ |
| 40 | $5 \cdot 10^{-6}$-$10^{-6}$ |
| 41 | $5 \cdot 10^{-6}$-$10^{-6}$ |
| 42 | $>10^{-5}$ |
| 43 | $5 \cdot 10^{-6}$-$10^{-6}$ |
| 44 | $>10^{-5}$ |
| 45 | $>10^{-5}$ |

EXAMPLE 92

Effect of Azonafide Derivatives on Cell Migration

Cells of different cancer lines, i.e. U-373 MG (Glioma cancer), PC3 (prostate cancer and A549 (Lung cancer) were seeded on culture flask 48 hours before the migration experiment. On the test day, cells were treated with or without the azonafide derivatives mentioned in table 3 in closed Falcon dishes containing a buffered medium at a controlled temperature (37.0±0.1° C.) for 12 or 22 hours, as noted in the right column of table 3. The azonafide derivatives were used at three non-cytotoxic concentrations ($10^{-6}$ M, $10^{-7}$, $10^{-8}$ M). Migration of the cells was observed by means of a CCD-camera mounted on a phase-contrast microscope. Statistical analysis of the migration, with the non-parametric Mann-Whitney test, was established for 25% and 50% of the most motile cells and for the entire cell population. Table 3 below shows the anti-migratory effect of the compound according to the invention.

TABLE 3

| Compound of example | Cell lines | Maximum effects | Conditions |
|---|---|---|---|
| 3 | U-373MG | −31%/p < 0.001 | 22 hours on the 25% of most motile cells, at $10^{-6}$ M |
| 5 | A549 | −47%/p < 0.001 | 22 hours on the 25% of most motile cells, at $10^{-8}$ M |
| 6 | A549 | −29%/p < 0.05 | 22 hours on the 25% of most motile cells, at $10^{-8}$ M |
| 6 | PC3 | −24%/p < 0.05 | 22 hours on the 25% of most motile cells, at $10^{-8}$ M |
| 7 | A549 | −20%/p < 0.001 | 22 hours on the 100% of cells, at $10^{-6}$ M |
| 8 | U-373MG | −30%/p < 0.001 | 22 hours on the 25% of most motile cells, at $10^{-6}$ M |
| 8 | PC3 | −29%/p < 0.01 | 22 hours on the 25% of most motile cells, at $10^{-8}$ M |
| 9 | A549 | −40%/p < 0.001 | 12 hours on the 25% of most motile cells, at $10^{-6}$ M |
| 9 | A549 | −28%/p < 0.001 | 22 hours on the 25% of most motile cells, at $10^{-6}$ M |
| 9 | U-373MG | −31%/p < 0.001 | 12 and 22 hours on the 25% of most motile cells, at $10^{-7}$ M |
| 10 | A549 | −24%/p < 0.01 | 22 hours on the 25% of most motile cells, at $10^{-6}$ M |
| 11 | U-373MG | −18%/p < 0.05 | 22 hours on the 25% of most motile cells, at $10^{-6}$ M |
| 11 | PC3 | −27%/p < 0.01 | 22 hours on the 25% of most motile cells, at $10^{-7}$ M |
| 11 | PC3 | −37%/p < 0.001 | 22 hours on the 25% of most motile cells, at $10^{-6}$ M |
| 12 | U-373MG | −20%/p < 0.05 | 22 hours on the 25% of most motile cells, at $10^{-7}$ M |
| 13 | PC3 | −43%/p < 0.001 | 22 hours on the 25% of most motile cells, at $10^{-8}$ M |
| 13 | U-373MG | −24%/p < 0.01 | 22 hours on the 25% of most motile cells, at $10^{-7}$ M |
| 14 | A549 | −24%/p < 0.05 | 22 hours on the 25% of most motile cells, at $10^{-6}$ M |
| 15 | U-373MG | −51%/p < 0.001 | 22 hours on the 25% of most motile cells, at $10^{-6}$ M |
| 17 | A549 | −44%/p < 0.001 | 22 hours on the 25% of most motile cells, at $10^{-7}$ M |
| 17 | U-373MG | −42%/p < 0.001 | 22 hours on the 25% of most motile cells, at $10^{-7}$ M |
| 24 | A549 | −31%/p < 0.001 | 22 hours on the 25% of most motile cells, at $10^{-8}$ M |
| 25 | A549 | −28%/p < 0.001 | 22 hours on the 25% of most motile cells, at $10^{-7}$ M |
| 25 | PC3 | −21%/p < 0.05 | 22 hours on the 25% of most motile cells, at $10^{-8}$ M |
| 26 | A549 | −29%/p < 0.001 | 22 hours on the 25% of most motile cells, at $10^{-8}$ M |
| 27 | A549 | −28%/p < 0.01 | 22 hours on the 25% of most motile cells, at $10^{-6}$ M |
| 29 | A549 | −33%/p < 0.001 | 22 hours on the 25% of most motile cells, at $10^{-7}$ M |
| 29 | PC3 | −22%/p < 0.01 | 22 hours on the 25% of most motile cells, at $10^{-6}$ M |
| 31 | PC3 | −30%/p < 0.001 | 22 hours on the 25% of most motile cells, at $10^{-6}$ M |
| 31 | U-373MG | −60%/p < 0.001 | 22 hours on the 25% of most motile cells, at $10^{-6}$ M |

The data of table 3 demonstrate that the azonafide derivatives of examples 5, 6, 7, 8, 9, 10, 11, 12, 13, 14, 15, 17, 24, 25, 26, 27, 29 and 31 induced a decrease in the migration level of U-373 MG, PC-3 and/or A549 cancer cells at the non-cytotoxic concentrations of this study. In particular, the azonafide derivatives of examples 5, 6, 8, 9, 11, 13, 15, 17, 24, 26, 29 and 31 show significantly greater cell migration activity than the closest compounds known in the art, or similar cell migration activity at significantly lower concentrations.

EXAMPLES 93 to 135

Preparation of Compounds According to Formula (III) wherein R' is a Benzylidene Group The synthetic procedure of example 5 is repeated, except that 2,5-dihydroxybenzaldehyde is replaced with another aromatic aldehyde. In such a way the following compounds were obtained:

11-{[(1Z)-(2-methylbenzylidene]amino}-2-[2-(dimethylamino)ethyl]-1H-dibenzo[de,h]isoquinoline-1,3(2H)-dione (example 93) from o-tolualdehyde, 11-{[(1Z)-(3-methylbenzylidene]amino}-2-[2-(dimethylamino)ethyl]-1H-dibenzo[de,h]isoquinoline-1,3(2H)-dione (example 94) from m-tolualdehyde, 11-{[(1Z)-(4-methylbenzylidene]amino}-2-[2-(dimethylamino)ethyl]-1H-dibenzo[de,h]isoquinoline-1,3(2H)-dione (example 95) from p-tolualdehyde, 11-{[(1Z)-(2-methoxybenzylidene]amino}-2-[2-(dimethylamino)ethyl]-1H-dibenzo[de,h]isoquinoline-1,3(2H)-dione (example 96) from o-anisaldehyde, 11-{[(1Z)-(3-methoxybenzylidene]amino}-2-[2-(dimethylamino)ethyl]-1H-dibenzo[de,h]isoquinoline-1,3(2H)-dione (example 97) from m-anisaldehyde, 11-{[(1Z)-(4-methoxybenzylidene]amino}-2-[2-(dimethylamino)ethyl]-1H-dibenzo[de,h]isoquinoline-1,3(2H)-dione (example 98) from p-anisaldehyde, 11-{[(1Z)-(4-propoxybenzylidene]amino}-2-[2-(dimethylamino)ethyl]-1H-dibenzo[de,h]isoquinoline-1,3(2H)-dione (example 99) from 4-propoxybenzaldehyde, 11-{[(1Z)-(4-phenoxybenzylidene]amino}-2-[2-(dimethylamino)ethyl]-1H-dibenzo[de,h]isoquinoline-1,3(2H)-dione (example 100) from 4-phenoxy-benzaldehyde, 11-{[(1Z)-3-(3,4-dichlorophenoxy)benzylidene]amino}-2-[2-(dimethylamino)ethyl]-1H-dibenzo[de,h]isoquinoline-1,3(2H)-dione (example 101) from 3-(3,4-dichlorophenoxy)benzaldehyde, 11-{[(1Z)-3-(3,5-dichlorophenoxy)benzylidene]amino}-2-[2-(dimethylamino)ethyl]-1H-dibenzo[de,h]isoquinoline-1,3(2H)-dione (example 102) from 3-(3,5-dichlorophenoxy)benzaldehyde, 11-{[(1Z)-(2-bromobenzylidene]amino}-2-[2-(dimethylamino)ethyl]-1H-dibenzo[de,h]isoquinoline-1,3(2H)-dione (example 103) from 2-bromobenzaldehyde, 11-{[(1Z)-(3-bromobenzylidene]amino}-2-[2-(dimethylamino)ethyl]-1H-dibenzo[de,h]isoquinoline-1,3(2H)-dione (example 104) from 3-bromobenzaldehyde, 11-{[(1Z)-(4-bromobenzylidene]amino}-2-[2-(dimethylamino)ethyl]-1H-dibenzo[de,h]isoquinoline-1,3(2H)-dione (example 105) from 4-bromo-benzaldehyde, 11-{[(1Z)-(2-chlorobenzylidene]amino}-2-[2-(dimethylamino)ethyl]-1H-dibenzo[de,h]isoquinoline-1,3(2H)-dione (example 106) from 2-chlorobenzaldehyde, 11-{[(1Z)-(3-chlorobenzylidene]amino}-2-[2-(dimethylamino)ethyl]-1H-dibenzo[de,h]isoquinoline-1,3(2H)-dione (example 107) from 3-chlorobenzaldehyde, 11-{[(1Z)-(4-chlorobenzylidene]amino}-2-[2-(dimethylamino)ethyl]-1H-dibenzo[de,h]isoquinoline-1,3(2H)-dione (example 108) from 4-chlorobenzaldehyde, 11-{[(1Z)-(2-fluorobenzylidene]amino}-2-[2-(dimethylamino)ethyl]-1H-dibenzo[de,h]isoquinoline-1,3(2H)-dione (example 109) from 2-fluorobenzaldehyde, 11-{[(1Z)-(3-fluorobenzylidene]amino}-2-[2-(dimethylamino)ethyl]-1H-dibenzo[de,h]isoquinoline-1,3(2H)-dione (example 110) from 3-fluorobenzaldehyde, 11-{[(1Z)-(4-fluorobenzylidene]amino}-2-[2-(dimethylamino)ethyl]-1H-dibenzo[de,h]isoquinoline-1,3(2H)-dione (example 111) from 4-fluorobenzaldehyde, 11-{[(1Z)-(2,3-dichlorobenzylidene]amino}-2-[2-(dimethylamino)ethyl]-1H-dibenzo[de,h]isoquinoline-1,3(2H)-dione (example 112) from 2,3-dichlorobenzaldehyde, 11-{[(1Z)-(2,4-dichlorobenzylidene]amino}-2-[2-(dimethylamino)ethyl]-1H-dibenzo[de,h]isoquinoline-1,3(2H)-dione (example 113) from 2,4-dichlorobenzaldehyde, 11-{[(1Z)-(2,6-dichlorobenzylidene]amino}-2-[2-(dimethylamino)ethyl]-1H-dibenzo[de,h]isoquinoline-1,3(2H)-dione (example 114) from 2,6-dichlorobenzaldehyde, 11-{[(1Z)-(3,4-dichlorobenzylidene]amino}-2-[2-(dimethylamino)ethyl]-1H-dibenzo[de,h]isoquinoline-1,3(2H)-dione (example 115) from 3,4-dichlorobenzaldehyde, 11-{[(1Z)-(3,5-dichlorobenzylidene]amino}-2-[2-(dimethylamino)ethyl]-1H-dibenzo[de,h]isoquinoline-1,3(2H)-dione (example 116) from 3,5-dichlorobenzaldehyde, 11-{[(1Z)-(2,3-difluorobenzylidene]amino}-2-[2-(dimethylamino)ethyl]-1H-dibenzo[de,h]isoquinoline-1,3(2H)-dione (example 117) from 2,3-difluorobenzaldehyde, 11-{[(1Z)-(2,4-difluorobenzylidene]amino}-2-[2-(dimethylamino)ethyl]-1H-dibenzo[de,h]isoquinoline-1,3(2H)-dione (example 118) from 2,4-difluorobenzaldehyde, 11-{[(1Z)-(2,5-difluorobenzylidene]amino}-2-[2-(dimethylamino)ethyl]-1H-dibenzo[de,h]isoquinoline-1,3(2H)-dione (example 119) from 2,5-difluorobenzaldehyde, 11-{[(1Z)-(2,6-difluorobenzylidene]amino}-2-[2-(dimethylamino)ethyl]-1H-dibenzo[de,h]isoquinoline-1,3(2H)-dione (example 120) from 2,6-difluorobenzaldehyde, 11-{[(1Z)-(3,4-difluorobenzylidene]amino}-2-[2-(dimethylamino)ethyl]-1H-dibenzo[de,h]isoquinoline-1,3(2H)-dione (example 121) from 3,4-difluorobenzaldehyde, 11-{[(1Z)-(3,5-fluorobenzylidene]amino}-2-[2-(dimethylamino)ethyl]-1H-dibenzo[de,h]isoquinoline-1,3(2H)-dione (example 122) from 3,5-difluorobenzaldehyde, 11-{[(1Z)-(2,3,4-trifluorobenzylidene]amino}-2-[2-(dimethylamino)ethyl]-1H-dibenzo[de,h]isoquinoline-1,3(2H)-dione (example 123) from 2,3,4-trifluorobenzaldehyde, 11-{[(1Z)-(2-(trifluoromethyl)benzylidene]amino}-2-[2-(dimethylamino)ethyl]-1H-dibenzo[de,h]isoquinoline-1,3(2H)-dione (example 124) from 2-(trifluoromethyl)benzaldehyde, 11-{[(1Z)-(3-(trifluoromethyl)benzylidene]amino}-2-[2-(dimethylamino)ethyl]-1H-dibenzo[de,h]isoquinoline-1,3(2H)-dione (example 125) from 3-(trifluoromethyl)benzaldehyde, 11-{[(1Z)-(4-(trifluoromethyl)benzylidene]amino}-2-[2-(dimethylamino)ethyl]-1H-dibenzo[de,h]isoquinoline-1,3(2H)-dione (example 126) from 4-(trifluoromethyl)benzaldehyde, 11-{[(1Z)-(3-(trifluoromethoxy)benzylidene]amino}-2-[2-(dimethylamino)ethyl]-1H-dibenzo[de,h]isoquinoline-1,3(2H)-dione (example 127) from 3-(trifluoromethoxy)benzaldehyde, 11-{[(1Z)-(2-aminobenzylidene]amino}-2-[2-(dimethylamino)ethyl]-1H-dibenzo[de,h]isoquinoline-1,3(2H)-dione (example 128) from 2-amino-benzaldehyde, 11-{[(1Z)-(2-nitrobenzylidene]amino}-2-[2-(dimethylamino)ethyl]-1H-dibenzo[de,h]isoquinoline-1,3(2H)-dione (example 129) from 2-nitrobenzaldehyde, 11-{[(1Z)-(3-nitrobenzylidene]amino}-2-[2-(dimethylamino)ethyl]-1H-dibenzo[de,h]isoquinoline-1,3(2H)-dione (example 130) from 3-nitrobenzaldehyde, 11-{[(1Z)-(4-nitrobenzylidene]amino}-2-[2-(dimethylamino)ethyl]-1H-dibenzo[de,h]isoquinoline-1,3(2H)-dione (example 131) from 4-nitrobenzaldehyde, 11-{[(1Z)-(3-cyanobenzylidene]amino}-2-[2-(dimethylamino)ethyl]-1H-dibenzo[de,h]isoquinoline-1,3(2H)-dione (example 132) from 3-cyanobenzaldehyde, 11-{[(1Z)-(4-cyanobenzylidene]amino}-2-[2-(dimethylamino)ethyl]-1H-dibenzo[de,h]isoquinoline-1,3(2H)-dione (example 133) from 4-cyano-benzaldehyde, 11-{[(1Z)-(4-dimethylaminobenzylidene]amino}-2-[2-(dimethylamino)ethyl]-1H-dibenzo[de,h]isoquinoline-1,3(2H)-dione (example 134) from 4-(dimethylamino)benzaldehyde, and 11-{[(1Z)-(4-diethylaminobenzylidene]amino}-2-[2-(dimethylamino)ethyl]-1H-dibenzo[de,h]isoquinoline-1,3(2H)-dione (example 135) from 4-(diethylamino)benzaldehyde.

EXAMPLES 136 to 178

Preparation of Compounds According to Formula (IV) wherein R' is a Benzylidene Group The synthetic procedure of example 6 is repeated, except that 2,5-dihydroxybenzaldehyde is replaced with another aromatic aldehyde. In such a way the following compounds were obtained:

8-{[(1Z)-(2-methylbenzylidene]amino}-2-[2-(dimethylamino)ethyl]-1H-dibenzo[de,h]isoquinoline-1,3(2H)-dione (example 136) from o-tolualdehyde, 8-{[(1Z)-(3-methylbenzylidene]amino}-2-[2-(dimethylamino)ethyl]-1H-dibenzo[de,h]isoquinoline-1,3(2H)-dione (example 137) from m-tolualdehyde, 8-{[(1Z)-(4-methylbenzylidene]amino}-2-[2-(dimethylamino)ethyl]-1H-dibenzo[de,h]isoquinoline-1,3(2H)-dione (example 138) from p-tolualdehyde, 8-{[(1Z)-(2-methoxybenzylidene]amino}-2-[2-(dimethylamino)ethyl]-1H-dibenzo[de,h]isoquinoline-1,3(2H)-dione (example 139) from o-anisaldehyde, 8-{[(1Z)-(3-methoxybenzylidene]amino}-2-[2-(dimethylamino)ethyl]-1H-dibenzo[de,h]isoquinoline-1,3(2H)-dione (example 140) from m-anisaldehyde, 8-{[(1Z)-(4-methoxybenzylidene]amino}-2-[2-(dimethylamino)ethyl]-1H-dibenzo[de,h]isoquinoline-1,3(2H)-dione (example 141) from p-anisaldehyde, 8-{[(1Z)-(4-propoxybenzylidene]amino}-2-[2-(dimethylamino)ethyl]-1H-dibenzo[de,h]isoquinoline-1,3(2H)-dione (example 142) from 4-propoxybenzaldehyde, 8-{[(1Z)-(4-phenoxybenzylidene]amino}-2-[2-(dimethylamino)ethyl]-1H-dibenzo[de,h]isoquinoline-1,3(2H)-dione (example 143) from 4-phenoxy-benzaldehyde, 8-{[(1Z)-3-(3,4-dichlorophenoxy)benzylidene]amino}-2-[2-(dimethylamino)ethyl]-1H-dibenzo[de,h]isoquinoline-1,3(2H)-dione (example 144) from 3-(3,4-dichlorophenoxy)benzaldehyde, 8-{[(1Z)-3-(3,5-dichlorophenoxy)benzylidene]amino}-2-[2-(dimethylamino)ethyl]-1H-dibenzo[de,h]isoquinoline-1,3(2H)-dione (example 145) from 3-(3,5-dichlorophenoxy)benzaldehyde, 8-{[(1Z)-(2-bromobenzylidene]amino}-2-[2-(dimethylamino)ethyl]-1H-dibenzo[de,h]isoquinoline-1,3(2H)-dione (example 146) from 2-bromobenzaldehyde, 8-{[(1Z)-(3-bromobenzylidene]amino}-2-[2-(dimethylamino)ethyl]-1H-dibenzo[de,h]isoquinoline-1,3(2H)-dione (example 147) from 3-bromobenzaldehyde, 8-{[(1Z)-(4-bromobenzylidene]amino}-2-[2-(dimethylamino)ethyl]-1H-dibenzo[de,h]isoquinoline-1,3(2H)-dione (example 148) from 4-bromo-benzaldehyde, 8-{[(1Z)-(2-chlorobenzylidene]amino}-2-[2-(dimethylamino)ethyl]-1H-dibenzo[de,h]isoquinoline-1,3(2H)-dione (example 149) from 2-chlorobenzaldehyde, 8-{[(1Z)-(3-chlorobenzylidene]amino}-2-[2-(dimethylamino)ethyl]-1H-dibenzo[de,h]isoquinoline-1,3(2H)-dione (example 150) from 3-chlorobenzaldehyde, 8-{[(1Z)-(4-chlorobenzylidene]amino}-2-[2-(dimethylamino)ethyl]-1H-dibenzo[de,h]isoquinoline-1,3(2H)-dione (example 151) from 4-chlorobenzaldehyde, 8-{[(1Z)-(2-fluorobenzylidene]amino}-2-[2-(dimethylamino)ethyl]-1H-dibenzo[de,h]isoquinoline-1,3(2H)-dione (example 152) from 2-fluorobenzaldehyde, 8-{[(1Z)-(3-fluorobenzylidene]amino}-2-[2-(dimethylamino)ethyl]-1H-dibenzo[de,h]isoquinoline-1,3(2H)-dione (example 153) from 3-fluorobenzaldehyde, 8-{[(1Z)-(4-fluorobenzylidene]amino}-2-[2-(dimethylamino)ethyl]-1H-dibenzo[de,h]isoquinoline-1,3(2H)-dione (example 154) from 4-fluorobenzaldehyde, 8-{[(1Z)-(2,3-dichlorobenzylidene]amino}-2-[2-(dimethylamino)ethyl]-1H-dibenzo[de,h]isoquinoline-1,3(2H)-dione (example 155) from 2,3-dichlorobenzaldehyde, 8-{[(1Z)-(2,4-dichlorobenzylidene]amino}-2-[2-(dimethylamino)ethyl]-1H-dibenzo[de,h]isoquinoline-1,3(2H)-dione (example 156) from 2,4-dichlorobenzaldehyde, 8-{[(1Z)-(2,6-dichlorobenzylidene]amino}-2-[2-(dimethylamino)ethyl]-1H-dibenzo[de,h]isoquinoline-1,3(2H)-dione (example 157) from 2,6-dichlorobenzaldehyde, 8-{[(1Z)-(3,4-dichlorobenzylidene]amino}-2-[2-(dimethylamino)ethyl]-1H-dibenzo[de,h]isoquinoline-1,3(2H)-dione (example 158) from 3,4-dichlorobenzaldehyde, 8-{[(1Z)-(3,5-dichlorobenzylidene]amino}-2-[2-(dimethylamino)ethyl]-1H-dibenzo[de,h]isoquinoline-1,3(2H)-dione (example 159) from 3,5-dichlorobenzaldehyde, 8-{[(1Z)-(2,3-difluorobenzylidene]amino}-2-[2-(dimethylamino)ethyl]-1H-dibenzo[de,h]isoquinoline-1,3(2H)-dione (example 160) from 2,3-difluorobenzaldehyde, 8-{[(1Z)-(2,4-difluorobenzylidene]amino}-2-[2-(dimethylamino)ethyl]-1H-dibenzo[de,h]isoquinoline-1,3(2H)-dione (example 161) from 2,4-difluorobenzaldehyde, 8-{[(1Z)-(2,5-difluorobenzylidene]amino}-2-[2-(dimethylamino)ethyl]-1H-dibenzo[de,h]isoquinoline-1,3(2H)-dione (example 162) from 2,5-difluorobenzaldehyde, 8-{[(1Z)-(2,6-difluorobenzylidene]amino}-2-[2-(dimethylamino)ethyl]-1H-dibenzo[de,h]isoquinoline-1,3(2H)-dione (example 163) from 2,6-difluorobenzaldehyde, 8-{[(1Z)-(3,4-difluorobenzylidene]amino}-2-[2-(dimethylamino)ethyl]-1H-dibenzo[de,h]isoquinoline-1,3(2H)-dione (example 164) from 3,4-difluorobenzaldehyde, 8-{[(1Z)-(3,5-fluorobenzylidene]amino}-2-[2-(dimethylamino)ethyl]-1H-dibenzo[de,h]isoquinoline-1,3(2H)-dione (example 165) from 3,5-difluorobenzaldehyde, 8-{[(1Z)-(2,3,4-trifluorobenzylidene]amino}-2-[2-(dimethylamino)ethyl]-1H-dibenzo[de,h]isoquinoline-1,3(2H)-dione (example 166) from 2,3,4-trifluorobenzaldehyde, 8-{[(Z)-(2-(trifluoromethyl)benzylidene]amino}-2-[2-(dimethylamino)ethyl]-1H-dibenzo[de,h]isoquinoline-1,3(2H)-dione (example 167) from 2-(trifluoromethyl)benzaldehyde, 8-{[(1Z)-(3-(trifluoromethyl)benzylidene]amino}-2-[2-(dimethylamino)ethyl]-1H-dibenzo[de,h]isoquinoline-1,3(2H)-dione (example 168) from 3-(trifluoromethyl)benzaldehyde, 8-{[(1Z)-(4-(trifluoromethyl)benzylidene]amino}-2-[2-(dimethylamino)ethyl]-1H-dibenzo[de,h]isoquinoline-1,3(2H)-dione (example 169) from 4-(trifluoromethyl)benzaldehyde, 8-{[(1Z)-(3-(trifluoromethoxy)benzylidene]amino}-2-[2-(dimethylamino)ethyl]-1H-dibenzo[de,h]isoquinoline-1,3(2H)-dione (example 170) from 3-(trifluoromethoxy)benzaldehyde, 8-{[(1Z)-(2-aminobenzylidene]amino}-2-[2-(dimethylamino)ethyl]-1H-dibenzo[de,h]isoquinoline-1,3(2H)-dione (example 171) from 2-amino-benzaldehyde, 8-{[(1Z)-(2-nitrobenzylidene]amino}-2-[2-(dimethylamino)ethyl]-1H-dibenzo[de,h]isoquinoline-1,3(2H)-dione (example 172) from 2-nitrobenzaldehyde, 8-{[(1Z)-(3-nitrobenzylidene]amino}-2-[2-(dimethylamino)ethyl]-1H-dibenzo[de,h]isoquinoline-1,3(2H)-dione (example 173) from 3-nitrobenzaldehyde, 8-{[(1Z)-(4-nitrobenzylidene]amino}-2-[2-(dimethylamino)ethyl]-1H-dibenzo[de,h]isoquinoline-1,3(2H)-dione (example 174) from 4-nitrobenzaldehyde, 8-{[(1Z)-(3-cyanobenzylidene]amino}-2-[2-(dimethylamino)ethyl]-1H-dibenzo[de,h]isoquinoline-1,3(2H)-dione (example 175) from 3-cyanobenzaldehyde, 8-{[(1Z)-(4-cyanobenzylidene]amino}-2-[2-(dimethylamino)ethyl]-1H-dibenzo[de,h]isoquinoline-1,3(2H)-dione (example 176) from 4-cyano-benzaldehyde, 8-{[(1Z)-(4-dimethylaminobenzylidene]amino}-2-[2-(dimethylamino)ethyl]-1H-dibenzo[de,h]isoquinoline-1,3(2H)-dione (example 177) from 4-(dimethylamino)benzaldehyde, and 8-{[(1Z)-(4-diethylaminobenzylidene]amino}-2-[2-(dimethylamino)ethyl]-1H-dibenzo[de,h]isoquinoline-1,3(2H)-dione (example 178) from 4-(diethylamino)benzaldehyde.

EXAMPLES 179 and 180

Preparation of Compounds According to Formula (IV) wherein R' is a Cycloalkylmethylidene Group The synthetic procedure of example 6 is repeated, except that 2,5-dihydroxybenzaldehyde is replaced with a cycloaliphatic aldehyde. In such a way the following compounds were obtained:

8-{[(1Z)-(cyclohexylmethylidene]amino}-2-[2-(dimethylamino)ethyl]-1H-dibenzo[de,h]isoquinoline-1,3(2H)-dione (example 179) from cyclohexanecarboxaldehyde, and 8-{[(1Z)-(cyclooctylmethylidene]amino}-2-[2-(dimethylamino)ethyl]-1H-dibenzo[de,h]isoquinoline-1,3(2H)-dione (example 180) from cyclooctanecarboxaldehyde.

EXAMPLES 181 and 182

Preparation of Compounds According to Formula (III) wherein R' is a Cycloalkylmethylidene Group The synthetic procedure of example 5 is repeated, except that 2,5-dihydroxybenzaldehyde is replaced with a cycloaliphatic aldehyde. In such a way the following compounds were obtained:

11-{[(1Z)-(cyclohexylmethylidene]amino}-2-[2-(dimethylamino)ethyl]-1H-dibenzo[de,h]isoquinoline-1,3(2H)-dione (example 181) from cyclohexanecarboxaldehyde, and 11-{[(1Z)-(cyclooctylmethylidene]amino}-2-[2-(dimethylamino)ethyl]-1H-dibenzo[de,h]isoquinoline-1,3(2H)-dione (example 182) from cyclooctanecarboxaldehyde.

EXAMPLES 183 to 188

Preparation of Compounds According to Formula (III) wherein R' is a Heterocyclic-Methylidene Group The synthetic procedure of example 5 is repeated, except that 2,5-dihydroxybenzaldehyde is replaced with a heterocyclic aldehyde. In such a way the following compounds were obtained:

11-{[(1Z)-(pyrrol-2-ylmethylidene]amino}-2-[2-(dimethylamino)ethyl]-1H-dibenzo[de,h]isoquinoline-1,3(2H)-dione (example 183) from pyrrole-2-carboxaldehyde, 11-{[(1Z)-(thien-2-ylmethylidene]amino}-2-[2-(dimethylamino)ethyl]-1H-dibenzo[de,h]isoquinoline-1,3(2H)-dione (example 184) from 2-thiophene-carboxaldehyde, 11-{[(1Z)-(thien-3-ylmethylidene]amino}-2-[2-(dimethylamino)ethyl]-1H-dibenzo[de,h]isoquinoline-1,3(2H)-dione (example 185) from 3-thiophene-carboxaldehyde, 11-{[(1Z)-(pyrrolidinylmethylidene]amino}-2-[2-(dimethylamino)ethyl]-1H-dibenzo[de,h]isoquinoline-1,3(2H)-dione (example 186) from pyrrolidine-carboxaldehyde, 11-{[(1Z)-(pyrid-4-ylmethylidene]amino}-2-[2-(dimethylamino)ethyl]-1H-dibenzo[de,h]isoquinoline-1,3(2H)-dione (example 187) from 4-pyridinecarboxaldehyde, and 11-{[(1Z)-(pyrid-3-ylmethylidene]amino}-2-[2-(dimethylamino)ethyl]-1H-dibenzo[de,h]isoquinoline-1,3(2H)-dione (example 188) from 3-pyridinecarboxaldehyde.

EXAMPLES 189 to 194

Preparation of Compounds According to Formula (IV) wherein R' is a Heterocyclic-Methylidene Group The synthetic procedure of example 6 is repeated, except that 2,5-dihydroxybenzaldehyde is replaced with a heterocyclic aldehyde. In such a way the following compounds were obtained:

8-{[(1Z)-(pyrrol-2-ylmethylidene]amino}-2-[2-(dimethylamino)ethyl]-1H-dibenzo[de,h]isoquinoline-1,3(2H)-dione (example 189) from pyrrole-2-carboxaldehyde, 8-{[(1Z)-(thien-2-ylmethylidene]amino}-2-[2-(dimethylamino)ethyl]-1H-dibenzo[de,h]isoquinoline-1,3(2H)-dione (example 190) from 2-thiophene-carboxaldehyde, 8-{[(1Z)-(thien-3-ylmethylidene]amino}-2-[2-(dimethylamino)ethyl]-1H-dibenzo[de,h]isoquinoline-1,3(2H)-dione (example 191) from 3-thiophene-carboxaldehyde, 8-{[(1Z)-(pyrrolidinylmethylidene]amino}-2-[2-(dimethylamino)ethyl]-1H-dibenzo[de,h]isoquinoline-1,3(2H)-dione (example 192) from pyrrolidine-carboxaldehyde, 11-{[(1Z)-(pyrid-4-ylmethylidene]amino}-2-[2-(dimethylamino)ethyl]-1H-dibenzo[de,h]isoquinoline-1,3(2H)-dione (example 193) from 4-pyridinecarboxaldehyde, and 11-{[(1Z)-(pyrid-3-ylmethylidene]amino}-2-[2-(dimethylamino)ethyl]-1H-dibenzo[de,h]isoquinoline-1,3(2H)-dione (example 194) from 3-pyridinecarboxaldehyde.

What is claimed is:

1. A substituted azonafide derivative selected from the group consisting of:

11-{[(1Z)-(2,5-dihydroxyphenyl)methylidene]amino}-2-[2-(dimethylamino)ethyl]-1H-dibenzo[de,h]isoquinoline-1,3(2H)-dione;

8-{[(1Z)-(2,5-dihydroxyphenyl)methylidene]amino}-2-[2-(dimethylamino)ethyl]-1H-dibenzo[de,h]isoquinoline-1,3(2H)-dione;

11-{[(1Z)-1,3-benzodioxol-5-ylmethylidene]amino}-2-[2-(dimethylamino)ethyl]-1H-dibenzo[de,h]isoquinoline-1,3(2H)-dione;

8-{[(1E)-1,3-benzodioxol-5-ylmethylidene]amino}-2-[2-(dimethylamino)ethyl]-1H-dibenzo[de,h]isoquinoline-1,3(2H)-dione;

methyl {2-[2-(dimethylamino)ethyl]-1,3-dioxo-2,3-dihydro-1H-dibenzo[de,h]isoquinolin-11-yl}carbamate;

4-chloro-N-{2-[2-(dimethylamino)ethyl]-1,3-dioxo-2,3-dihydro-1H-dibenzo[de,h]isoquinolin-11-yl}butanamide;

2-(4-chlorophenyl)-N-{2-[2-(dimethylamino)ethyl]-1,3-dioxo-2,3-dihydro-1H-dibenzo[de,h]isoquinolin-11-yl}acetamide;

1-(1,3-benzodioxol-5-yl)-3-{2-[2-(dimethylamino)ethyl]-1,3-dioxo-2,3-dihydro-1H-dibenzo[de,h]isoquinolin-11-yl}urea;

1-{2-[2-(dimethylamino)ethyl]-1,3-dioxo-2,3-dihydro-1H-dibenzo[de,h]isoquinolin-11-yl}-3-pentylurea;

1-(1,3-benzodioxol-5-yl)-3-{2-[2-(dimethylamino)ethyl]-1,3-dioxo-2,3-dihydro-1H-dibenzo[de,h]isoquinolin-8-yl}urea;

1-(1,3-benzodioxol-5-yl)-3-{2-[2-(dimethylamino)ethyl]-1,3-dioxo-2,3-dihydro-1H-dibenzo[de,h]isoquinolin-8-yl}urea hydrochloride;
N-({2-[2-(dimethylamino)ethyl]-1,3-dioxo-2,3-dihydro-1H-dibenzo[de,h]isoquinolin-8-yl}carbamoyl)benzamide hydrochloride;
ethyl {2-[2-(dimethylamino)ethyl]-1,3-dioxo-2,3-dihydro-1H-dibenzo[de,h]isoquinolin-11-yl}carbamate;
phenyl {2-[2-(dimethylamino)ethyl]-1,3-dioxo-2,3-dihydro-1H-dibenzo[de,h]isoquinolin-11-yl}carbamate;
N-{2-[2-(dimethylamino)ethyl]-1,3-dioxo-2,3-dihydro-1H-dibenzo[de,h]isoquinolin-11-yl}-3-oxododecanamide;
N-{2-[2-(dimethylamino)ethyl]-1,3-dioxo-2,3-dihydro-1H-dibenzo[de,h]isoquinolin-11-yl}-3-oxo-5-phenylpentanamide;
ethyl 6-({2-[2-(dimethylamino)ethyl]-1,3-dioxo-2,3-dihydro-1H-dibenzo[de,h]isoquinolin-11-yl}amino)-4,6-dioxohexanoate;
4-fluorophenyl {2-[2-(dimethylamino)ethyl]-1,3-dioxo-2,3-dihydro-1H-dibenzo[de,h]isoquinolin-11-yl}carbamate;
octyl {2-[2-(dimethylamino)ethyl]-1,3-dioxo-2,3-dihydro-1H-dibenzo[de,h]isoquinolin-11-yl}carbamate;
allyl {2-[2-(dimethylamino)ethyl]-1,3-dioxo-2,3-dihydro-1H-dibenzo[de,h]isoquinolin-11-yl}carbamate;
isobutyl {2-[2-(dimethylamino)ethyl]-1,3-dioxo-2,3-dihydro-1H-dibenzo[de,h]isoquinolin-11-yl}carbamate;
4-chlorobutyl {2-[2-(dimethylamino)ethyl]-1,3-dioxo-2,3-dihydro-1H-dibenzo[de,h]isoquinolin-11-yl}carbamate;
n-butyl {2-[2-(dimethylamino)ethyl]-1,3-dioxo-2,3-dihydro-1H-dibenzo[de,h]isoquinolin-11-yl}carbamate;
1-{2-[2-(dimethylamino)ethyl]-1,3-dioxo-2,3-dihydro-1H-dibenzo[de,h]isoquinolin-11-yl}-3-[4-bromophenyl]thiourea;
1-{2-[2-(dimethylamino)ethyl]-1,3-dioxo-2,3-dihydro-1H-dibenzo[de,h]isoquinolin-11-yl}-3-[4-(trifluoromethoxy)phenyl]thiourea;
1-{2-[2-(dimethylamino)ethyl]-1,3-dioxo-2,3-dihydro-1H-dibenzo[de,h]isoquinolin-11-yl}-3-[2-methoxyethyl]thiourea;
1-{2-[2-(dimethylamino)ethyl]-1,3-dioxo-2,3-dihydro-1H-dibenzo[de,h]isoquinolin-11-yl}-3-[4-isopropylphenyl]thiourea;
1-{2-[2-(dimethylamino)ethyl]-1,3-dioxo-2,3-dihydro-1H-dibenzo[de,h]isoquinolin-11-yl}-3-[4-methoxyphenyl]thiourea;
1-{2-[2-(dimethylamino)ethyl]-1,3-dioxo-2,3-dihydro-1H-dibenzo[de,h]isoquinolin-11-yl}-3-[ethyl]thiourea;
1-{2-[2-(dimethylamino)ethyl]-1,3-dioxo-2,3-dihydro-1H-dibenzo[de,h]isoquinolin-11-yl}-3-[allyl]thiourea;
1-{2-[2-(dimethylamino)ethyl]-1,3-dioxo-2,3-dihydro-1H-dibenzo[de,h]isoquinolin-11-yl}-3-[2-methoxyphenyl]thiourea;
1-{2-[2-(dimethylamino)ethyl]-1,3-dioxo-2,3-dihydro-1H-dibenzo[de,h]isoquinolin-11-yl}-3-(3-pyridyl]thiourea;
1-{2-[2-(dimethylamino)ethyl]-1,3-dioxo-2,3-dihydro-1H-dibenzo[de,h]isoquinolin-11-yl}-3-(2-trifluoromethoxy4-bromophenyl]thiourea;
1-{2-[2-(dimethylamino)ethyl]-1,3-dioxo-2,3-dihydro-1H-dibenzo[de,h]isoquinolin-11-yl}-3-(2-furylmethyl]thiourea;
1-{2-[2-(dimethylamino)ethyl]-1,3-dioxo-2,3-dihydro-1H-dibenzo[de,h]isoquinolin-11-yl}-3-[4-trifluoromethylphenyl]thiourea;
1-(1,3-benzodioxol-4-yl)-3-{2-[2-(dimethylamino)ethyl]-1,3-dioxo-2,3-dihydro-1H-dibenzo[de,h]isoquinolin-11-yl}thiourea;
1-(2,1,3-benzothiadiazol-5-yl)-3-{2-[2-(dimethylamino)ethyl]-1,3-dioxo-2,3-dihydro-1H-dibenzo[de,h]isoquinolin-11-yl}thiourea;
1-(1,3-benzodioxol-4-ylmethyl)-3-{2-[2-(dimethylamino)ethyl]-1,3-dioxo-2,3-dihydro-1H-dibenzo[de,h]isoquinolin-11-yl}thiourea;
1-{2-[2-(dimethylamino)ethyl]-1,3-dioxo-2,3-dihydro-1H-dibenzo[de,h]isoquinolin-11-yl}-3-[2-(trifluoromethoxy)phenyl]thiourea;
11-{[(1Z)-(2-methylbenzylidene]amino}-2-[2-(dimethylamino)ethyl]-1H-dibenzo[de,h]isoquinoline-1,3(2H)-dione;
11-{[(1Z)-(3-methylbenzylidene]amino}-2-[2-(dimethylamino)ethyl]-1H-dibenzo[de,h]isoquinoline-1,3(2H)-dione;
11-{[(1Z)-(4-methylbenzylidene]amino}-2-[2-(dimethylamino)ethyl]-1H-dibenzo[de,h]isoquinoline-1,3(2H)-dione;
11-{[(1Z)-(2-methoxybenzylidene]amino}-2-[2-(dimethylamino)ethyl]-1H-dibenzo[de,h]isoquinoline-1,3(2H)-dione;
11-{[(1Z)-(3-methoxybenzylidene]amino}-2-[2-(dimethylamino)ethyl]-1H-dibenzo[de,h]isoquinoline-1,3(2H)-dione;
11-{[(1Z)-(4-methoxybenzylidene]amino}-2-[2-(dimethylamino)ethyl]-1H-dibenzo[de,h]isoquinoline-1,3(2H)-dione;
11-{[(1Z)-(4-propoxybenzylidene]amino}-2-[2-(dimethylamino)ethyl]-1H-dibenzo[de,h]isoquinoline-1,3(2H)-dione;
11-{[(1Z)-(4-phenoxybenzylidene]amino}-2-[2-(dimethylamino)ethyl]-1H-dibenzo[de,h]isoquinoline-1,3(2H)-dione;
11-{[(1Z)-3-(3,4-dichlorophenoxy)benzylidene]amino}-2-[2-(dimethylamino)ethyl]-1H-dibenzo[de,h]isoquinoline-1,3(2H)-dione;
11-{[(1Z)-3-(3,5-dichlorophenoxy)benzylidene]amino}-2-[2-(dimethylamino)ethyl]-1H-dibenzo[de,h]isoquinoline-1,3(2H)-dione;
11-{[(1Z)-(2-bromobenzylidene]amino}-2-[2-(dimethylamino)ethyl]-1H-dibenzo[de,h]isoquinoline-1,3(2H)-dione;
11-{[(1Z)-(3-bromobenzylidene]amino}-2-[2-(dimethylamino)ethyl]-1H-dibenzo[de,h]isoquinoline-1,3(2H)-dione;
11-{[(1Z)-(4-bromobenzylidene]amino}-2-[2-(dimethylamino)ethyl]-1H-dibenzo[de,h]isoquinoline-1,3(2H)-dione;
11-{[(1Z)-(2-chlorobenzylidene]amino}-2-[2-(dimethylamino)ethyl]-1H-dibenzo[de,h]isoquinoline-1,3(2H)-dione;
11-{[(1Z)-(3-chlorobenzylidene]amino}-2-[2-(dimethylamino)ethyl]-1H-dibenzo[de,h]isoquinoline-1,3(2H)-dione;
11-{[(1Z)-(4-chlorobenzylidene]amino}-2-[2-(dimethylamino)ethyl]-1H-dibenzo[de,h]isoquinoline-1,3(2H)-dione;
11-{[(1Z)-(2-fluorobenzylidene]amino}-2-[2-(dimethylamino)ethyl]-1H-dibenzo[de,h]isoquinoline-1,3(2H)-dione;
11-{[(1Z)-(3-fluorobenzylidene]amino}-2-[2-(dimethylamino)ethyl]-1H-dibenzo[de,h]isoquinoline-1,3(2H)-dione;
11-{[(1Z)-(4-fluorobenzylidene]amino}-2-[2-(dimethylamino)ethyl]-1H-dibenzo[de,h]isoquinoline-1,3(2H)-dione;
11-{[(1Z)-(2,3-dichlorobenzylidene]amino}-2-[2-(dimethylamino)ethyl]-1H-dibenzo[de,h]isoquinoline-1,3(2H)-dione;

11-{[(1Z)-(2,4-dichlorobenzylidene]amino}-2-[2-(dimethylamino)ethyl]-1H-dibenzo[de,h]isoquinoline-1,3(2H)-dione;

11-{[(1Z)-(2,6-dichlorobenzylidene]amino}-2-[2-(dimethylamino)ethyl]-1H-dibenzo[de,h]isoquinoline-1,3(2H)-dione;

11-{[(1Z)-(3,4-dichlorobenzylidene]amino}-2-[2-(dimethylamino)ethyl]-1H-dibenzo[de,h]isoquinoline-1,3(2H)-dione;

11-{[(1Z)-(3,5-dichlorobenzylidene]amino}-2-[2-(dimethylamino)ethyl]-1H-dibenzo[de,h]isoquinoline-1,3(2H)-dione;

11-{[(1Z)-(2,3-difluorobenzylidene]amino}-2-[2-(dimethylamino)ethyl]-1H-dibenzo[de,h]isoquinoline-1,3(2H)-dione;

11-{[(1Z)-(2,4-difluorobenzylidene]amino}-2-[2-(dimethylamino)ethyl]-1H-dibenzo[de,h]isoquinoline-1,3(2H)-dione;

11-{[(1Z)-(2,5-difluorobenzylidene]amino}-2-[2-(dimethylamino)ethyl]-1H-dibenzo[de,h]isoquinoline-1,3(2H)-dione;

11-{[(1Z)-(2,6-difluorobenzylidene]amino}-2-[2-(dimethylamino)ethyl]-1H-dibenzo[de,h]isoquinoline-1,3(2H)-dione;

11-{[(1Z)-(3,4-difluorobenzylidene]amino}-2-[2-(dimethylamino)ethyl]-1H-dibenzo[de,h]isoquinoline-1,3(2H)-dione;

11-{[(1Z)-(3,5-fluorobenzylidene]amino}-2-[2-(dimethylamino)ethyl]-1H-dibenzo[de,h]isoquinoline-1,3(2H)-dione;

11-{[(1Z)-(2,3,4-trifluorobenzylidene]amino}-2-[2-(dimethylamino)ethyl]-1H-dibenzo[de,h]isoquinoline-1,3(2H)-dione;

11-{[(1Z)-(2-(trifluoromethyl)benzylidene]amino}-2-[2-(dimethylamino)ethyl]-1H-dibenzo[de,h]isoquinoline-1,3(2H)-dione;

11-{[(1Z)-(3-(trifluoromethyl)benzylidene]amino}-2-[2-(dimethylamino)ethyl]-1H-dibenzo[de,h]isoquinoline-1,3(2H)-dione;

11-{[(1Z)-(4-(trifluoromethyl)benzylidene]amino}-2-[2-(dimethylamino)ethyl]-1H-dibenzo[de,h]isoquinoline-1,3(2H)-dione;

11-{[(1Z)-(3-(trifluoromethoxy)benzylidene]amino}-2-[2-(dimethylamino)ethyl]-1H-dibenzo[de,h]isoquinoline-1,3(2H)-dione;

11-{[(1Z)-(2-aminobenzylidene]amino}-2-[2-(dimethylamino)ethyl]-1H-dibenzo[de,h]isoquinoline-1,3(2H)-dione;

11-{[(1Z)-(2-nitrobenzylidene]amino}-2-[2-(dimethylamino)ethyl]-1H-dibenzo[de,h]isoquinoline-1,3(2H)-dione;

11-{[(1Z)-(3-nitrobenzylidene]amino}-2-[2-(dimethylamino)ethyl]-1H-dibenzo[de,h]isoquinoline-1,3(2H)-dione;

11-{[(1Z)-(4-nitrobenzylidene]amino}-2-[2-(dimethylamino)ethyl]-1H-dibenzo[de,h]isoquinoline-1,3(2H)-dione;

11-{[(Z)-(3-cyanobenzylidene]amino}-2-[2-(dimethylamino)ethyl]-1H-dibenzo[de,h]isoquinoline-1,3(2H)-dione;

11-{[(Z)-(4-cyanobenzylidene]amino}-2-[2-(dimethylamino)ethyl]-1H-dibenzo[de,h]isoquinoline-1,3(2H)-dione;

1-{[(1Z)-(4-dimethylaminobenzylidene]amino}-2-[2-(dimethylamino)ethyl]-1H-dibenzo[de,h]isoquinoline-1,3(2H)-dione;

11-{[(1Z)-(4-diethylaminobenzylidene]amino}-2-[2-(dimethylamino)ethyl]-1H-dibenzo[de,h]isoquinoline-1,3(2H)-dione;

8-{[(1Z)-(2-methylbenzylidene]amino}-2-[2-(dimethylamino)ethyl]-1H-dibenzo[de,h]isoquinoline-1,3(2H)-dione;

8-{[(1Z)-(3-methylbenzylidene]amino}-2-[2-(dimethylamino)ethyl]-1H-dibenzo[de,h]isoquinoline-1,3(2H)-dione;

8-{[(1Z)-(4-methylbenzylidene]amino}-2-[2-(dimethylamino)ethyl]-1H-dibenzo[de,h]isoquinoline-1,3(2H)-dione;

8-{[(1Z)-(2-methoxybenzylidene]amino}-2-[2-(dimethylamino)ethyl]-1H-dibenzo[de,h]isoquinoline-1,3(2H)-dione;

8-{[(1Z)-(3-methoxybenzylidene]amino}-2-[2-(dimethylamino)ethyl]-1H-dibenzo[de,h]isoquinoline-1,3(2H)-dione;

8-{[(1Z)-(4-methoxybenzylidene]amino}-2-[2-(dimethylamino)ethyl]-1H-dibenzo[de,h]isoquinoline-1,3(2H)-dione;

8-{[(1Z)-(4-propoxybenzylidene]amino}-2-[2-(dimethylamino)ethyl]-1H-dibenzo[de,h]isoquinoline-1,3(2H)-dione;

8-{[(1Z)-(4-phenoxybenzylidene]amino}-2-[2-(dimethylamino)ethyl]-1H-dibenzo[de,h]isoquinoline-1,3(2H)-dione;

8-{[(1Z)-3-(3,4-dichlorophenoxy)benzylidene]amino}-2-[2-(dimethylamino)ethyl]-1H-dibenzo[de,h]isoquinoline-1,3(2H)-dione;

8-{[(1Z)-3-(3,5-dichlorophenoxy)benzylidene]amino}-2-[2-(dimethylamino)ethyl]-1H-dibenzo[de,h]isoquinoline-1,3(2H)-dione;

8-{[(1Z)-(2-bromobenzylidene]amino}-2-[2-(dimethylamino)ethyl]-1H-dibenzo[de,h]isoquinoline-1,3(2H)-dione;

8-{[(1Z)-(3-bromobenzylidene]amino}-2-[2-(dimethylamino)ethyl]-1H-dibenzo[de,h]isoquinoline-1,3(2H)-dione;

8-{[(1Z)-(4-bromobenzylidene]amino}-2-[2-(dimethylamino)ethyl]-1H-dibenzo[de,h]isoquinoline-1,3(2H)-dione;

8-{[(1Z)-(2-chlorobenzylidene]amino}-2-[2-(dimethylamino)ethyl]-1H-dibenzo[de,h]isoquinoline-1,3(2H)-dione;

8-{[(1Z)-(3-chlorobenzylidene]amino}-2-[2-(dimethylamino)ethyl]-1H-dibenzo[de,h]isoquinoline-1,3(2H)-dione;

8-{[(1Z)-(4-chlorobenzylidene]amino}-2-[2-(dimethylamino)ethyl]-1H-dibenzo[de,h]isoquinoline-1,3(2H)-dione;

8-{[(1Z)-(2-fluorobenzylidene]amino}-2-[2-(dimethylamino)ethyl]-1H-dibenzo[de,h]isoquinoline-1,3(2H)-dione;

8-{[(1Z)-(3-fluorobenzylidene]amino}-2-[2-(dimethylamino)ethyl]-1H-dibenzo[de,h]isoquinoline-1,3(2H)-dione;

8-{[(1Z)-(4-fluorobenzylidene]amino}-2-[2-(dimethylamino)ethyl]-1H-dibenzo[de,h]isoquinoline-1,3(2H)-dione;

8-{[(1Z)-(2,3-dichlorobenzylidene]amino}-2-[2-(dimethylamino)ethyl]-1H-dibenzo[de,h]isoquinoline-1,3(2H)-dione;

8-{[(1Z)-(2,4-dichlorobenzylidene]amino}-2-[2-(dimethylamino)-ethyl]-1H-dibenzo[de,h]isoquinoline-1,3(2H)-dione;

8-{[(1Z)-(2,6-dichlorobenzylidene]amino}-2-[2-(dimethylamino)ethyl]-1H-dibenzo[de,h]isoquinoline-1,3(2H)-dione;

8-{[(1Z)-(3,4-dichlorobenzylidene]amino}-2-[2-(dimethylamino)ethyl]-1H-dibenzo[de,h]isoquinoline-1,3(2H)-dione;

8-{[(1Z)-(3,5-dichlorobenzylidene]amino}-2-[2-(dimethylamino)ethyl]-1H-dibenzo[de,h]isoquinoline-1,3(2H)-dione;
8-{[(1Z)-(2,3-difluorobenzylidene]amino}-2-[2-(dimethylamino)ethyl]-1H-dibenzo[de,h]isoquinoline-1,3(2H)-dione;
8-{[(1Z)-(2,4-difluorobenzylidene]amino}-2-[2-(dimethylamino)ethyl]-1H-dibenzo[de,h]isoquinoline-1,3(2H)-dione;
8-{[(1Z)-(2,5-difluorobenzylidene]amino}-2-[2-(dimethylamino)ethyl]-1H-dibenzo[de,h]isoquinoline-1,3(2H)-dione;
8-{[(1Z)-(2,6-difluorobenzylidene]amino}-2-[2-(dimethylamino)ethyl]-1H-dibenzo[de,h]isoquinoline-1,3(2H)-dione;
8-{[(1Z)-(3,4-difluorobenzylidene]amino}-2-[2-(dimethylamino)ethyl]-1H-dibenzo[de,h]isoquinoline-1,3(2H)-dione;
8-{[(1Z)-(3,5-fluorobenzylidene]amino}-2-[2-(dimethylamino)ethyl]-1H-dibenzo[de,h]isoquinoline-1,3(2H)-dione;
8-{[(1Z)-(2,3,4-trifluorobenzylidene]amino}-2-[2-(dimethylamino)ethyl]-1H-dibenzo[de,h]isoquinoline-1,3(2H)-dione;
8-{[(1Z)-(2-(trifluoromethyl)benzylidene]amino}-2-[2-(dimethylamino)ethyl]-1H-dibenzo[de,h]isoquinoline-1,3(2H)-dione;
8-{[(1Z)-(3-(trifluoromethyl)benzylidene]amino}-2-[2-(dimethylamino)ethyl]-1H-dibenzo[de,h]isoquinoline-1,3(2H)-dione;
8-{[(1Z)-(4-(trifluoromethyl)benzylidene]amino}-2-[2-(dimethylamino)ethyl]-1H-dibenzo[de,h]isoquinoline-1,3(2H)-dione;
8-{[(1Z)-(3-(trifluoromethoxy)benzylidene]amino}-2-[2-(dimethylamino)ethyl]-1H-dibenzo[de,h]isoquinoline-1,3(2H)-dione;
8-{[(1Z)-(2-aminobenzylidene]amino}-2-[2-(dimethylamino)ethyl]-1H-dibenzo[de,h]isoquinoline-1,3(2H)-dione;
8-{[(1Z)-(2-nitrobenzylidene]amino}-2-[2-(dimethylamino)ethyl]-1H-dibenzo[de,h]isoquinoline-1,3(2H)-dione;
8-{[(1Z)-(3-nitrobenzylidene]amino}-2-[2-(dimethylamino)ethyl]-1H-dibenzo[de,h]isoquinoline-1,3(2H)-dione;
8-{[(1Z)-(4-nitrobenzylidene]amino}-2-[2-(dimethylamino)ethyl]-1H-dibenzo[de,h]isoquinoline-1,3(2H)-dione;
8-{[(1Z)-(3-cyanobenzylidene]amino}-2-[2-(dimethylamino)ethyl]-1H-dibenzo[de,h]isoquinoline-1,3(2H)-dione;
8-{[(1Z)-(4-cyanobenzylidene]amino}-2-[2-(dimethylamino)ethyl]-1H-dibenzo[de,h]isoquinoline-1,3(2H)-dione;
8-{[(1Z)-(4-dimethylaminobenzylidene]amino}-2-[2-(dimethylamino)ethyl]-1H-dibenzo[de,h]isoquinoline-1,3(2H)-dione;
8-{[(1Z)-(4-diethylaminobenzylidene]amino}-2-[2-(dimethylamino)ethyl]-1H-dibenzo[de,h]isoquinoline-1,3(2H)-dione;
11-{[(1Z)-(cyclohexylmethylidene]amino}-2-[2-(dimethylamino)ethyl]-1H-dibenzo[de,h]isoquinoline-1,3(2H)-dione;
11-{[(1Z)-(cyclooctylmethylidene]amino}-2-[2-(dimethylamino)ethyl]-1H-dibenzo[de,h]isoquinoline-1,3(2H)-dione;
8-{[(1Z)-(cyclohexylmethylidene]amino}-2-[2-(dimethylamino)ethyl]-1H-dibenzo[de,h]isoquinoline-1,3(2H)-dione;
8-{[(1Z)-(cyclooctylmethylidene]amino}-2-[2-(dimethylamino)ethyl]-1H-dibenzo[de,h]isoquinoline-1,3(2H)-dione;
11-{[(1Z)-(pyrrol-2-ylmethylidene]amino}-2-[2-(dimethylamino)ethyl]-1H-dibenzo[de,h]isoquinoline-1,3(2H)-dione;
11-{[(1Z)-(thien-2-ylmethylidene]amino}-2-[2-(dimethylamino)ethyl]-1H-dibenzo[de,h]isoquinoline-1,3(2H)-dione;
11-{[(1Z)-(thien-3-ylmethylidene]amino}-2-[2-(dimethylamino)ethyl]-1H-dibenzo[de,h]isoquinoline-1,3(2H)-dione;
11-{[(1Z)-(pyrrolidinylmethylidene]amino}-2-[2-(dimethylamino)ethyl]-1H-dibenzo[de,h]isoquinoline-1,3(2H)-dione;
11-{[(1Z)-(pyrid-4-ylmethylidene]amino}-2-[2-(dimethylamino)ethyl]-1H-dibenzo[de,h]isoquinoline-1,3(2H)-dione;
11-{[(1Z)-(pyrid-3-ylmethylidene]amino}-2-[2-(dimethylamino)ethyl]-1H-dibenzo[de,h]isoquinoline-1,3(2H)-dione;
8-{[(1Z)-(pyrrol-2-ylmethylidene]amino}-2-[2-(dimethylamino)ethyl]-1H-dibenzo[de,h]isoquinoline-1,3(2H)-dione;
8-{[(1Z)-(thien-2-ylmethylidene]amino}-2-[2-(dimethylamino)ethyl]-1H-dibenzo[de,h]isoquinoline-1,3(2H)-dione;
8-{[(1Z)-(thien-3-ylmethylidene]amino}-2-[2-(dimethylamino)ethyl]-1H-dibenzo[de,h]isoquinoline-1,3(2H)-dione;
8-{[(1Z)-(pyrrolidinylmethylidene]amino}-2-[2-(dimethylamino)ethyl]-1H-dibenzo[de,h]isoquinoline-1,3(2H)-dione;
11-{[(1Z)-(pyrid-4-ylmethylidene]amino}-2-[2-(dimethylamino)ethyl]-1H-dibenzo[de,h]isoquinoline-1,3(2H)-dione; and
11-{[(1Z)-(pyrid-3-ylmethylidene]amino}-2-[2-(dimethylamino)ethyl]-1H-dibenzo[de,h]isoquinoline-1,3(2H)-dione,
and/or a pharmaceutically acceptable salt thereof.

2. A pharmaceutical composition comprising one or more pharmaceutically acceptable carriers and a therapeutically effective amount of a substituted azonafide derivative according to claim 1.

3. A substituted azonafide derivative according to claim 1, having anti-migratory effect against prostate, glioma, pancreas, colon, lung and breast cancer cell lines.

4. A method of treatment of a host with a disease associated with cell proliferation or cell migration, comprising administering to the host in need of such treatment a pharmaceutical composition comprising a substituted azonafide derivative according to claim 1, wherein said disease is a cancer selected from the group consisting of prostate cancer, glioma cancer, pancreatic cancer, colon cancer, lung cancer, breast cancer or any combinations thereof.

* * * * *